US008895048B2

(12) United States Patent
Stehno-Bittel et al.

(10) Patent No.: US 8,895,048 B2
(45) Date of Patent: Nov. 25, 2014

(54) TEMPLATED ISLET CELLS AND SMALL ISLET CELL CLUSTERS FOR DIABETES TREATMENT

(75) Inventors: Lisa A. Stehno-Bittel, Bonner Springs, KS (US); Karthik Ramachandran, Shawnee, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 13/558,602

(22) Filed: Jul. 26, 2012

(65) Prior Publication Data

US 2013/0029875 A1  Jan. 31, 2013

Related U.S. Application Data

(63) Continuation-in-part of application No. 13/482,671, filed on May 29, 2012, now abandoned, which is a continuation-in-part of application No. 12/798,529, filed on Apr. 6, 2010, now Pat. No. 8,735,154.

(60) Provisional application No. 61/512,303, filed on Jul. 27, 2011.

(51) Int. Cl.
| | |
|---|---|
| *A61F 2/00* | (2006.01) |
| *C12N 5/00* | (2006.01) |
| *G01N 33/50* | (2006.01) |
| *C12M 1/32* | (2006.01) |
| *C12N 5/071* | (2010.01) |

(52) U.S. Cl.
CPC ............ *G01N 33/507* (2013.01); *C12M 23/12* (2013.01); *C12N 5/0676* (2013.01); *C12N 2533/00* (2013.01)
USPC ......................................... 424/423; 435/395

(58) Field of Classification Search
CPC ............... C12N 5/00; C12N 5/02; A61F 2/00
See application file for complete search history.

(56) References Cited

U.S. PATENT DOCUMENTS

| 5,681,587 A | * | 10/1997 | Halberstadt et al. .......... 424/562 |
|---|---|---|---|
| 6,337,198 B1 | | 1/2002 | Levene et al. |

(Continued)

FOREIGN PATENT DOCUMENTS

| EP | 2 286 822 | 2/2011 |
|---|---|---|
| WO | 03044164 | 5/2003 |

(Continued)

OTHER PUBLICATIONS

Stedman's Online Dictionary : Definition of xenobiotic captured at (http://www.stedmansonline.com/content/mlrX0500000056) (2000).*
Kunz-Schughart et al. "The Use of 3-D Cultures for High-Throughput Screening: The Multicellular Spheroid Model," (Journal of Biomolecular Screening, vol. 9, pp. 273-285; 2004.*
Stedman's Online Dictionary : Definition of xenobiotic captured at (http://www.stedmansonline.com/contentJmlrX0500000056) (2000) (of record).*

(Continued)

*Primary Examiner* — Cherie M Stanfield
*Assistant Examiner* — Paul D. Pyla
(74) *Attorney, Agent, or Firm* — Hovey Williams LLP

(57) ABSTRACT

Substrates and devices for culturing cells are disclosed, along with methods of using the same. The substrates and devices include top surfaces with one or more divots disposed therein. Each divot is defined by an opening in the top surface, a rounded bottom surface spaced from the opening, and an interior side-wall surface extending between the rounded bottom surface and the opening. The top surface of the substrates and devices are optionally walled to form wells containing one or more divots. The substrates and devices may be used for reaggregating cells, for example, to form small islet cell clusters and for high throughput testing methodologies.

17 Claims, 43 Drawing Sheets

(56) References Cited

U.S. PATENT DOCUMENTS

| | | |
|---|---|---|
| 8,293,531 B1 | 10/2012 | Burg et al. |
| 2002/0173033 A1* | 11/2002 | Hammerick et al. ...... 435/305.2 |
| 2003/0096408 A1* | 5/2003 | Gerber et al. ................. 435/370 |
| 2004/0171143 A1* | 9/2004 | Chin et al. ................. 435/287.2 |
| 2006/0084159 A1 | 4/2006 | Trubetskoy |
| 2007/0122904 A1 | 5/2007 | Nordon |
| 2008/0103606 A1 | 5/2008 | Berkland et al. |
| 2008/0220520 A1 | 9/2008 | Palecek et al. |
| 2010/0233239 A1 | 9/2010 | Berkland et al. |

FOREIGN PATENT DOCUMENTS

| | | |
|---|---|---|
| WO | 2008111064 | 9/2008 |
| WO | 2009032164 | 3/2009 |
| WO | 2010031194 | 3/2010 |
| WO | 2011094572 | 8/2011 |
| WO | WO 2012120270 A1 * | 9/2012 |

OTHER PUBLICATIONS

Kunz-Schughart et al., "The Use of 3-D Cultures for High-Throughput Screening: The Multicellular Spheroid Model," Journal of Biomolecular Screening, vol. 9, pp. 273-285; 2004 (of record).*

International Search Report and Written Opinion dated Dec. 6, 2011 in related application PCT/US2011/030775 filed on Mar. 31, 2011.

International Preliminary Report on Patentability dated Oct. 18, 2012 in related application PCT/US2011/030775 filed on Mar. 31, 2011.

Choi et al., "Controlled-size embryoid body formation in concave microwell arrays," Biomaterials, 2010, 31, 4296-4303.

Office Action dated Sep. 25, 2012 in related U.S. Appl. No. 12/798,529, filed on Apr. 6, 2010.

Office Action dated Jan. 29, 2013 in related U.S. Appl. No. 12/798,529, filed on Apr. 6, 2010.

International Search Report and Written Opinion dated Feb. 27, 2013 in corresponding application PCT/US2012/048352 filed on Jul. 26, 2012.

* cited by examiner

FIG. 39

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: Acp
<220> FEATURE:
<221> NAME/KEY: MOD_RES
<222> LOCATION: (13)..(13)
<223> OTHER INFORMATION: Acp
<220> FEATURE:
<221> NAME/KEY: MOD_RES
<222> LOCATION: (15)..(15)
<223> OTHER INFORMATION: Acp

<400> SEQUENCE: 1

Glu Ile Ala Pro Val Phe Val Leu Leu Glu Xaa Gly Xaa Gly Xaa Ile
1               5                   10                  15

Thr Asp Gly Glu Ala Thr Asp Ser Gly
            20                  25
```

TEMPLATED ISLET CELLS AND SMALL ISLET CELL CLUSTERS FOR DIABETES TREATMENT

CROSS-REFERENCE TO RELATED APPLICATIONS

This application is a continuation-in-part of U.S. application Ser. No. 13/482,671, filed May 29, 2012, which is a continuation-in-part of U.S. application Ser. No. 12/798,529, filed Apr. 6, 2010. This application further claims the benefit of U.S. Provisional Patent Application No. 61/512,303, filed Jul. 27, 2011. Each application is incorporated herein by reference as if set forth in its entirety.

STATEMENT REGARDING FEDERALLY SPONSORED RESEARCH OR DEVELOPMENT

N/A

SEQUENCE LISTING The following application contains a sequence listing in computer readable format (CRF), submitted as a text file in ASCII format entitled "Sequence Listing," created on Sep. 1, 2012, as 1 KB. The content of the CRF is hereby incorporated by reference.

FIELD OF THE INVENTION

The present invention generally relates to compositions and processes for creating viable islets cells, islets, and small islet cell clusters.

DESCRIPTION OF RELATED ART

The rise in cases of diabetes mellitus in the United States has been called an epidemic. Diabetes is the third leading cause of death by disease and rivals heart disease and cancer as a major killer of United States citizens. For unexplained reasons, the occurrence of type 1 diabetes is increasing worldwide, and the age of onset has decreased by three to five years over the past decade so that many children now develop diabetes prior to entering school. The result is that more people with diabetes will spend a larger percentage of their life at risk for developing the chronic complications related to type 1 diabetes. Since the risk for development of most of the chronic complications associated with diabetes is related to glycemic control, significant attention is directed toward novel therapies, such as islet transplantation, to improve glycemic control.

Islet transplants were first attempted in the 1980s. Initial success rates for islet transplantation in humans were disappointing with only 5% of patients receiving transplants achieving partial function. See Sutherland et al., Evolution of kidney, pancreas, and islet transplantation for patients with diabetes at the University of Minnesota, Am. J. Surg. 166: 456-491 (1993). Amid the failures were isolated success stories of individuals achieving prolonged reversal of their diabetes for a 1 to 2 year period, which encouraged researchers to continue this approach to treatment of diabetes. In 2000, islet transplantations were performed successfully on seven patients with diabetes using a suppression regimen that omitted glucocorticoids, now referred to as the Edmonton protocol. See Ridgway et al., Pancreatic islet cell transplantation: progress in the clinical setting, Treat. Endocrinol. 2(3):173-189 (2003). Thus, islet transplantation outcomes have improved markedly. See Shapiro et al., Clinical results after islet transplantation, J. Investig. Med. 49(6): 559-562 (2001); Balamurugan et al., Prospective and challenges of islet transplantation for the therapy of autoimmune diabetes, Pancreas 32(3): 231-243 (2006). Yet, regardless of the optimism generated by these results, barriers to the use of islet transplantation as a practical treatment for diabetes still exist, with one barrier being the limited number of donor organs considering that most individuals require multiple transplants to achieve insulin independence.

Many factors may have an effect on transplantation success, including the physical characteristics of the islet. About 20 years ago, researchers described in detail the size and shape of islets and determined a method for estimating islet volume. See Bonnevie-Nielsen et al., Pancreatic islet volume distribution: direct measurement in preparations stained by perfusion in situ, Acta Endocrinol. (Copenh) 105(3): 379-84 (1984). For many years, large islets have traditionally been considered desirable by transplant sites for several reasons: (1) the presence of large islets is considered a hallmark of a good pancreatic digestion, since islets can be fragmented by excessive digestion, and (2) volume is used to determine the minimal number of islets needed for transplantation, and because doubling an islet's diameter is equivalent to an eightfold increase in its volume, large islets make a major contribution to the number of islet equivalents in a preparation.

In recent years, researchers have modeled the transport of oxygen, glucose, and insulin through the islet. See Dulong et al., Contributions of a finite element model for the geometric optimization of an implantable bioartificial pancreas, Artif. Organs 26(7): 583-9 (2002). Limited transport of oxygen can propagate cell death in the core of islets if the rate of oxygen consumption by peripheral cells exceeds the rate of oxygen diffusion into the islet. For example, recent studies indicate that larger islets exhibit increased necrosis when exposed to hypoxic conditions. Indeed, nearly all beta cells died when islet diameter exceeded 100-150 µm. See Giuliana et al., Central necrosis in isolated hypoxic human pancreatic islets; evidence for postisolation ischemia, Cell Transplantation 147 67-76 (2005); MacGregor et al., Small rat islets are superior to large islets in in vitro function and in transplantation outcomes, Am. J. Physiol. Endocrinol. Metab. 290(5): E771-779 (2006). The resulting oxidative stress can aggravate apoptosis and immune response upon transplantation. See Bottino et al., Response of human islets to isolation stress and the effect of antioxidant treatment, Diabetes 53(10): 2559-68 (2004). Even in cases where cell death has not occurred, a decreased metabolic rate in the islet core is probable.

Retarded transport of glucose and insulin also diminishes the functionality of pancreatic islets. The glucose gradient within an islet causes peripheral cells to contact much higher concentrations of glucose than those contained in the islet core. See Kauri et al., Direct measurement of glucose gradients and mass transport within islets of Langerhans, Biochem. Biophys. Res. Commun. 304(2): 371-7 (2003). The shape of this gradient is directly related to the diameter of the islet and the rate of glucose metabolism. Increasing islet diameter increases this diffusional and consumptive barrier in all planes within the islet.

To find another source of insulin-producing beta cells, there have also been efforts to culture beta cells in vitro. These methods have focused on the culturing of beta cells from fetal tissue or deriving such cells from islet-producing stem cells or progenitor cells. See, e.g. Peck et al., U.S. Pat. No. 6,703,017; Brothers, WO 93/00411 (1993); Neilsen, WO 86/01530 (1986); Zayas, EP 0363125 (1990); Bone et al., Microcarriers; A New Approach to Pancreatic Islet Cell Culture, In Vitro Vol. 18, No. 2 February (1982). Unfortunately, such techniques are generally time consuming and require the availability of rare fetal tissue or stem cells as their source and result in a confluent monolayer of cultured beta cells. Thus, there remains a need to create viable islets cells using more efficient, available, and reliable techniques.

In an attempt to overcome the diffusional barrier encountered in the architecture of large intact islets, various attempts were made by the present inventors to grow multiple layers of islet cells on polymer microspheres for implantation. The microspheres shown in FIG. 1A were engineered to be within the size range of intact islets. By attaching beta cells to the outer surface of the microsphere, it was theorized that there should be little or no cell death due to diffusional barriers. Multiple attempts were made using different culture environments to optimize the attachment of the cells to the microspheres, including the use of extremely high density of cells in suspension. However, this method quickly depleted the media of nutrients and cell survival was poor. Other techniques included cells that were "dripped" slowly onto the microspheres to increase the physical interaction of the cells with the microsphere or co-culturing the cells and microspheres in a microgravity chamber for several days. While some beta cells would attach to the polymer microspheres, their distribution was uneven, and multiple layers of attached cells were never consistently achieved (FIG. 1B).

BRIEF SUMMARY OF THE INVENTION

In one aspect, a substrate for culturing cells includes a substantially planar top surface and a plurality of divots disposed within the top surface. Each divot is defined by an opening in the top surface, a rounded bottom surface spaced from the opening, and an interior side-wall surface extending between the rounded bottom surface and the opening. Each divot has a depth of between 50-300 μm (±20%) and a diameter of between 100-1000 μm (±20%).

In another aspect, a device for culturing cells includes a substrate that has a substantially planar top surface and a plurality of divots disposed within the top surface. Each divot is defined by an opening in the top surface, a rounded bottom surface spaced from the opening, and an interior side-wall surface extending between the rounded bottom surface and the opening. Each divot has a depth of between 50-300 μm (±20%) and a diameter of between 100-1000 μm (±20%). The device further includes at least one well disposed on the top surface. The well include a peripheral side-wall extending upwardly from the top surface in a direction generally perpendicular to a plane defined by the top surface and forming an interior space within the well. The peripheral side-wall circumscribes the opening of at least one divot to prevent liquid communication between the at least one divot within the well periphery and an adjacent divot outside of the well.

In a further aspect, a device for culturing cells includes a substrate having a substantially planar top surface, a side-wall extending upwardly from the surface in a direction generally perpendicular to a plane defined by the top surface and circumscribing a portion of the surface. The side-wall and top surface cooperatively forming a liquid impermeable well. The well has a bottom surface corresponding to the portion of the top surface circumscribed by the side-wall and a divot disposed in the bottom surface of the well. The divot is defined by an opening in the bottom surface of the well, a rounded bottom surface spaced from the opening, and an interior side-wall surface extending between the rounded bottom surface and the opening.

In a further aspect, a method of evaluating a xenobiotic for biological activity using the micro-molds described herein is also provided. Typically, devices in such embodiments will include a plurality of wells, with each well comprising one or more divots. Cells are cultured in the divots to form a 3-dimensional cell cluster in each divot. A first xenobiotic is added to at least one of the wells such that it comes into contact with the cell cluster in each divot in that well. The effects of that xenobiotic on the cell cluster are then evaluated. Where multiple divots (and thus multiple cell clusters) are in each well, the average (mean) effects of the xenobiotic on the cell clusters can be calculated. Further, the process can be carried out with multiple xenobiotics across multiple wells facilitating high throughput screening of multiple drugs, biologics, or other compounds.

BRIEF DESCRIPTION OF THE DRAWINGS

FIG. 17A is a design where divots are close to one another, which would be useful when trying to maximize the number of reaggregates formed in a single micro-mold; FIG. 17 B is a design where divots are spaced further apart from one another, which would be useful when manipulating treatment of cells in individual divots.

FIG. 19 A shows that islets reaggregated within micro-molds contain very few dead cells, only one dead cell is stained in the upper islet, while there is no evidence of cell death in the lower islet. FIG. 19 B shows a mega-islet that formed on the undivoted surface of the micro-mold, wherein there are at least 23 dead islet cells in the confocal plane of view.

As shown in FIG. 28 A, different shapes could be designed for the divot bottom with more precision than the glass etching method. FIG. 28 B demonstrates a portion of a final biopolymer mold containing divots with distinguishing labels.

FIG. 29 A is an example of a spherical reaggregated islet. FIG. 29 B depicts is a native small islet. The shape, size, and smooth capsular-like outer edge are similar for both islets.

FIG. 39 illustrates uneven dispersion of native islets into a standard 384 well plate using automated dispersion equipment commonly used in the pharmaceutical industry. Each number indicates the number of native islets that settled into a given well.

DETAILED DESCRIPTION OF PREFERRED EMBODIMENTS

A. In General

Figure 1:
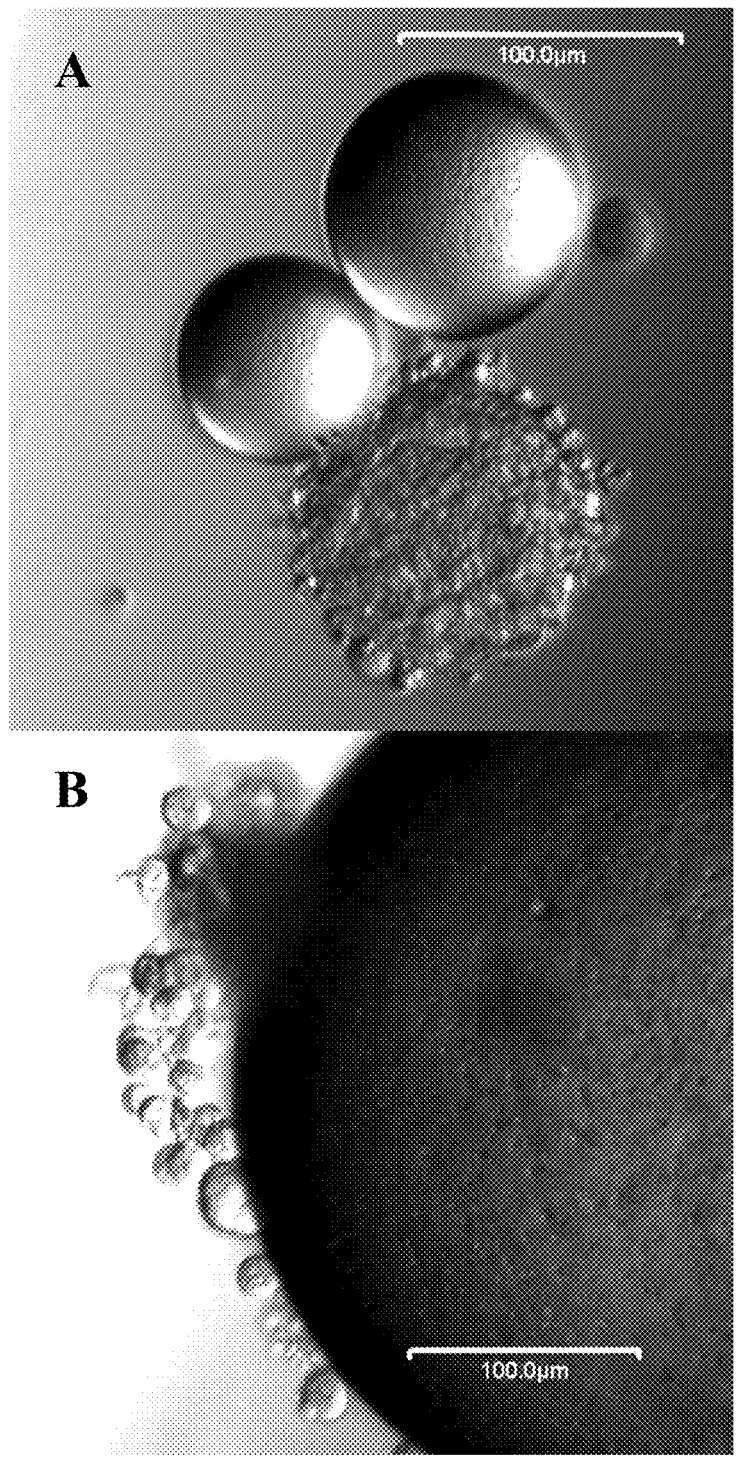
FIGS. 1A and B illustrate previous attempts to grow beta cells on microspherical polymers for implantation into a patient. In the images, an uneven distribution of cells is shown attached to a PLGA microsphere coated with chitosan polymer. A partial monolayer of cells was all that could be obtained after long-term incubation with the beta cells.

All patent applications, patents, and publications cited in this specification are hereby incorporated by reference in their entirety. In the case of inconsistencies, the present disclosure, including definitions, will prevail.

As used herein, the term "islet of Langerhans" or "islet" refers to a group of specialized cells in the pancreas that make and secrete hormones. An islet generally contains one or more of the following cell types: (1) alpha cells that make glucagon, which raises the level of glucose (sugar) in the blood; (2) beta cells that make insulin; (3) delta cells that make somatostatin which inhibits the release of numerous other hormones in the body; (4) pancreatic peptide producing PP cells; (5) D1 cells, which secrete vasoactive intestinal peptide; and (6) EC cells which secrete secretin, motilin, and substance P.

As used herein, the term "islet cell" refers to any one of the cells found in an islet. The islet cells used in the present invention are preferably a combination of insulin-producing beta cells with other islet cell types.

As used herein, the term "small islet cell cluster" or "islet fragment" refers to a collection of islet cells bound together, having usually less than about 25 islet cells in the cluster. The small islet cell cluster preferably has a morphology such that the diffusional barrier for any cell within the cluster (e.g. for nutrients, oxygen, glucose, etc.) is no more than about 7 cells. Typically, the diffusional barrier is less than about 5 cells, and may be as low as 4, 3, or 2 cells. The "small islet cell cluster" preferably comprises beta cells as the predominant cell type, and may optionally include one or more other islet cell types. The small islet cell clusters may have a variety of shapes (e.g., be generally spherical, elongated, or otherwise asymmetrical). Examples of small islet cell clusters are shown in FIGS. 5 and 6(A), 6(B), and 6(C). The "small islet cell clusters" are preferably derived by dispersing intact larger islets isolated from a donor pancreas.

As used herein, the term "native islet" refers to islets derived from a mammalian pancreas. Native islets can be characterized as "native large islets" having a diameter of greater than 125 µm, preferably greater than 150 µm, or "native small islets" having a diameter of less than 125 µm.

As used herein, the term "mega-islet" refers to a reaggregated islet having a diameter greater than about 300 µm.

As used herein, the term "adult intact islet" refers to a native large islet or a native small islet derived from an adult mammalian pancreas, wherein the islet has not been broken apart.

As used herein, the term "dispersed islet cells" refers to a suspension of cells, preferably derived by disrupting large islets such that islet cells are uniformly distributed in suspension. Preferably, no less than 90% of islet cells in suspension are single cells, the remainder comprising doublets (two cells bound together) and triplets (three cells bound together), and very few larger groups of cells bound to one another.

As used herein, the term "reaggregated islet" refers to a collection of islet cells bound together, preferably derived by breaking down large islets into single islet cells and culturing those single islet cells together in groups to form islets. Preferably, the reaggregation of single islet cells into islets is influenced by the physical dimensions of the divots in the micro-mold. The number of individual islet cells used to form a reaggregated islet is dependent on the desired size of the islet product.

As used herein, the term "diffusion barrier" refers to inhibition of molecule movement from an area of high concentration (e.g., oxygen or glucose concentration outside a cell) to an area of low concentration (e.g., oxygen or glucose concentration inside a cell). Large islets exhibit relatively high diffusion barriers to oxygen, which limits their viability and utility for transplantation. Islets reaggregated in micro-molds are small relative to native large islets, and exhibit a relatively low diffusion barrier, which contributes to cell viability within reaggregated islets.

As used herein, the term "cell viability" refers to a measure of the amount of cells that are living or dead, based on a total cell sample. High cell viability, as defined herein, refers to a cell population in which greater than 85% of all cells are viable, preferably greater than 90-95%, and more preferably a population characterized by high cell viability contains more than 99% viable cells.

As used herein, materials that are intended to come into contact with biological fluids or tissues (such as by implantation or transplantation into a subject) are termed "biomaterials." It is desirable that biomaterials induce minimal reactions between the material and the physiological environment. Biomaterials are considered "biocompatible" if, after being placed in the physiological environment, there is minimal inflammatory reaction, no evidence of anaphylactic reaction, and minimal cellular growth on the biomaterial surface. Upon implantation in a host mammal, a biocompatible biomaterial does not elicit a host response sufficient to detrimentally affect the function of the microcapsule; such host responses include formation of fibrotic structures on or around the biomaterial, immunological rejection of the biomaterial, or release of toxic or pyrogenic compounds from the biomaterial into the surrounding host tissue.

As used herein, the term "etch" refers to a chemical process using acid to create divots in a substrate.

As used herein, the term "divot" means a localized well or chamber in a substrate comprising a bottom and a side-wall (i.e., a hollowed-out space, having width and depth). In one embodiment, for the reaggregation of islets, a divot is less than 100 µm in diameter and 60 µm in depth. For example, the divot could be 80 µm in diameter and 48 µm in depth. In other embodiments where one wishes to reaggregate islets, the divots are between 80-120 μm in diameter and 48-72 μm in depth. For other purposes, such as growing mini-tumors for drug testing, the optimal divot diameter would be between 100 and 200 μm in diameter and 60 to 100 μm in depth.

As used herein, the term "divoted substrate" refers to a solid support or any material that has been modified to contain discrete individual divots.

As used herein, the term "micro-mold" refers to a device containing a surface comprised of a plurality of divots, wherein the divots measure less than about 1000 μm in diameter. The physical pattern of divots in the micro-mold can be specified by the manufacturer of the micro-mold. The micro-mold preferably comprises two main parts, which can be separately formed and subsequently attached or integrally formed as a monolithic piece, i) the divoted substrate and ii) a system to house the divoted substrate and contain cells and media therein. The micro-mold is used to guide or determine the growth or reaggregation of cells placed therein.

As used herein, the term "mold housing" refers to the structure for holding both the divoted substrate and any liquid and cell materials added thereto.

As used herein, the term "housing scaffold" refers to a temporary framework that is used to support and influence the form of materials during the construction of the micro-mold.

As used herein, the term "sputtering" means a method of vapor deposition used for depositing a thin film coating on a substrate.

As used herein, the term "well" means an interior space with the capacity to hold between tens of nanoliters to several milliliters of liquid or corresponding quantities of solids, such as, powders. Wells are typically circular or square, cylindrical or conical, but can be other shapes as well.

As used herein, the term "side-wall" means a surface that is substantially vertical that defines an area by separating at least one space from another. It is contemplated that side-walls that are particularly useful with the present invention are substantially tight to liquid.

As used herein, the term "substantially tight" means impermeable to liquids except when under sufficient pressure to produce structural discontinuity in the impermeable surface. For example, the side-walls of the disclosed walled-divoted micro-mold are substantially tight to liquid in that the surface of the side-walls is impermeable to at least 97%, 98%, 99%, or 100% of compounds adjacent to the side-wall.

As used herein, the term "micro cell culture plate," also referred to as "microtiter plate," "microplate," or "microwell plate," means a flat plate with multiple discrete wells that function as small interior volumes akin to test tubes. Micro cell culture plates contain wells typically arranged in a 2:3 rectangular matrix of 6, 24, 96, 384, 1536, 3456 or 9600 wells. Each well has the capacity to hold between tens of nanoliters to several milliliters of liquid. Micro cell culture plates are typically 85.5 mm×127.8 mm.

As used herein, the term "control compound" means a compound that that is used to define a baseline response in an experiment. A control can be used to define a baseline criterion for a positive, negative or null response to a compound.

B. Islet Cells Attached as a Multilayer

In one embodiment, the present invention is directed to a method for producing viable individual islet cells or small islet cell clusters for implantation. In one aspect, individual islet cells or small islet cell clusters isolated from non-fetal donor pancreases are attached in a multilayer to the surface of a suitable biomaterial scaffold.

In one aspect, individual islet cells, preferably beta cells, are attached to the biomaterial scaffold. In another aspect, a combination of various islet cell types are attached to the biomaterial scaffold. In still another aspect, small islet cell clusters comprised of two, three, four, five, six, seven, eight, nine, or ten cells are attached to the biomaterial scaffold.

In yet another embodiment, a multilayer of one to two, three, four, or five layers of islet cells are attached to the biomaterial scaffold. The islet cells and small islet cell clusters on the biomaterial scaffold form a multilayer of cells about 10 to 50 μm thick, most preferably about 20 to 40 μm thick.

In one aspect, the multilayer of islet cells preferably has a substantially uniform thickness such that the cell thickness varies by no more than 1-2 cells across the surface of the biomaterial scaffold.

In one aspect, the individual islet cells and/or small islet cell clusters are isolated directly from the pancreas of the donor adult subject and separated from intact islets. Suitable methods for dividing the islets into individual cells and/or small islet cell clusters include enzymatic digestion and metal-based dispersion (calcium depletion), or a combination thereof.

In another aspect, the biomaterial scaffold is comprised of a material that provides for suitable individual islet cell or small islet cell cluster adherence to the scaffold. It is contemplated that various types of materials, including inorganic and organic materials, can be used as the biomaterial scaffold of the present invention. Non-limiting examples of these materials include poly(orthoesters), poly(anhydrides), poly(phosphoesters), poly(phosphazenes), and others. Other non-limiting materials include, for example, polysaccharides, polyesters (such as poly(lactic acid), poly(L-lysine), poly (glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly (carboxyphenoxy hexane), copolymers of these monomers and the like), poly(anhydride-co-imides), poly(amides), poly (ortho esters), poly(iminocarbonates), poly(urethanes), poly (organophasphazenes), poly(phosphates), poly(ethylene vinyl acetate), and other acyl substituted cellulose acetates and derivatives thereof, poly(caprolactone), poly(carbonates), poly(amino acids), poly(acrylates), polyacetals, poly (cyanoacrylates), poly(styrenes), poly(vinyl chloride), poly (vinyl fluoride), poly(vinyl imidazole), chlorosulfonated polyolefins, polyethylene oxide, copolymers, polystyrene, and blends or co-polymers thereof). In certain preferred aspects, the biomaterials include polysaccharides, alginate, hydroxypropyl cellulose (HPC), N-isopropylacrylamide (NIPA), polyethylene glycol, polyvinyl alcohol (PVA), polyethylenimine, chitosan (CS), chitin, dextran sulfate, heparin, chondroitin sulfate, gelatin, etc., and their derivatives, copolymers, and mixtures thereof. Other suitable biomaterials include nylon, hyaluronan, polytetrafluoroethylene, polyvinyl formamide, and others described in Vats et al., Scaffolds and biomaterials for tissue engineering: a review of clinical applications, Clin. Otolaryngol. Allied Sci. 28(3): 165-72 (2003); Wang et al., An encapsulation system for the immunoisolation of pancreatic islets, Nat. Biotechnol. 15(4): 358-62 (1997); Orive et al., Cell encapsulation: promise and progress, Nat. Med. 9(1): 104-7 (2003), which are incorporated by reference.

In preferred aspects, the biomaterial scaffold is comprised of a biodegradable material. Suitable biodegradable biomaterials include poly(DL-lactide-co-glycolide) (PLO), poly-lactic acid (PLA), or poly(lactic-co-glycolic acid) (PLGA). PLG is a well-studied polymer for drug delivery and is FDA-approved for a number of in vivo applications. See Berkland et al., Fabrication of PLG microspheres with precisely controlled and monodisperse size distributions, J. Control. Release May 18, 73(1):59-74 (2001), which is incorporated by reference.

In another aspect, the biomaterial scaffold may be coated in whole or in part with a coating that increases the islet and beta cell adhesion. Exemplary coatings include fibronectin, polyethylene glycol acetate, laminin, polyvinyl alcohol (PVA), polyethylene-alt-maleic acid (PEMA), and chitosan (CS).

The scaffold may also have one or more islet cell adhesion molecules ("CAMs") attached thereto to facilitate individual cell attachment and/or small islet cell cluster attachment to the scaffold. CAMs are glycoproteins found on the cell surface that act as receptors for cell-to-cell and cell-to-extracellular matrix (ECM) adhesion and have been shown to facilitate cell attachment to polymer substrates for tissue engineering (Dunehoo et al., Cell adhesion molecules for targeted drug delivery, J. Pharm. Sci. 95: 1856-1872 (2006)). CAMs include integrins (e.g., avb3, avb5, LFA-1, VLA-4), cadherins (e.g., E-, P—, and N-cadherins), selectins (e.g., E-, L-, and P-selectins), the immunoglobulin superfamily (e.g., ICAM-1, 1CAM-2, VCAM-1, and MadCAM-1), extracellular matrix proteins (e.g., fibronectin, vitronectin, fibrinogen, collagen, laminin, and von Willebrand factor), linear and cyclic cell adhesion peptides and peptidomimetics that are derived from RGD peptides, ICAM-1 peptides, VCAM-1 peptides, cadherin peptides, and LFA-1 peptides. CAMs are important molecules for tissue regeneration, cell morphology, locomotion, mitosis, cytokinesis, phagocytosis, and the maintenance of cell polarity. It has been shown previously that cell adhesion molecules such as RGD peptides can help the process of tissue engineering, tissue regeneration, wound healing, reconstructive surgery, neural regeneration, bone grafts, and organ transplantation. In addition, E-cadherin has been shown to be important in 13-cell adhesion (Hauge-Evans et al., Pancreatic beta-cell-to-beta-cell interactions are required for integrated responses to nutrient stimuli: enhanced $Ca^{2+}$ and insulin secretory responses of MINE pseudoislets, Diabetes, 48: 1402-1408 (1999)).

In one embodiment, CAMS may be anchored onto a polymer substrate using a covalent bond(s), such as a peptide, thioether, disulfide, or ester bond. A spacer molecule may be added between the cell adhesion molecule and the polymer substrate to allow free interactions between the adhesion molecules on the polymer and the cell adhesion receptors on the cell surface. Studies to attach different cells to polymer substrates studded with RGD peptide have shown the optimal spacer between polymer and the RGD peptide to be around 11-46 angstroms for the optimal recognition of the RGD peptides by the cell surface receptors. The spacer can be made from but not limited to polyethylene glycols (PEGS), polyamino acids (e.g., poly-Gly, poly-Lys, poly-Ala), polyamino caproic acids (poly-Aca), and the combination of two or three amino acid repeats (e.g., poly-Aca-Gly). In addition to covalent linkages, CAMs can be adsorbed to a substrate by first attaching the CAM (e.g. electrostatically, hydrophobically, or by other non-covalent interactions) onto the polymers prior to attaching the islet cells.

In another aspect, the biomaterial scaffold has a shape that facilitates attachment of the individual islet cells or small islet cell clusters to its surface. The scaffold typically has a substantially planar surface, such as that on a patch or disk. In the preferred embodiment, the biomaterial scaffold comprises a substantially planar flexible patch material.

The biomaterial scaffold has a size suitable for attachment of individual islet cells or small islet cell clusters. For example, in one aspect, the planar patch typically has dimensions on the order of about 0.2 to 3 centimeters. The thickness of the patch is typically on the order of about 50 µm to 1 centimeter.

Contemplated biomaterial scaffolds may controllably release one or more growth factors, immunosuppressant agents, antibiotics, antioxidants, anti-cytokines, anti-endotoxins, T-cell adhesion blockers, angiogenesis factors, nutrients, or combinations thereof. Exemplary growth factors include, epiregulin, epidermal growth factor ("EGF"), endothelial cell growth factor ("ECGF"), fibroblast growth factor ("FGF"), nerve growth factor ("NGF"), leukemia inhibitory factor ("LIF"), bone morphogenetic protein-4 ("BMP-4"), hepatocyte growth factor ("HGF"), vascular endothelial growth factor-A ("VEGF-A"), cholecystokinin octapeptide, insulin-like growth factor, insulin, and combinations thereof. See generally Miao et al., In vitro and in vivo improvement of islet survival following treatment with nerve growth factor, Transplantation February 27; 81(4):519-24 (2006); Ta et al., The defined combination of growth factors controls generation of long-term replicating islet progenitor-like cells from cultures of adult mouse pancreas, Stem Cells, Mar. 23 (2006); Johannson, Islet endothelial cells and pancreatic beta-cell proliferation: studies in vitro and during pregnancy in adult rats, Endocrinology May; 147(5):2315-24 (2006), Epub January 26 (2006); Kuntz et al., Effect of epiregulin on pancreatic beta cell growth and insulin secretion, Growth Factors December 23(4):285-93 (2005); Vasadava, Growth factors and beta cell replication, Int. J. Biochem. Cell Biol. 38(5-6): 931-50 (2006), Epub August 31 Review (2005); Kuntz et al., Cholecystokinin octapeptide: a potential growth factor for pancreatic beta cells in diabetic rats, JOP, November 10; 5(6):464-75 (2004).

Exemplary immunosuppressant agents may be steroidal or non-steroidal. In one embodiment, a steroidal agent comprises prednisone. In another embodiment, a non-steroidal agent may include one or more of those used in the so-called Edmonton Protocol: sirolimus (Rapamune, Wyeth-Ayerst Canada), tacrolimus (Prograf, Fujisawa Canada), and anti_IL2R daclizumab (Zenapax, Roche Canada). Other candidate immunosuppressant agents include 15-deoxyspergualin, cyclosporine, rapamycin, Rapamune (sirolimus/rapamycin), FK506, or Lisofylline (LSF).

Exemplary immunosuppressant agents are well known and may be steroidal or non-steroidal. Preferred steroidal agents are prednisone. Preferred non-steroidal agents include those in the so-called Edmonton Protocol: sirolimus (Rapamune, Wyeth-Ayerst Canada), tacrolimus (Prograf, Fujisawa Canada), and anti_IL2R daclizumab (Zenapax, Roche Canada). Other immunosuppressant agents include 15-deoxyspergualin, cyclosporine, rapamycin, Rapamune (sirolimus/rapamycin), FK506, or Lisofylline (LSF).

Exemplary antibiotics may include amoxicillin, penicillin, sulfa drugs, erythromycin, streptomycin, tetracycline, chlarithromycin, ciproflozacin, terconazole, azithromycin, and the like.

Various antioxidants may include those having one or more thiol groups such as reduced glutathione (GSH) or its precursors, glutathione or glutathione analogs, glutathione monoester, and N-acetylcysteine. Other suitable anti-oxidants include superoxide dismutase, catalase, vitamin E, Trolox, lipoic acid, lazaroids, butylated hydroxyanisole (BHA), vitamin K, and the like. Glutathione, for example, may be used in a concentration range of from about 2 to about 10 mM. See, e.g., U.S. Pat. Nos. 5,710,172; 5,696,109; and 5,670,545.

Suitable anti-cytokines are well known in the art and include dimethylthiourea (about 10 mM), citiolone (about 5 mM), pravastatin sodium (PRAVACHOL, about 20 mg/kg), L-NG-monomethylarginine (L-NMMA, 2 mM), lactoferrin (about 100 μg/ml), 4-methylprednisolone (about 20 μg/ml), and the like.

Anti-endotoxins are also known in the art and include L-NG-monomethylarginine (L-NMMA, about 2 mM), lactoferrin (about 100 ug/ml), N-acetylcysteine (NAC, about 1 mM), adenosine receptor antagonists such as bamiphylline (theophylline), and In another embodiment, T-cell adhesion blockers may be used in association with the devices of the present disclosure. For example, a T-cell adhesion blocker may be bonded to or otherwise associated with a biopolymer substrate containing islet cells to suppress a subsequent potential immune reaction in the case of implantation of the substrate or reaggregated islet transplantation. T-cell adhesion blockers have been shown to suppress T-cell activation and immune response in organ transplantation and autoimmune diseases (see Yusuf-Makagiansar et al., inhibition of LFA-1/ICAM-1 and VLA-4/VCAM-I as a therapeutic approach to inflammation and autoimmune diseases, Medicinal Chemistry Reviews 22, 146-167 (2002); Anderson and Siahaan, Targeting 1CAM-1/LFA-1 interaction for controlling autoimmune diseases: Designing peptide and small molecule inhibitors, Peptides 24, 487-501 (2003)). The T-cell adhesion blockers include but are not limited to (a) monoclonal antibodies to ICAM-1, LFA-1, B7, CD28, CD2, and VLA-4, (b) soluble protein and its fragments such as ICAM-1, VCAM-1, MadCAM-1, (c) RGD peptides and peptidomimetics, (d) VCAM-1 peptides and peptidomimetics, (e) ICAM-1 peptides and peptidomimetics, and (f) LFA-1 peptides and peptidomimetics. In addition, peptides (e.g. GAD208-217) derived from glutamic acid decarboxylase 65 (GAD65) and the GAD bifunctional peptide inhibitor (GAD-BPI) have been shown to induce immunotolerance and suppress islet infiltration by T-cells (insulitis). GAD208-217 has been show to block the activation of T-cells that attack the beta cells in non-obese diabetes (NOD) mice by modulating the TCR-MHC-Ag complex formation (Signal-1) during T-cell:APC interaction (Tisch et al., Induction of GAD65-specific regulatory T-cells inhibits ongoing autoimmune diabetes in nonobese diabetic mice, Diabetes 47:894-899 (1998)). The preferred GAD-BPI comprises GAD208-217 linked to a portion of the LFA-1 peptide (sequence EIAPVFVLLE-[Ac-G-Ac-G-Ac]-ITDGEATDSG; SEQ ID NO:1), and has been shown to block T-cell activation and insulitis in NOD mice as set forth in Murray et al., Published U.S. Patent No. 2005/0107585 entitled "Signal-1/signal-2 bifunctional peptide inhibitors," which is incorporated by reference. Thus, these molecules may be co-administered to prevent rejection of the islet transplant or substrate implantation. These molecules may also be delivered via controlled release mechanisms to prevent rejection of the islet transplant/implantation. In one embodiment, the molecules may be trapped inside the biomaterial scaffold before the beta cells are attached to the scaffold.

The controlled release of such agents may be performed by using the protocols set forth in Raman et al., Modeling small-molecule release from PLG microspheres: effects of polymer degradation and nonuniform drug distribution, J. Control. Release. March 2; 103(1):149-58 (2005); Berkland et al., Precise control of PLG microsphere size provides enhanced control of drug release rate, J. Control. Release. July 18; 82(1):137-47 (2002); Schwendeman, Recent advances in the stabilization of proteins encapsulated in injectable PLGA delivery systems, Crit. Rev. Ther. Drug Carrier Syst. 19(1): 73-98 (2002); Sershen et al., Implantable, polymeric systems for modulated drug delivery, Adv. Drug Deliv. Rev. 5; 54(9): 1225-1235 (2002), all of which are incorporated by reference.

C. Production of Islets on Divoted Micro-Molds

The present invention is also directed to a method for in vitro production of viable small islets. In one aspect, dispersed islet cells isolated from non-fetal donor pancreases may be placed in groups into individual divots of a micro-mold and cultured to form reaggregated islets whose shape and size are influenced by divot dimensions.

The divots of the micro-mold may have a size suitable for formation of small islets. For example, the micro-mold may have dimensions on the order of about 30-35 mm in diameter, but this size is not limited by production methods and could be ramped up to 30×30 cm. The divots typically have dimensions on the order of about 100-200 μm (±20%) in diameter and 60-100 (±20%) μm in depth. Preferably, for the production of islets the divots are 100 μm (±20%) in diameter and 60 μm (±20%) in depth.

It is envisioned that the micro-molds of the present disclosure may be used to generate populations of optimally shaped and sized islets suitable for transplantation or in vitro study. For example, a population of islets generated in micro-molds may have a mean diameter of 50 μm or less. In other aspects, the population is characterized by at least 85% viable cells, preferably greater than 90% or 95% viable cells, more preferably the population is characterized by greater than 99% viable cells.

In yet another aspect, the population of islets generated in micro-molds can be characterized by high levels of insulin secretion. For example, small islets reaggregated in micro-molds are characterized by greater levels of insulin secretion relative to native small islets, preferably greater than 20 times more insulin secretion, more preferably greater than 100 times more insulin secretion. For example, the reaggregated islets measured secretion of approximately 10 ng/IE, shown in FIG. 23. This is 41 times greater than the best calculated value from Crim et al., 2010. One difficulty in comparing insulin secretion data between laboratories is that many investigators fail to report their insulin secretion per islet volume. In the case of Crim et al, they reported insulin secretion per 50 islets, but did not indicate the average size of the islets. Thus, one can only assume that their 50 islets were each equivalent to the previously defined islet volume of 1 islet equivalency (IE). Our laboratory always reports insulin secretion normalized for the total volume of islets and cells by dividing by the IE. With the assumption made for the Crim paper, the reaggregated islets described herein release over 40 times more insulin in response to high glucose than the best conditions reported by Crim et al.

In one embodiment of the present invention, the micro-mold will be used to create cells useful for in vitro testing and other in vitro applications. In that embodiment, the micro-mold surface is preferably made of glass with the mold sides (the housing system) made of PDMS.

In another embodiment, the micro-mold may be implantable and made of bio-compatible materials described previously.

In another aspect, the micro-mold divots are designed to provide optimal physical reformation conditions for non-islet cells. It is contemplated that various types of cells can be formed in the divots of the present invention. Non-limiting examples include, long neuronal pathways, glomerular-like filters, vessels, replacement alveoli, and the like. Aggregation of stem cells or reprogrammed cells in a small, well-defined shape, such as the micro-mold, would also be an appropriate use of this invention. Preferable cell types include those in which a 3-D structure is important to cell function.

Figure 24:
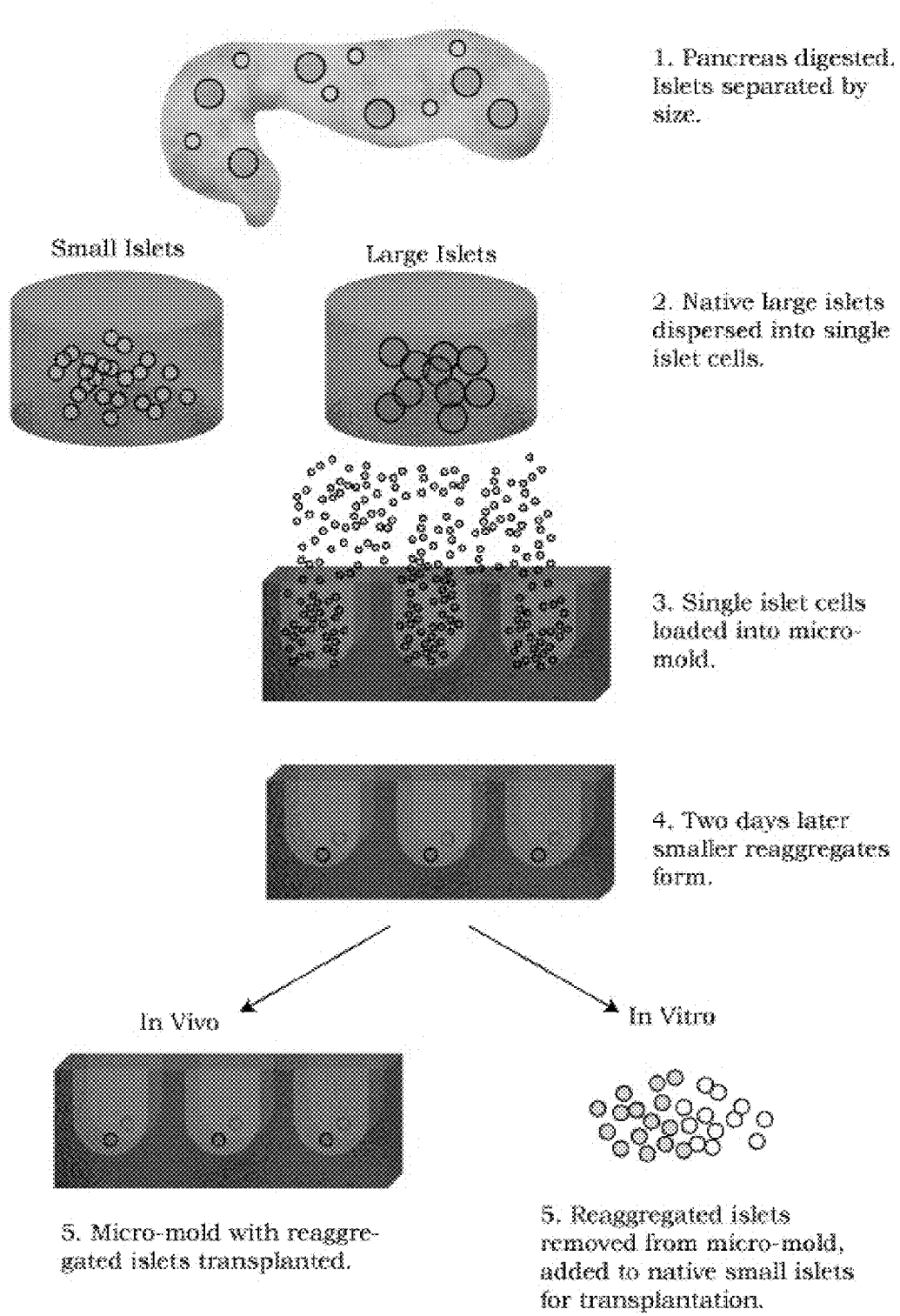
FIG. 24 is a schematic flow chart illustrating the general method for using the instant micro-mold to reaggregate optimally-sized islets.
Figure 25:
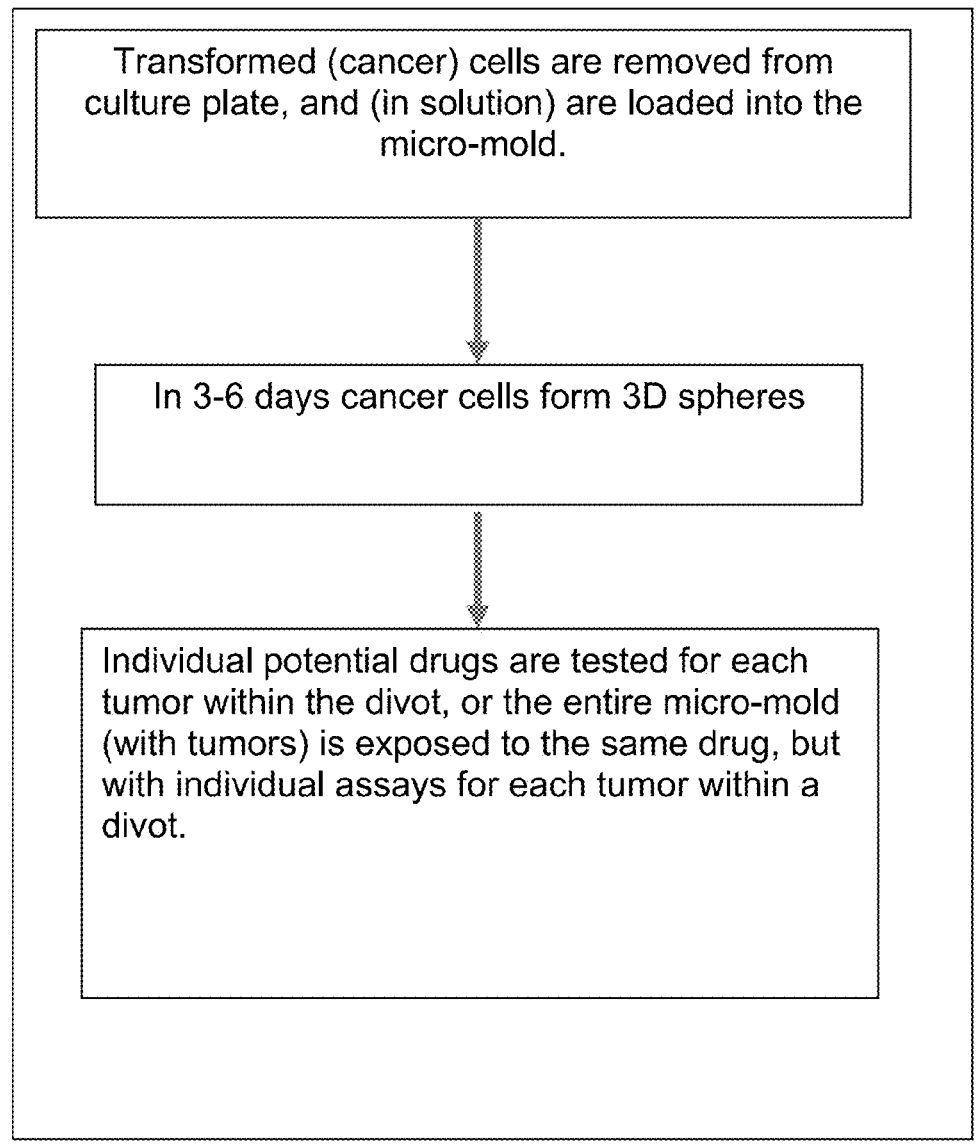
FIG. 25 is a schematic flow chart illustrating one exemplary use of the instant micro-mold for high-throughput drug testing. Additional exemplary uses are illustrated in FIGS. 34-35.

In general, FIG. 24 is a schematic showing the seeding of a micro-mold of the present disclosure. Native islet clusters, taken from a pancreas or other islet source, may be dispersed into single islet cells and loaded onto a micro-mold with divots. By "dispersed cells" we mean that the majority (typically at least 90%) of cells are single cells, with a lesser proportion of cells bound together as doublets or triplets. The dispersed cells are placed into the micro-mold in a manner that leads to groups of the dispersed cells settling into each divot. Preferably, 30-150 cells settle into each divot.

Example 5 discloses a preferred method of dispersing islets into single cells and incubation of the cells in micro-molds. Preferably, the dissociation is in a media blend formulated in the KU Diabetes Research Laboratory. This blend includes nine parts calcium-magnesium free Hank's Balanced Salt Solution and one part papain (50 units/ml). In contrast, most islet dissociation is accomplished using trypsin or enzymes other than papain. The dissociation is carried out at 37° C., with rotation. Finally the islets are dispersed into single cells by manually pipetting them and observing with a hemocytometer until at least 90% of the cells are separated into single cells. Example 5 also discloses preferable conditions for the reaggregation of the islet cells within the micro-molds. In general, the cells remain as single cells or loosely attached groups of cells through day two as noted in FIG. 14. However, by day five or six those same cells in the divot have reorganized into a 3D structure that is often spherical (for examples see FIGS. 18-19A and 21). Typically by day five, the reaggregated islets can withstand removal from the molds and function as independent islets.

During this period of time, the cells take on the three-dimensional shape of a native islet. The mean diameter of the islets formed in the divots is less than 50 μm. Example 5 describes the morphological nature of the small islets formed in the micro-molds.

In one embodiment of the present invention, cells dispersed in low concentration can be added to the micro-mold, such that as few as two or three cells fall in each divot, and such that cells within divots are capable of growth and division. The shape and size of the cell mass grown in a divot in this manner may be influenced by the physical dimensions of the divot. Preferably, micro-molds are loaded with islet cells, concentrated such that as few as two or three islet cells will occupy each divot, wherein islet cells will grow and aggregate together to form small islets, preferably 30-40 μm in diameter.

In another embodiment of the present invention, one may wish to incorporate chemicals or biological molecules into the engineered islets at the time of reaggregation. These molecules include growth factors, cytokines, chemokines, DMARDs (disease-modifying antirheumatic drugs), anti-inflammatories, and antibiotics. Molecules or miniature devices to increase oxygen tension at the transplant site could be incorporated into the reaggregated islets, especially if an implantable micro-mold substrate were used. Other non-limiting classes of molecules that could be added at the time of reaggregation includes drugs to induce insulin release, small molecules, peptides, proteins, antibodies (e.g. against CD11a, CD11b, CD11c, CD18), and nucleic acids (e.g. DNA or RNA).

Such molecules could typically be incorporated into the islets at the time of loading into the micro-molds. The molecules would be added to the media with the dispersed cells so that they would be either taken up by the cells or adhere to the cells during aggregation. Alternatively, the cells could be modified prior to reaggregation via standard transfection methods that would result in increased or decreased production of the user's target protein. After the formation of the reaggregates, the newly-formed islets could be encapsulated with biopolymers that would carry chemicals such as immunosuppressors or other molecules of interest such as growth factors. Alternatively, with implantable micro-molds, the molds could be impregnated with the molecule of choice.

The method of the present invention can be designed to form cell aggregates for subsequent transplantation or for drug or device testing. Example 5 describes preferable methods for reaggregating cells for transplant and drug screening and preferable methods for doing so.

In another aspect, the present invention is also directed to a method for high-throughput screening of drugs, chemicals, or other small molecules. It is contemplated that the pattern and dimensions of divots in the present micro-mold can be designed to accommodate individual interventions in each divot.

Figure 8:
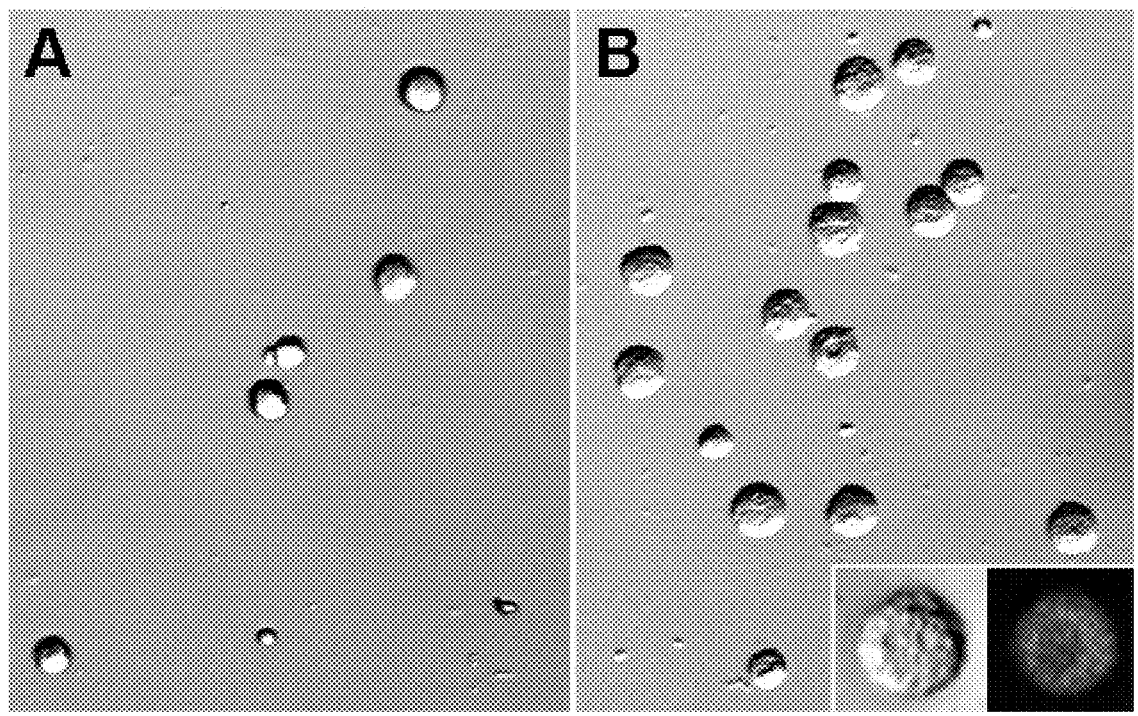
FIG. 8 are optical micrographs of beta cell adhesion to (A) chitosan (Mw=100 kDa) and (B) laminin. The inset shows optical and fluorescent micrographs of a beta cell on laminin with cytoch B (green) stain for actin.

In another aspect, the divoted micro-molds are generated from a biopolymer suitable for transplantation into an animal host. We envision that cells reaggregated in an implantable micro-mold may or may not adhere to the divoted substrate. For in vitro work, a non-adherent substrate surface, such as glass, is preferable. However, for implantable molds, or biopolymer patches, adherent substrates would enhance the efficiency of the transplantation process with decreased loss of islets during and after transplantation. Adherence of the cells to the biopolymers has been tested and is described in Table 1 and FIG. 8.

D. Method of Screening A Compound For Biological Activity Using Micro-Molds

A preferred embodiment of the claimed invention is a micro-mold, including a top planar surface and a plurality of divots disposed therein. Each divot is defined by an opening in the top surface, an interior bottom surface spaced from the opening, and an interior side-wall surface extending between the bottom surface and the opening in the top surface. In some embodiments, the bottom surface can be rounded or concave. The divots extend in a direction generally perpendicularly below a plane defined by the top surface to form a generally concave structure within which islets may be cultured. In another embodiment, a wall-modified micro-mold is provided, wherein walls extend from the top surface in a direction generally perpendicularly above the plane defined by the top surface. The walls cooperatively separate, segregate, divide, or otherwise wall-off adjacent divot openings in the top surface and may be used to separate individual divots or groups of divots (see FIGS. 34 and 35, respectively). The walls in combination with the top surface of the micro-mold define a discrete interior space or "well." The wells enable liquids, for example, media and/or additional chemicals to be added to a 3D cell cluster cultured within the one or more divots contained within the well. The wall-modified micro-mold is particularly advantageous for high throughput screening.

Figure 30:
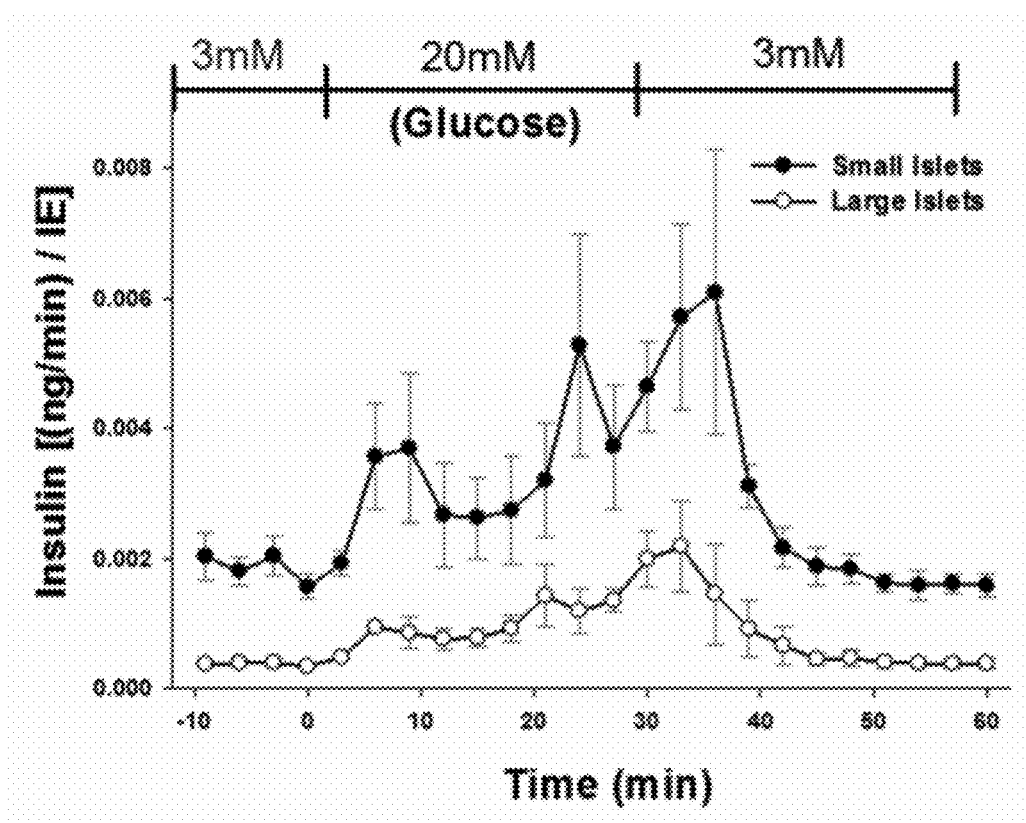
FIG. 30 illustrates a comparison of glucose-stimulated insulin release from large and small islets from the same donor.
Figure 31:
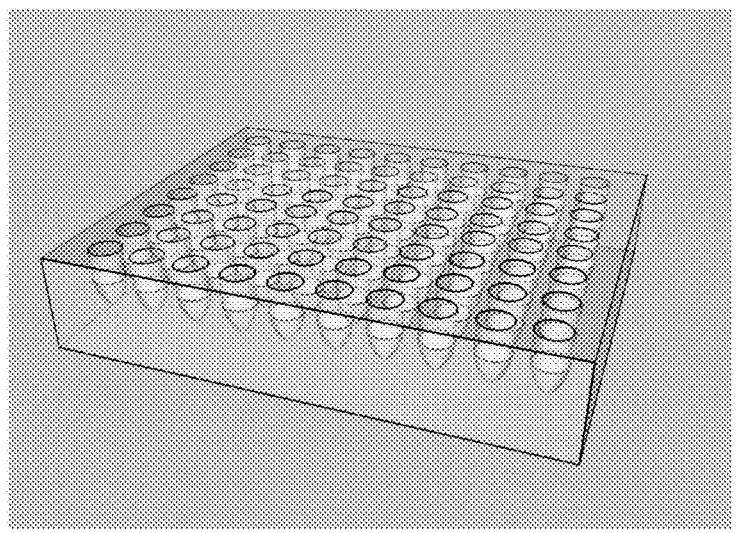
FIG. 31 is a schematic illustration of the micro-mold described in Example 5.

Current drug screening and toxicology testing involves a first pass screen using cells cultured as a monolayer on the bottom of a Petri dish. Cells grown in a monolayer can exhibit different responses to compounds relative to in vivo cells of the same type. For example, insulin-secreting beta cells do not secrete insulin in the same manner when they are cultured as a monolayer in a Petri dish as they do when they are cultured as 3D spheroids that better resemble their in vivo cellular structure. However, using 3D spheroids in compound screening has been extremely problematic. For example, 3D spheroids cultured using known techniques exhibit non-uniform cell number and composition and a high diffusion barrier. Such variation leads to inconsistent cellular responses to test compounds. Further, current methods for culturing 3D spheroids of cells are not compatible with industry high-throughput instruments, not scalable to high throughput needs and not appropriate for maintaining long-term experiments. An additional challenge presented by known techniques is the size variation within islets from the same donor. Small islets release more insulin in response to high glucose concentrations than large islets (MacGregor et al., 2006; FIG. 30).

The micro-mold described in Example 5 is particularly useful when the resulting cell clusters are to be removed from the mold for research or transplant purposes. The micro-mold described in Example 6 is particularly useful for drug and toxicology screening, including high throughput screening. The micro-molds described in Example 6 allow the segregation of either single divots or a plurality of divots (FIGS. 34 and 35, respectively) into separate wells. For example, using a known 384- or 1536-well plate design (85.5×127.8 mm dimensions), which is standard in high throughput screening, multiple (for example, 2-14 or more) divots can be created within a single well of the 1536-well plate. A 1536-well plate with 14 divots/well would have divots suitable for culturing 21,504 cell clusters. It follows that a compound dispensed into a single well would be in contact with up to 14 different cell clusters, providing 14 replicates from which to measure an average response/well. The number of cell clusters created per well may be altered to suit the end-users' goals.

The walled-micro-mold design improves the reliability of micro-mold-derived cell cluster responses to test compounds relative to testing of native islets under identical conditions, at least because the assay is not dependent on a single intact islet or even a single cell cluster to produce a measurable response. Rather the response assayed in each well is an average response from 3-14 cell clusters. Advantageously, the same micro-mold used to grow the cell clusters is compatible with standard industry instruments for the dispensing of test compounds. Each transfer step that is eliminated in the production and testing of cell clusters improves screening efficiency and reduces the risk of contamination.

In one embodiment, the present methods can include aspects performed on a computing system. As such, the computing system can include a memory device that has the computer-executable instructions for performing the method. The computer executable instructions can be part of a computer program product that includes one or more algorithms for performing any of the methods of any of the claims.

In other embodiments of the claimed invention, the walled micro-mold can be used to reaggregate and screen non-islet cell types, at least for example, cancer cells, and cells relevant to heart disease, vascular disease and endocrine disorders. It is contemplated that non-islet cells can be cultured and subsequently tested for biological activity when treated with one or a plurality of compounds using the walled micro-molds described herein. Advantageously, one or a plurality of compounds can be applied to one or a plurality of non-islet cell clusters using the disclosed micro-molds.

Additional aspects of the invention, together with the advantages and novel features appurtenant thereto, will be set forth in part in the description and examples which follow, and in part will become apparent to those skilled in the art upon examination of the following, or may be learned from the practice of the invention. The objects and advantages of the invention may be realized and attained by means of the instrumentalities and combinations particularly pointed out in the appended claims.

EXAMPLES

Example 1

Size of Islet Impacts Viability and Transplantation Success

This example investigated how islet size affected transplantation success in rats. In this example, techniques for isolating islets are described, and cell viability was measured. Both large islets (greater than 125 μm) and small islets (less than 125 μm) were transplanted in order to assess the effect of islet size on transplantation success. As discussed below, small rat islets are superior to large islets in in vitro function and in in vivo transplantation outcomes. These experiments are also described in MacGregor et al., Small rat islets are superior to large islets in in vitro function and in transplantation outcomes, Am. J. Physiol. Endocrinol. Metab. May; 290 (5):E771-9 (2006), which is incorporated by reference in its entirety.

Rat Islet Isolation.

To isolate large and small islets, adult male DA rats were anesthetized by intraperitoneal injection of a mixture of ketamine and xylazine. The peritoneal cavity was exposed and the pancreatic ductal connection to the intestine clamped. The pancreas was cannulated in situ via the common bile duct, and distended by pumping a cold solution of collagenase into the duct. Collagenase (CLS-1, Worthington Biochemical Corp, Lakewood, N.J.) was dissolved in 20 ml of Leibovitz L15 at 450 U/ml. Subsequently, the distended pancreas was excised, transferred to 50 ml centrifuge tubes, and incubated for about 20-30 minutes with gentle tumbling in a 37° C. incubator. Following incubation, the tube was gently shaken to dislodge islets. The contents of the tube were placed in diluted ice-cold Hank's Balanced Salt Solution ("HBSS") containing 10% of newborn calf serum. The digest was allowed to settle at 1×g and the supernatant removed. More HBSS/serum was added and the process repeated. The washed digest was passed through a 500 micron stainless steel screen and sedimented about 1 minute at 300×g in a refrigerated centrifuge. The pellet was mixed with 10 mL of 1.110 gm/mL Histopaque (density=1.1085, Sigma Diagnostics Inc., St. Louis, Mo.) and centrifuged 10 minutes at 800×g. The islets floating on the gradient were collected and sedimented separately, then placed into Ham's F12 culture medium containing 10% of fetal bovine serum and put into a 37° C. culture chamber containing 5% $CO_2$.

Yield

For yield measurements, triplicate samples of each batch of islets were examined, each comprising approximately 2% of the islet fraction. Individual islets were counted and their diameters measured. For irregular-shaped islets, 3 to 4 diameter measurements were taken at different locations on the islet and averaged. Islet volumes were calculated and converted to islet equivalents for the sample and the entire islet fraction. Small islets were defined as those having a diameter of less than about 125 μm compared to large islet with a diameter of about 125 μm or greater.

To separate small islets from large islets, fresh islets or islets cultured overnight were sedimented and then placed in 1-2 ml of L15 medium. The islets were then quickly layered over a single-step gradient of 5% BSA in L15. Sedimentation at 1×g was permitted to occur for an empirically set period of time until large islets were observed in the bottom of the tube. At that point the top two milliliters (without BSA) of the gradient was discarded, and all but the bottom 2 ml was carefully removed to define the small islet population. The sedimented islets and those in the bottom 2 milliliters were combined as the large islet fraction. Gradients were repeated if needed to optimize the separation of large and small islets. Final islet fractions were sedimented and place into culture in a 1:1 mixture of Ham's F12 and glucose-free RPMI 1640 (glucose=5 mM) until glucose sensitivity experiments were performed.

Viability

To test viability, islets were placed in a 500 µl volume of L-15 media with live/dead fluorophores, Sytox (Molecular Probes, 1 µM) and Calcein (Molecular Probes, 0.5 µM), and incubated for about 15 to 30 minutes at 37° C. Islets were rinsed with phosphate buffered saline (PBS) consisting of (in mM): 137 NaCl, 2.7 KCl, 4.3 $Na_2HPO4$ and 1.4 $KH_2PO_4$, pH 7.4 and placed in the Attofluor Chamber (Molecular Probes) on the Olympus Fluoview 300 confocal microscope. Images were acquired using 40× or 60× objectives. All images were collected within 20 minutes of removal of the islets from the media. Three simultaneous images were collected for each islet using He:Ne and Argon lasers and a third bright-field image.

Figure 2:
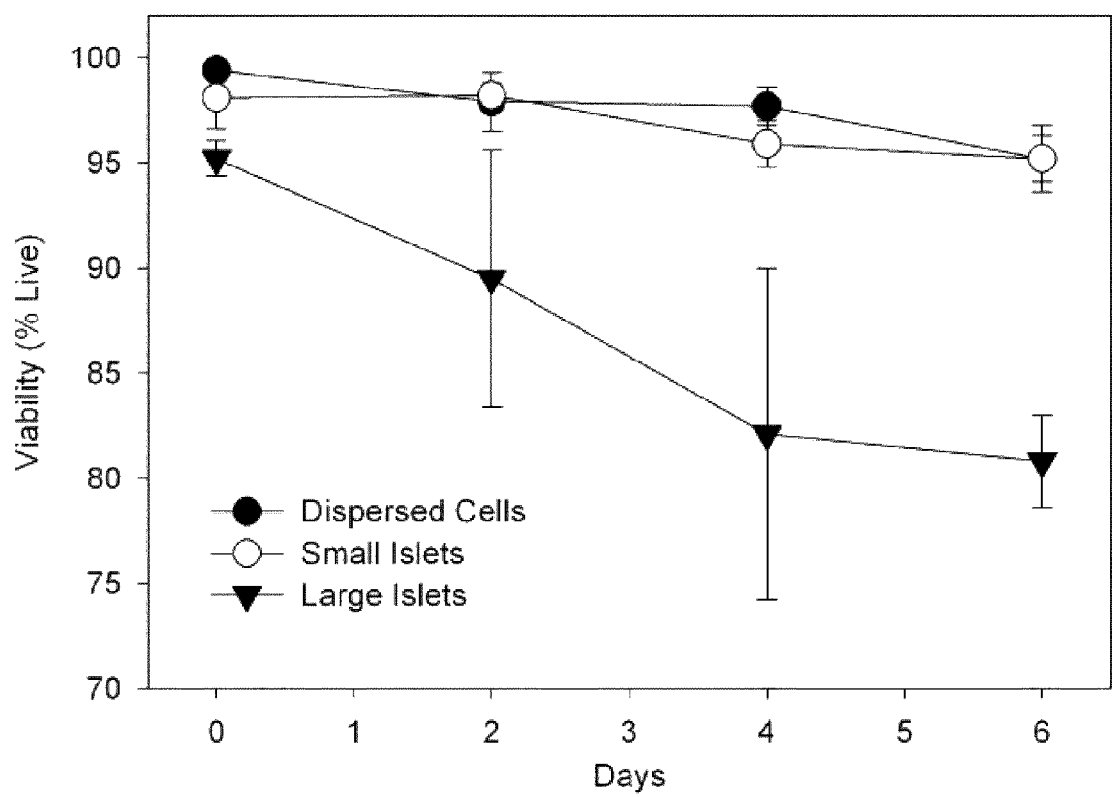
FIG. 2 is a graph that compares the cell viability for cultured large rat islets (greater than 125 μm), small islets (less than 125 μm), and dispersed beta cells as a function of time. The decreased viability of large islets is statistically significant ($p<0.05$) beyond day 3.

As shown in FIG. 2, large intact islets (greater than 125 µm), whether human or rat, maintained in culture typically exhibit a significant percentage of necrotic (12.6%) and apoptotic (6.3%) cells after only four days with cell death increasing over time. Smaller islets (less than 125 µm) exhibited extended viability, but still showed precipitous cell death at later time points (beyond one week). The viability of these small islets was followed for up to one week, and it was found that they maintain high viability percentages from 99 to 86%. This is in comparison with 10 intact large islets, which have viability levels that fall to below 50% after several days in culture. As shown in FIG. 2, individually dispersed islet cells maintain a high viability profile in culture similar to the small intact islets.

Live/dead analysis was completed by identifying the islets in the field and encircling the regions of interest. Background fluorescence was subtracted from all images. Viability percentages were calculated by developing hue histograms using Photoshop (Adobe) from the fields of interest and calculating the total pixels in the green hue (live) and red (dead). The ratio representing the live cells divided by the total islet area was calculated as the percent live value. Islet diameters and perimeters were calculated using Scion software so that viability values could be categorized according to the size of the islet.

Transplant Studies.

The effect of islet size on transplantation success was also investigated. In the experiments, diabetes was induced in the recipient animals by injecting streptozotocin (65 mg/kg) intraperitoneally (1 injection). When blood glucose levels are greater than 250 mg/dl for three consecutive days, the rats were considered diabetic.

Rats were anesthetized with pentobarbital 45 mg/kg. After the rat was shaved and cleaned with betadine scrub, an incision was be made in the body wall on the left flank. The kidney was delivered into the wound, and a small incision was made in the kidney capsule. The large or small islets were placed under the capsule using a small bore pipette. The kidney was placed back into original position and the incision closed with wound clips. Beef/porcine zinc-insulin (NPI-1 Iletin I) injections (2 times/day) were given to recipients for three days post-islet transplant to reduce the stress of hyperglycemia on the newly transplanted islets.

Figure 3A:
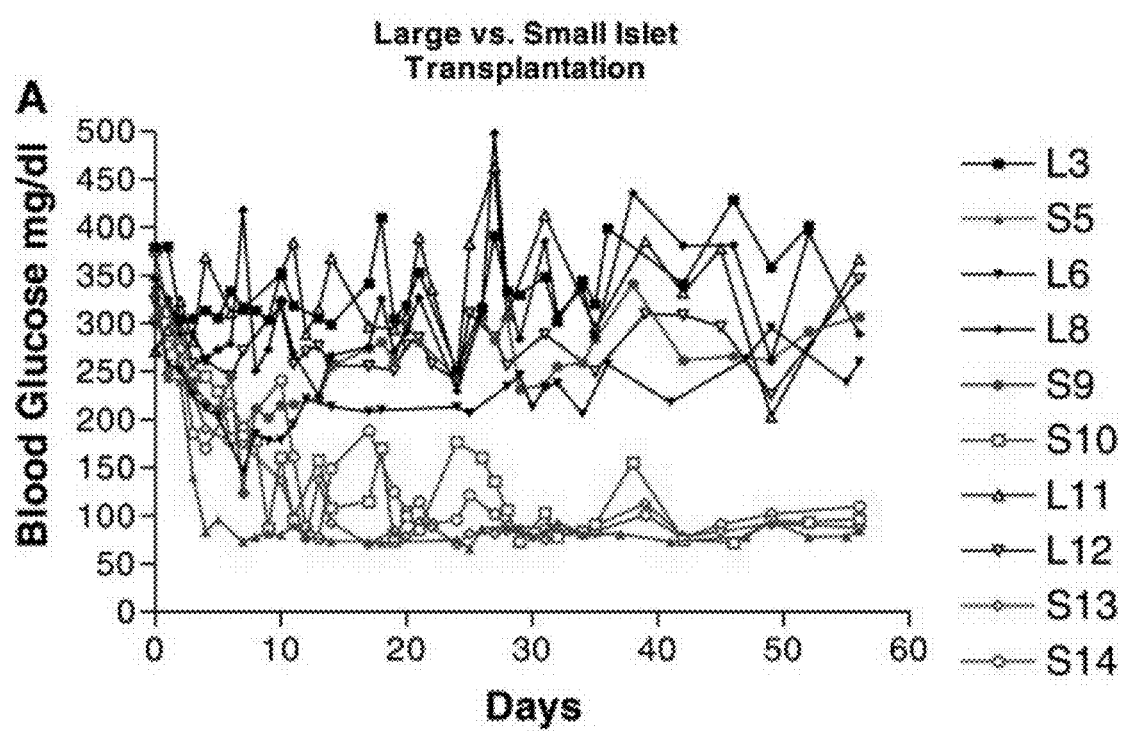
FIGS. 3A and B summarize the results of transplantation of small islets (less than 125 μm) or large islets (greater than 125 μm) into diabetic rats. A successful return to euglycemia was observed about 80% of the time when small islets were used, but transplants were unsuccessful in restoring normal plasma glucose levels when the large islets were transplanted. This can be best illustrated by showing the plasma glucose level of the animal in each group 60 days after transplantation. The animals receiving large islets remained hyperglycemic after the transplant, while the rats receiving small islets were euglycemic. * indicates significant difference of 0.01.
Figure 3B:
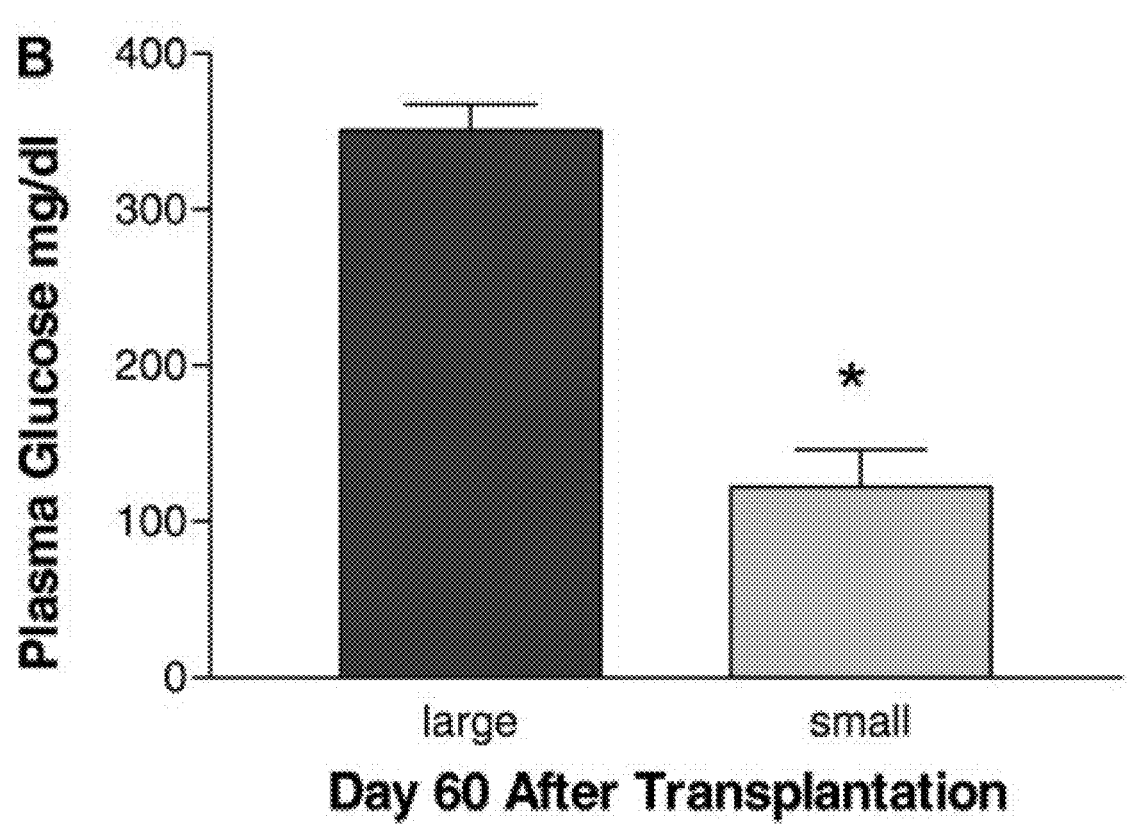

Transplantations of the large or small rat islets were completed (n=10 transplantations/group). The streptozotocin-induced diabetic DA rats received a marginal mass (1000 IE) of either large (greater than 150 µm) or small (less 125 µm) syngenic islets under the kidney capsule. Blood glucose levels were monitored for eight weeks. FIGS. 3(A) and 3(B) show the results from the first five transplants for each group. All of the recipients of large islets remained hyperglycemic after transplantation (10 of 10). In contrast, 8 of 10 recipients of small islets had blood glucose levels close to or at normal levels 7-10 days after transplantation, which remained normal for the entire eight-week period.

Figure 4:
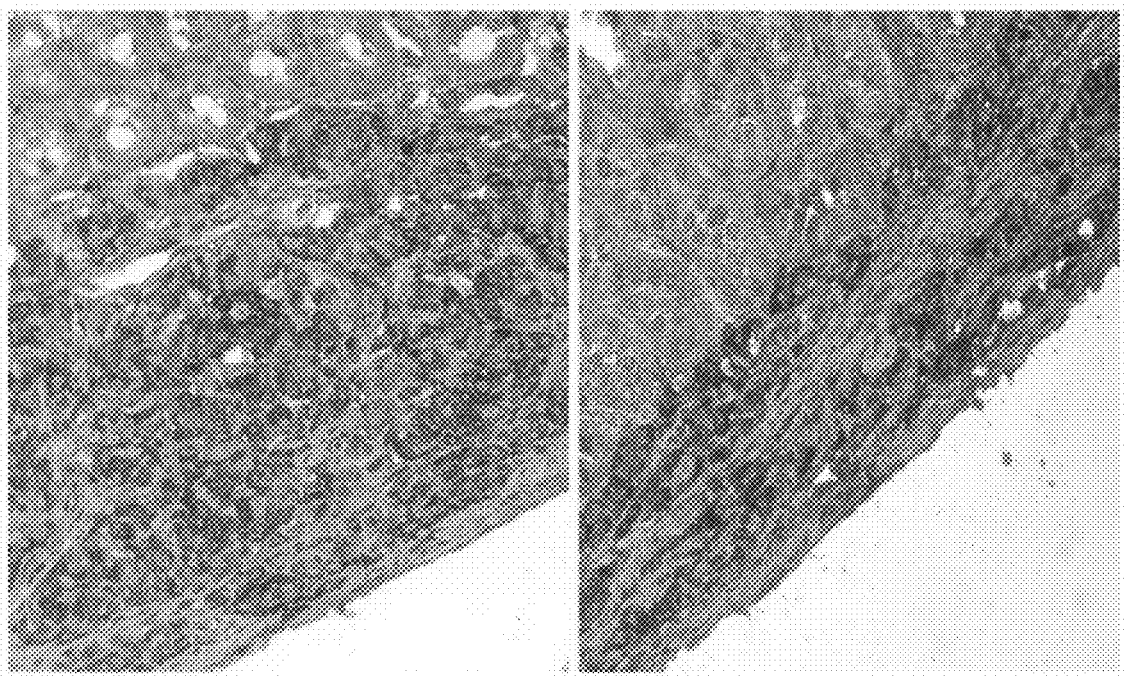
FIG. 4 is an islet graft removed from the kidney capsule about eight weeks after transplantation and immunolabeled for insulin. The image on the left panel shows relatively more insulin immunolabeling (red) and an established capillary network in a graft using small islets (less than 125 μm). In contrast, grafts of large islets (greater than 125 μm) showed little insulin immunolabeling and significant fibrosis (right panel). The images are representative from four different animals.

Islet grafts from the kidney capsule were removed eight weeks after transplantation. The tissue was fixed and immunolabeled for insulin. FIG. 4 (left panel) shows the graft from an animal that received small islet transplantation and was euglycemic for the eight weeks. There was substantial staining for insulin in the graft. In contrast, the animal that received the transplantation of large islets continued to be hyperglycemic for the eight week period and showed little immunolabeling for insulin in the grafts (FIG. 4, right panel).

Together, the foregoing experiments show that smaller islets (less than 125 µm) were superior to large islets (more than 125 µm) in viability, in vivo functional assays, and in transplant outcomes. In addition, an average pancreas yielded about three times more small islets than large islets, and the smaller islets were approximately 20% more viable. Most importantly, the small islets were far superior to large islets when transplanted into diabetic animals.

Example 2

Conversion of Large Islets into Individual Islet Cells or Small Islet Cell Clusters This example illustrates methods for fragmenting or dispersing intact islets into small islet cell clusters (such as the cluster shown in FIG. 5) and individual islet cells. The small islet cell cluster in FIG. 6A was created using a conventional enzymatic digestion, while the small islet cell cluster in FIG. 6B was formed with graded calcium depletion. As the image in FIG. 6A illustrates, enzymatic dispersion breaks the islet down into small islet cell clusters, but it does not "open" the cluster up so the cells on the interior of the cluster have a diffusional barrier that is several cells thick. In contrast, for small islet cell clusters formed using calcium depletion (FIG. 6B), the cluster has an "open" morphology such that there is a smaller diffusional barrier for each cell of the when the small islet cell cluster. It is anticipated that a combination of enzymatic digestion and calcium depletion may also be used to convert intact islets into small islet cell clusters, as shown in FIG. 6C.

Enzyme Digestion.

Different enzyme cocktails can be used to fragment intact islets into small islet cell clusters and individual islet cells. Exemplary enzymatic digestion methods are disclosed in U.S. Pat. No. 6,783,954, which is incorporated by reference. In this example, twelve enzyme cocktails were used with varying degrees of success, including one cocktail, which included papain.

To isolate pancreatic islets, Sprague-Dawley rats were anesthetized by an intraperitoneal injection of ketamine and xylazine. The peritoneal cavity was exposed and the pancreatic ductal connection to the intestine clamped. The pancreas was cannulated in situ via the common bile duct, and distended by pumping a cold solution of collagenase into the duct. Subsequently, the distended pancreas was excised, transferred to centrifuge tubes, and incubated for about 30 minutes with gentle tumbling in a 37° C. The washed digest was passed through a screen and sedimented in a refrigerated centrifuge. The pellet was mixed with Histopaque (density=1.1085, Sigma Diagnostics Inc., St. Louis, Mo.) and centrifuged. The islets were then placed into Ham's F12 culture medium containing 10% of fetal bovine serum and put into a 37° C. culture chamber containing 5% $CO_2$.

The standard protocol for beta cell isolation included incubating intact islets (isolation using techniques described herein) in Hanks Balanced Salt Solution ("HBSS") with 4.8 mM Hepes. See Balamurugan et al., Flexible management of enzymatic digestion improves human islet isolation outcome from sub-optimal donor pancreata. Am. J. Transplant 3(9): 1135-42 (2003). For enzymatic digestion, a final 9 ml of Hanks balanced salt solution containing 1 ml of papain (50 units/ml) was added to the islets. Islets were initially pipetted up and down gently to ensure complete rinsing. Islets were allowed to settle to the bottom of the tube and most of the supernatant was removed. Islets in the enzyme were rotated slowly (about 10 rpm) for about 30 minutes at 37° C. At this point, small islet clusters were formed with some single dispersed cells, and removed from the solution. Typically, the cells were transferred to CMRL 1066 or Memphis SMF as the final culture media.

Figure 5:
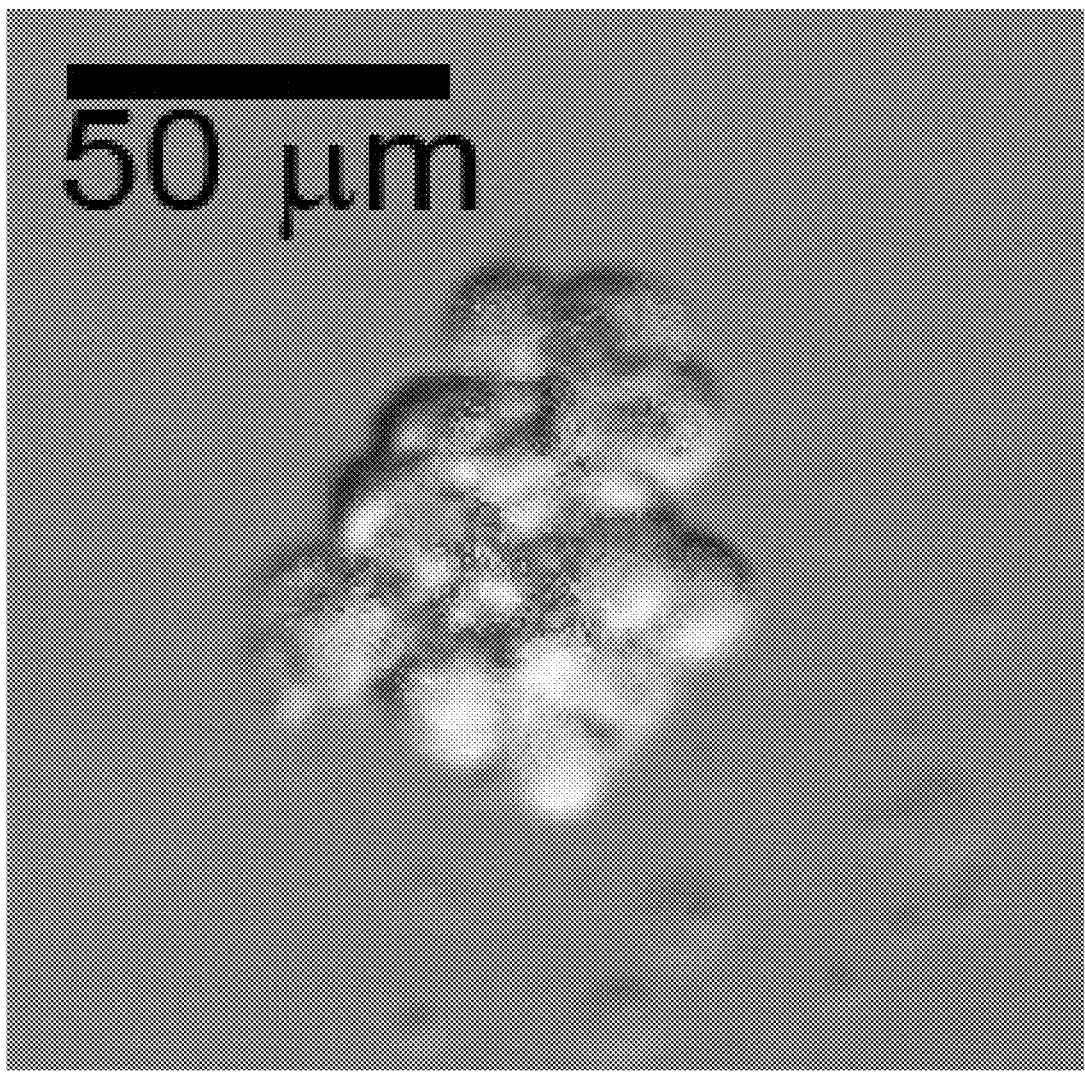
FIG. 5 shows a rat small islet cell cluster stained with dithizone to identify beta cells. Because the confocal aperture was set for an extremely thin Z section, the cells within the subunit, but below the plane of focus are blurry and do not appear red. However, adjustment in the confocal plane to those cells indicated that they also were clearly stained with dithizone.
Figure 6:
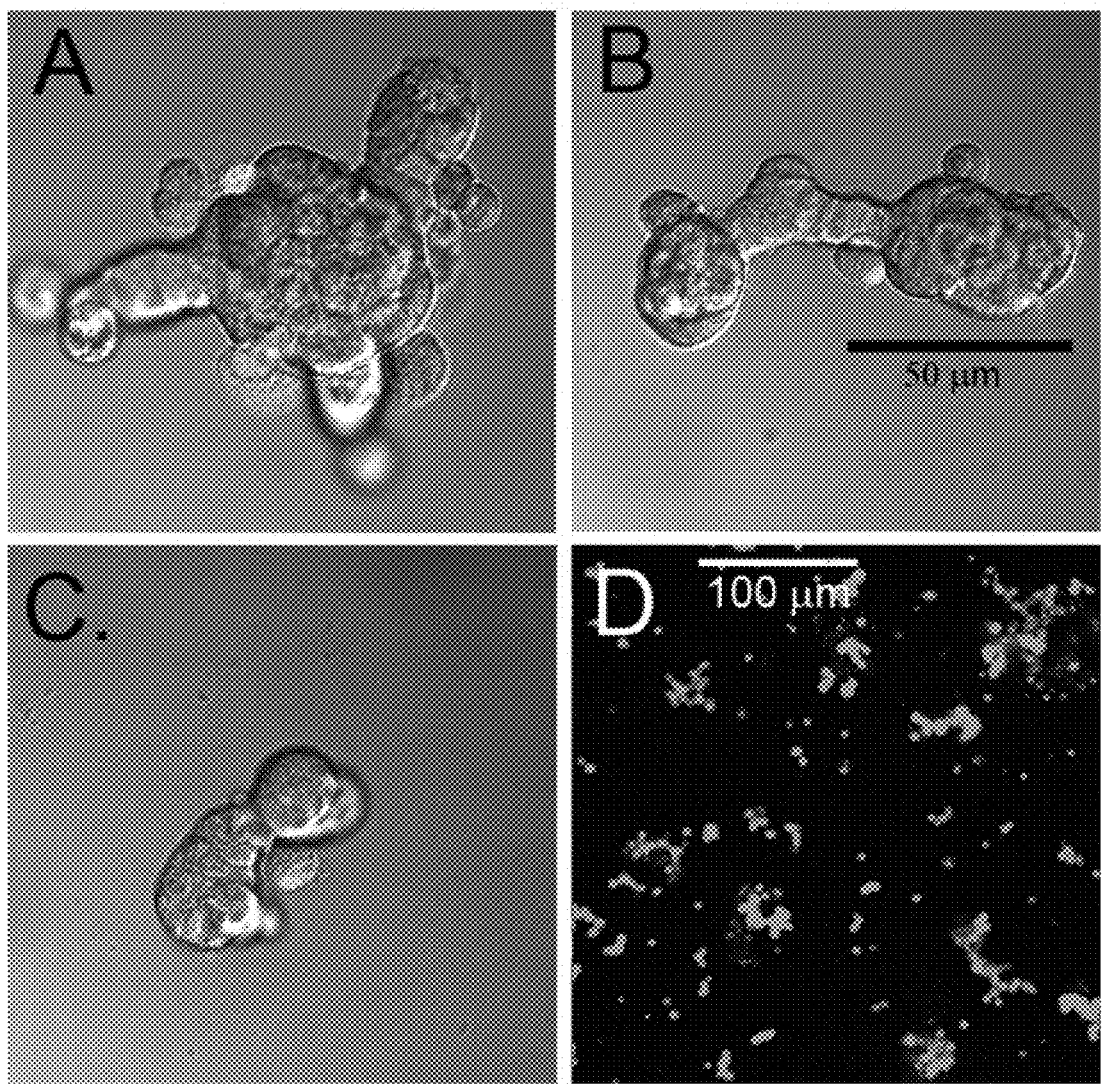
FIG. 6 (panel A) shows the live/dead staining of a small islet cell cluster made from an intact adult islet by enzymatic dispersion. This small islet cell cluster is approximately 40 μm in diameter. In the upper right panel (panel B), a small islet cell cluster derived by cultivating an intact islet with a calcium depleted media is shown. The small islet cell cluster was unwound or opened so that media were able to surround the cells in the cluster. In panel C, a small islet cell cluster derived using both calcium depletion and enzymatic dispersion is shown. The diameter of the fragment was approximately 15 μm. Panel D shows individual islet cells derived from a combination of calcium depletion and enzymatic digestion followed by manual pipetting. The red indicates dead cells, and green cells are alive. Scale bar in panel B applies to Panels A through C.

Cells were stained with dithizone to identify the beta cells within the clusters as generally shown in FIGS. 5 and 6A (enzyme).

Metal-Based Fragmentation.

Intact islets may also be fragmented into small islet cell clusters and individual islet cells using a metal-based fragmentation approach. The interesting finding of metal-based fragmentation is that the resulting small islet cell clusters are less-compact or have an "open" morphology. Cell adhesion molecules, such as E-cadherin, hold the islet together, but require divalent metals to function. See Hauge-Evans et al., Pancreatic beta-cell-to-beta-cell interactions are required for integrated responses to nutrient stimuli: enhanced $Ca^{2+}$ and insulin secretory responses of MIN6 pseudoislets, Diabetes 48(7): 1402-8 (1999). Thus, culturing islets in calcium-free media for about one hour results in a "loosening" and fracturing of the islet structure (see FIG. 6B) in comparison to utilizing enzymes alone, which yields a denser islet structure (see FIG. 6A). Further, after "loosening" the islets using calcium depletion, the remaining clumps of beta cells are more easily dispersed by traditional enzymes (see FIG. 6C).

The details of the metal-based fragmentation are as follows. To obtain individual islet cells and small islet cell clusters, the islets were in calcium-magnesium free HBSS+4.8 mM Hepes. After incubation at about 37° C. for about 30 minutes, the cells were pipetted, dispersing them into small islet cell clusters or single cells. The cells were transferred to CMRL 1066 as the final culture media. When necessary, the small islet cell clusters or beta cells were identified with dithizone. See Mythili et al., Culture prior to transplantation preserves the ultrastructural integrity of monkey pancreatic islets, J. Electron Microsc. (Tokyo) 52(4): 399-405 (2003).

As shown in FIG. 6B, the small islet cell clusters derived by calcium depletion alone had an irregular tubular arrangement, which may be optimal for perfusion of the core of the cluster. In addition, the clusters derived from metal-based dispersion take only about one hour to produce, while the enzyme approach to fragmentation can take up to 48 hours.

Combination of Enzymatic Digestion and Metal Dispersion.

Experiments were also performed using a combination of enzymatic digestion and metal depletion as a dispersion technique. Intact islets were rinsed with 9 ml of HBSS (without calcium or magnesium) with 4.8 mM Hepes. Islets were initially pipetted up and down gently to ensure complete rinsing. Islets were allowed to settle to the bottom of the tube and most of the supernatant was removed. The islets could be repeatedly washed to remove all calcium and magnesium.

A final 9 ml of calcium and magnesium-free HBSS containing 1 ml of papain (50 units/ml) was added to the islets. Islets in the enzyme were rotated slowly (10 rpm) for 30 minutes. At this point small islet clusters could be removed from the solution. Strong pipetting 2-3 times at a moderate speed resulted in single cells.

Cells were centrifuged for 5 minutes at 1500 rcf, 25° C. Single cells were resuspended using the appropriate culture media (depending on the subsequent assays). Cells were stored in an incubator at 37° C. and 5% $CO_2$. As shown in FIG. 6C, combination of the enzyme and calcium depletion method results in a small islet cell clusters or single cells. Moreover, the combination was an overall faster dispersion protocol, but caution must be used to avoid over-digested and damaged cells.

In these experiments, YO-PRO-1 and propidium iodide (Vibrant Apoptotic Assays, Molecular Probes) were used to determine necrotic and apoptotic cells. For the assay, cells were placed with PBS in the Attofluor Chamber (Molecular Probes) on the Olympus Fluoview 300 laser confocal microscope. All images were collected within 20 minutes of removal of the cells from the media. Three simultaneous images were collected for each islet using He:Ne and Argon lasers and a third bright-field image. Live/dead analysis was completed by identifying the cells in the field using transmitted light. Green cells indicate apoptosis, while yellow/red indicates necrotic cell death. Cells lacking fluorescence emission were live. The fluorescence images were overlaid with the transmitted-light image (gray).

Example 3

Figure 7:
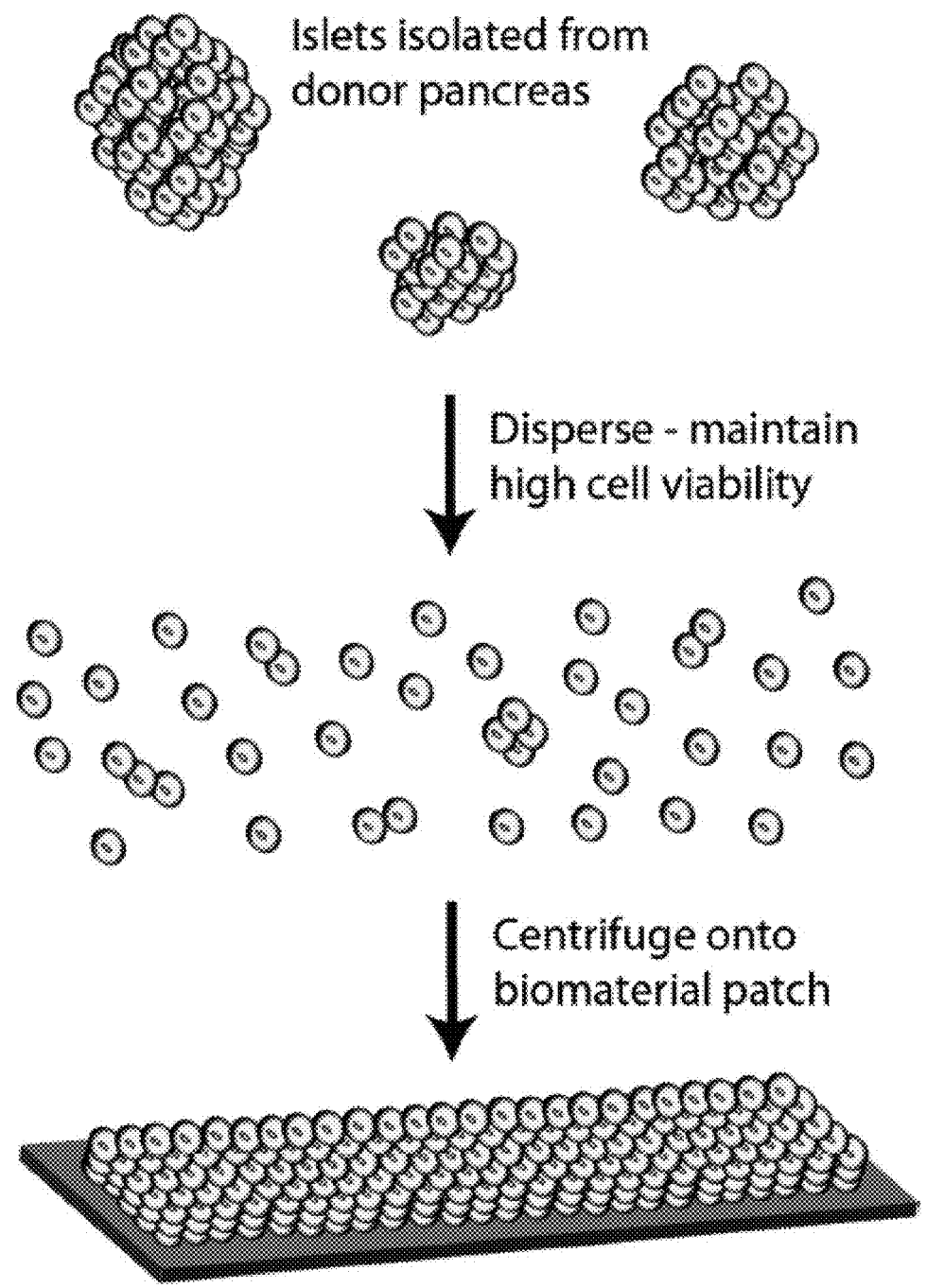
FIG. 7 is a schematic representation of the production of a patch having a multilayer of islet cells attached thereto in accordance with the present invention.

Preparation of Individual Islet Cells and Small Islet Clusters onto a Patch Biomaterial Scaffold The foregoing examples indicate that small islet cell clusters and even individual beta cells should represent the highest achievable free surface area for transporting oxygen, glucose, etc. Thus, in this example, individual islet cells or small islet cell clusters were templated onto a biomaterial scaffold material, such as a patch as generally shown in FIG. 7, to form a multilayer of islet cells.

Screening of Scaffold Materials.

In this example, optimization of various biomaterials useful for preparing the scaffolds of the present invention was investigated by measuring the relative adhesion of the islet cells to the biomaterial. It is preferable that the scaffold material be easy to handle without dissociating the tissue and biomaterial backing to enable facile implantation. Table 1 illustrates a wide variety of biomaterials which were selected for interactions with beta cells. Several of these materials possess a history of use as implants.

In a typical experiment, 1% stock solutions of the listed biomaterials first were prepared. Most materials dissolved in deionized water at neutral pH. Chitosan required a lower pH of about 5.5 to dissolve (hydrochloric acid was used) and other materials required organic solvents; for example Cellform™ in ethanol and poly(DL-lactic-co-glycolic) acid (PLGA) in dichloromethane. Polymers normally soluble in water (e.g. dextran sulfate, alginate, etc.) can be cross-linked to form the film matrix. Approximately 25 µL of each stock solution was added to three individual wells in 96-well plates and left to evaporate or vacuum dried, thus, depositing a thin biomaterial film at the bottom of each well. Residual solvent content is miniscule and did not induce toxicity in cells.

Several proteins offered commercially to promote cell adhesion on well plates (e.g. fibronectin, laminin, etc.) were pre-screened for cell adhesion as well.

A dilute suspension of beta cells was incubated in the 96-well plates overnight and washed three times to remove unbound beta cells. The beta cell suspension was homogeneous and equal aliquots per well were assumed to contain a similar quantity of beta cells. All cell counts were normalized to cell counts from wells that did not include a biomaterial film. In general, mildly hydrophobic polymers performed well for adhering beta cells (Table 1).

TABLE 1

Relative beta cell adhesion of selected biomaterials

| Biomaterial | | Relative cell adhesion |
|---|---|---|
| Empty well (control) | | 1 |
| 50:50 PLGA carboxyl | Mw = 5.5 kDa | 9.8 ± 0.9 |
| Laminin | | 8.7 ± 0.6 |
| Dextran Sulfate | Mw = 500 kDa | 7.4 ± 3.0 |
| 50:50 PLGA-methylester | iv = 0.31 dL/g | 6.8 ± 0.7 |
| Polyvinypyrrolidone | | 5.8 ± 1.2 |
| Dextran Sulfate | MW = 8 kDa | 5.4 ± 1.0 |
| 50:50 PLGA-methylester | iv = 0.9 dL/g | 5.2 ± 0.8 |
| 50:50 PLGA-methylester | iv = 0.58 dL/g | 4.4 ± 0.7 |
| Pluronic | | 4.0 ± 1.5 |
| 50:50 PLGA-carboxyl | iv = 0.12 dL/g | 3.9 ± 0.7 |
| Polyethylenimine | Mw = 25 kDa | 3.8 ± 0.2 |
| Fibronectin | | 3.7 ± 0.7 |
| PEG acrylate | | 3.1 ± 0.5 |
| Chitosan | Mw = 15 kDa | 3.1 ± 0.1 |
| Collagen IV | | 2.9 ± 1.4 |
| PEG | Mw = 8 kDa | 2.8 ± 1.1 |
| Alginate | | 2.4 ± 1.2 |
| Gelatin | | 2.0 ± 0.2 |
| Heparin | | 1.7 ± 0.2 |
| CellformTM | | 1.7 ± 0.7 |
| Chitosan | Mw = 100 kDa | 1.5 ± 0.7 |
| Polyethylenimine | Mw = 800 Da | 1.2 ± 1.0 |
| Polyvinypyrrolidone | | n.d. |
| Poly(vinyl alcohol) | | n.d. |
| Poly(acrylic acid) | | n.d. | iv = inherent viscosity

Cell adhesion was determined by counting the number of attached cells 24 hours after plating on the biomaterial and following three washes. The counts were normalized to the number of cells that attach to a well bottom lacking a biomaterial (see empty well, control) using the following calculation: number of cells attached in the well of interest/number of cells in empty well. Each experiment was repeated in triplicate.

In general, mildly hydrophobic polymers performed well for adhering beta cells. Optical micrographs indicated that cell morphology was also affected by the biomaterial. Beta cells on chitosan (MW=100 kDa) exhibited a smooth, rounded surface while beta cells on laminin demonstrated a spread and ruffled morphology (see FIG. 8). Fluorescent staining of actin in beta cells on the laminin substrate revealed strongly fluorescent cytoskeleton focal points suggesting firm cell adhesion.

Preparation of Islet Cell Patch.

In this example, the islet cells were bound to a biomaterial scaffold patch comprising PLGA. In vascularized islets of Langerhans, the average beta cell is no more than about 25 μm away from a blood vessel. See Wayland, Microcirculation in pancreatic function, Microsc. Res. Tech. 37(5-6): 418-33 (1997). Because beta cells are about 10 μm in diameter, it is anticipated that cell layer thickness of about three cells would most accurately mimic the native beta cell environment.

Figure 9:
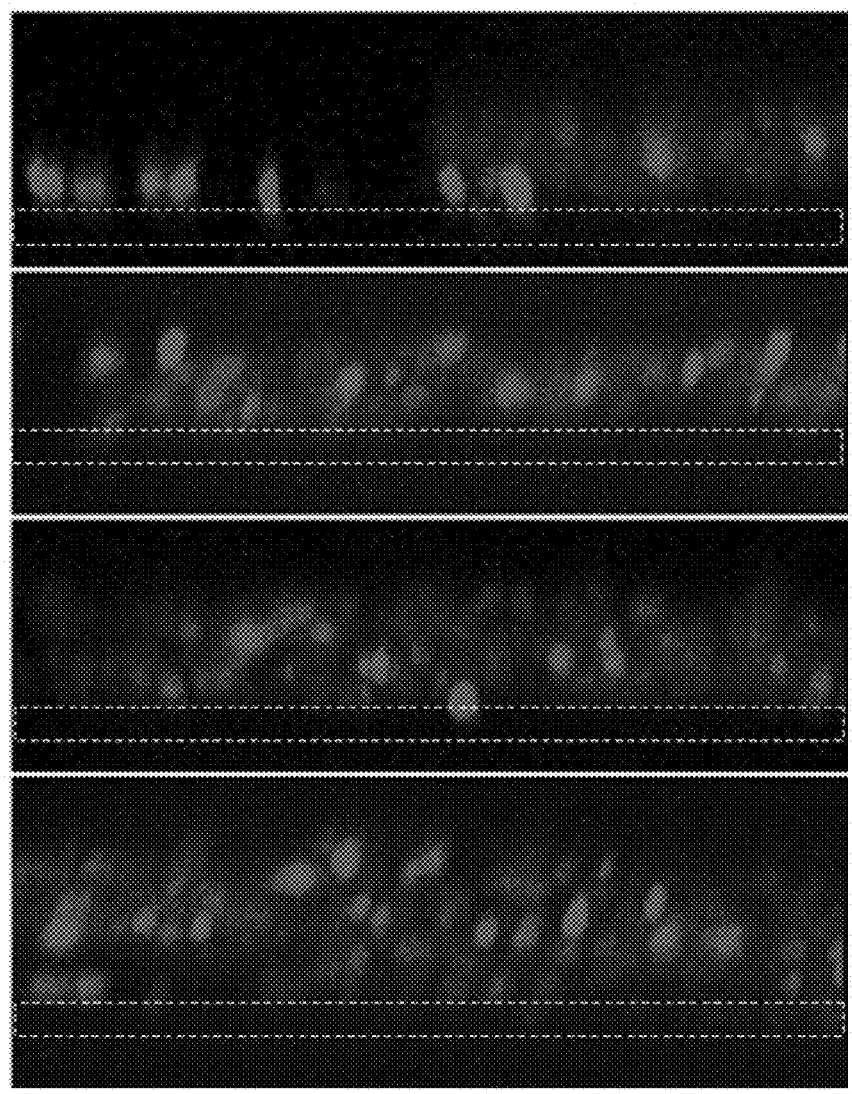
FIG. 9 demonstrates the results when layering islet cells onto a polymer patch made of 50:50 ALGA-carboxyl (5.5 kDa). The patches were optically sectioned using a confocal microscope. The images were rendered to obtain the Z section slice shown. The upper panel illustrates a patch with one or two layers of cells, and additional cell layers were then added, as shown. Cells were layered onto the scaffold by spinning them in a plate centrifuge at about 3500 rpm for about 10 minutes. The layers remained attached to the polymer scaffold after repeated rinsing.

In general, islets were isolated from a rat pancreas and dispersed into single cells or small cell clusters as described previously. Islet cells and small islet cell clusters in HBSS media (0.5 ml) were added to each well and allowed to culture onto the biomaterial for 3 to 4 hours. Plates with biopolymers in the wells were spun in a centrifuge at room temperature at about 3500 rpm for about 10 minutes to assist the cells in attaching to the biopolymer. Half of the media was removed from each well, replaced with media containing a fresh islet cell or small islet cell cluster suspension, and allowed to attach (either by gravity or by centrifugation). This was repeated three times. Results of these experiments are shown FIG. 9. Additional layers of islet cells can be attached to the patch of polymer following repeated washing when the centrifugation method was employed, compared to cells cultured on polymers without centrifugation. About three to five layers of cells remain consistently attached to 50:50 PLGA at 0.58 dL/g (in HFIP) or 0.9 dL/g polymer with repeated media changes. To control the thickness of the beta cell layer, either the volume of cell culture added to each well and/or the number of aliquots added to each well in repeated deposition cycle can be controlled.

Example 4

Prophetic Testing of islet Cells on Biomaterial Scaffold

In this example, biomaterial patches having a multilayer of islet cells attached thereto will be further investigated. Viability measures and insulin production assays will be performed. In addition the device will be investigated as an implantable device for the treatment of diabetes.

Viability Measurements.

Apoptosis versus necrosis experiments will be completed as previously. The percentage live cells will be calculated per cross sectional area of the beta cell layers for comparison to native islets on days 0, 1, 3, 7, 14, and 30 for three samples. Data will be plotted as percent viable cells versus time and it will be determined if a statistically significant difference exists between the viability trends for different numbers of beta cell layers using a t-test. In addition, recording of the percentage of cell death attributed to necrosis or apoptosis will be made.

Insulin Production Assays.

Insulin production will be measured using static incubation (ELISA) under conditions of low glucose (3 mM), high glucose (30 mM), and high glucose/depolarization (25 mM K$^+$) (Dean 1989). Each well in 12-well plates will be preincubated with fresh media at 37° C. and 5% $CO_2$. For experimental measurement, the various beta cell patches will be incubated for 2 hours in fresh media containing either 3 or 30 mM glucose. One additional group of wells is incubated in 30 mM glucose, containing 25 mM KCl with appropriately reduced NaCl. Each patch type will be evaluated in triplicate for each condition tested. Media samples will be assayed for insulin content using an ELISA immunoassay. The results will be expressed as averages of the triplicate samples with standard deviation and compared using a t-test for statistical significance. MacGregor et al., Small rat islets are superior to large islets in in vitro function and in transplantation outcomes, Am. J. Physiol. Endocrinol. Metab. 290(5); E771-779 (2006).

Implantation of Patches and Islets.

Diabetes will be induced in adult recipient Diabetes Resistant BioBreeding (DRBB) Worcester rat is a model of autoimmune diabetes that parallels type I diabetes in humans. Four-week old rats will be purchased from Biomedical Research Models, Inc. Animals will be randomly divided into 2 groups: patch recipients and islet recipients (6 per group). For the induction of diabetes the DRBB rats will be treated with a combination of anti-RT6 monoclonal antibody (DS4.23 hybridoma (kindly provided by Dr. Dale L. Greiner, University of Massachusetts Medical Center; 2 ml tissue culture medium injected 5 times/week) and non-specific immune system activator poly I:C (Sigma; 5 ug/g of body weight injected 3 times/week). The injections will be given over a 3-week period. On the date of repeated hyperglycemia (blood glucose levels >250 mg/dl for 3 consecutive days), the animals will be considered diabetic and the treatment discontinued (Semis, 2004). With this method, 95% of the rats become diabetic by the end of the 3rd week. Implantation of beta cell patches and islets will be done in the kidney subcapsule. DA (Dark Agouti) rats will serve as beta cell donors. Rats will be anesthetized with pentobarbital (45 mg/kg) and the kidney delivered to an incision made in the body wall on the left flank. A moderate incision will be made in the kidney capsule, and the beta cell patch placed under the capsule. A minimum of 4 patches with variable biomaterial and/or cell layer thickness will be implanted. Islet implants typically require a smaller incision and infusion through a small bore pipette. Recipient groups will receive either 1000 or 2000 IE of islets for transplants or an equivalency of beta cells on the patch substrate. Significant improvement in performance (patch type versus islets) should be detectable if the minimum necessary islets for success (1000 IE) are transplanted and compared to a higher islet volume (2000 IE). Beef/porcine zinc-insulin (NPH Iletin I) injections (2 times/day) will be given for 3 days post-islet transplant to reduce the stress of hyperglycemia.

In Vivo Determination of Glycemia.

The blood glucose of rats will be monitored for 4 weeks to determine whether the patch or islet implants can induce euglycemia. The glycemic control of the animals will be followed by taking blood glucose measurements daily. Plasma glucose levels will be monitored by obtaining blood samples from the tail on a daily basis for the first 3 weeks, and then 2 times/week using the Freestyle glucose meter (TheraSense). Generally reversal of diabetes is achieved within 24 hours of islet transplantation, similar outcomes should be achieved with the patches.

Analysis of explanted beta cell patches. The patches or islets will be retrieved after 14 or 30 days for immunostaining (insulin and glucagon), viability measurement, and detection of apoptosis. In some cases, rats achieving euglycemia will be maintained for 8 weeks before analysis. Immunohistochemistry on the sections will be completed using antibodies for insulin and glucagon. Images will be processed using colorimetric analysis to determine the cross-sectional area positive for each of the stains. Negative control slides will be prepared and analyzed. Initially, a dithizone stain a dithizone stain will be used to identify beta cells. DNA-fragmentation, indicative of cellular apoptosis, will be completed using terminal deoxynucleotidyl transferase (TdT)-mediated dUTP nick-end labeling (TUNEL) assay. Patches or islets will be prepared for histology using 10% formalin embedded in paraffin as we have previously done. A TUNEL kit (In Situ Cell Death Detection Kit, Roche Diagnostics) will be used to label the histological sections. The patches and islets will be analyzed both for the number and distribution of TUNEL+ cells by a blinded researcher. Images of histological sections will be reconstructed into full 3D images of islets. In this way, apoptotic cells throughout single islets can be identified. Sections will be counterstained with hematoxylin and visualized under the light microscope. To identify the insulin-secreting cells within the islets, anti-insulin antibody will be used to label samples and detected with a rhodamine secondary antibody. We anticipate collecting a minimum of 10 islets/rat post transplantation for apoptosis analysis. Negative control slides will be prepared as necessary. In addition to TUNEL analysis, patches will be fixed for subsequent electron microscopy using the core microscopy facility. Identification of beta cell layers and of infiltrating cells will be conducted in this manner.

Example 5

Preparation of Optimally Sized Cells Using a Micro-Mold

In this Example, an additional device for reaggregating cells was developed and designed, and methods for generating a micro-mold having multiple individual divots etched into the surface of substrate are described.

In general, a pancreas may be broken down into native large islets (greater than 150 µm) and native small islets (less than 125 µm). Large and small islets are separated, and small islets are placed in culture (in some embodiments the small islet culture will later be added back to the newly reaggregated islets.) The large native islets are dispersed into single cell suspension and allowed to settle into the micro-mold. The size of the produced islet can be manipulated by the number of cells loaded into the micro-mold. Depending on the cell suspension, typically 20-100 (+/−20%) cells will fall into each divot to bind to each other, forming a new reaggregated small islet. The single cells in individual divots are cultured under conditions to promote formation of the 3D structure that resembles the native small islet wherein the size and shape of reaggregated islets are influenced by the size and shape of the divot. Ability to vary the number of cells in the divots by concentration (by determining the cell density in suspension) allows us to produce a very small (under 30 µm) or mid-sized (50-90 µm) reaggregated islet. This control may turn out to be important when forming other 3D cellular structures like the mini-tumors for chemotherapy testing.

Unlike the biomaterial scaffold patch of Example 3 supra, the divoted micro-mold described in this example does not require cells to attach to the substrate surface. As discussed below, islet cells reaggregated in a micro-mold are optimally sized, viable, and cell populations derived from micro-molds are characterized by high percentage viability and high levels of insulin secretion.

Development of Micro-Molds.

Divots as the physical reaggregation environment. In an effort to reaggregate single cells into optimally sized small islets, we hypothesized that forming the islets in a physically constrained environment would guide the shape of the cell mass during reaggregation. To this end, we determined that an optimal physical reaggregation environment would be similar to both the shape and size of the desired cellular end product. The dimension range used in our first experiments (100 µm diameter and 60 µm depth) is optimal for production of reaggregated islets under 50 µm in diameter (on average). The 60 µm depth allows easy retrieval of the reaggregated islets without breaking them into smaller pieces. A rounded bottom in each reaggregation environment guided reaggregation of the cell mass into a roughly spherical shape. We refer to these physical reaggregation environments with specified dimensions including rounded bottoms as "divots." The dimensions and placement of the divots can be varied according to the needs of the user.

Micro-Mold Design.

Figure 10:
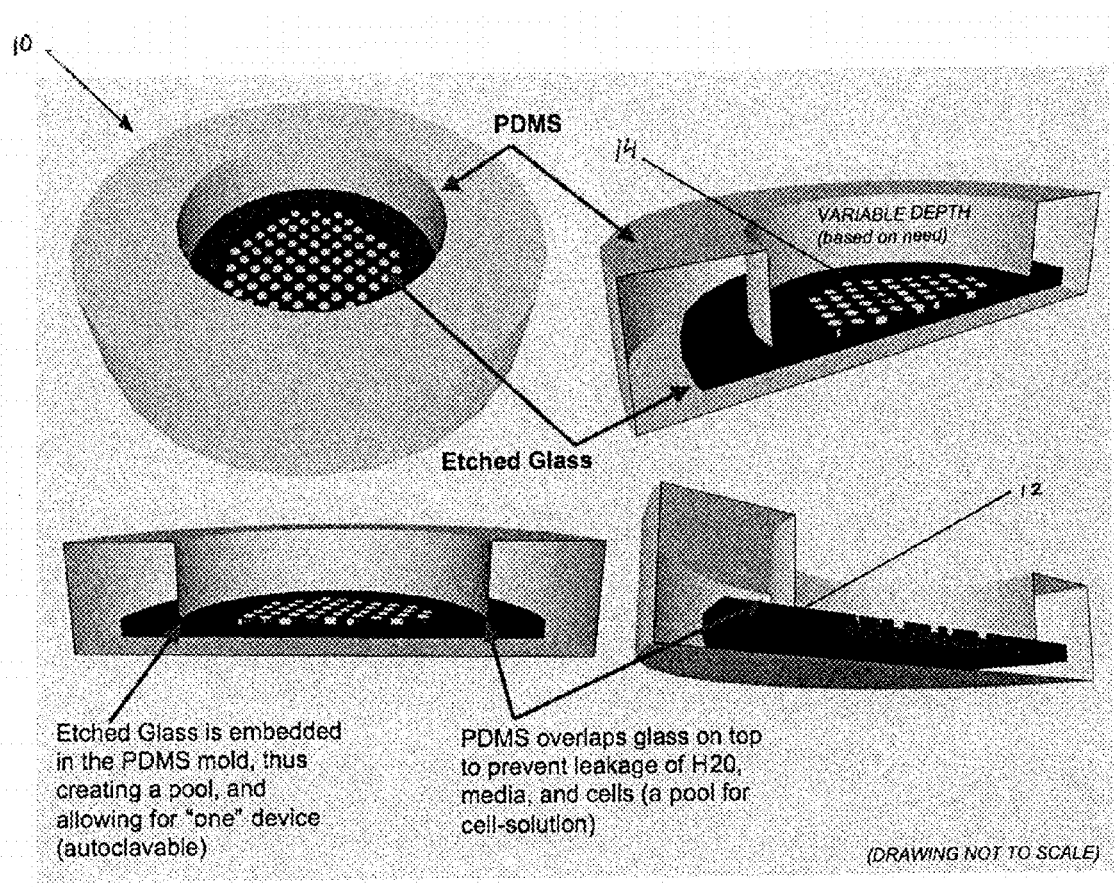
FIG. 10 is a schematic depicting the general design of a micro-mold with divots. In this example, PDMS is the material comprising the housing of the micro-mold and etched glass is the substrate in which the divots are etched.

In an effort to generate populations of optimally sized small islets, we designed, with reference to FIG. 10, a micro-mold substrate 10 containing a surface 12 comprising numerous divots 14. AutoCAD software (available from Autodesk, Inc., San Rafael, Calif.) was used to create electronic templates of the micro-molds 10. The template delineates the size, shape and distribution of divots 14 on the mold surface. The divoted substrate 10 may be set within a larger housing capable of containing liquids without leakage also referred to herein as the mold housing (FIG. 10). The dimensions of both the micro-mold 10 and divots 14 within the micro-mold can be varied according to the needs of the user. For example, if the goal were to use the micro-molds 10 for drug testing, a larger and/or deeper divot 14 might be tested so as to hold a larger volume of tested compound per divot. If the cells of interest were not islets, the dimensions of the divot could be specified otherwise to meet the optimal reaggregation or growth criteria for the cell type of interest.

Substrate for Divoted Surface.

There are several physical properties that are important when choosing a substrate. Using a silicone dioxide ($SiO_2$) based substance is preferable for wet etching with a buffered hydrofluoric (HF) acid solution. HF acid etches a substrate by reacting with the $SiO_2$ molecules. In addition, for the in vitro use of the micro-mold, it is preferable to choose a substrate to which cells would not adhere, allowing easier removal of reaggregated islets from divots. A transparent substrate allows for viewing contents within divots under a microscope without having to transfer to another plate. A sterilizable substrate provides for a reusable mold. Glass was the chosen as one possible substrate for the non-implantable micro-molds, as it exhibits all of these characteristics. In addition, users can specify the thickness and dimensions of glass during manufacturing allowing for further customization of micro-molds. Glass also provides a low-cost solution; however, this material may not be implantable. Plastics and moldable gels can also be used for the mold substrates.

For developing the mold housing, several properties in the substrate are necessary. The material chosen to build the mold housing should have the ability to be molded according to user specifications. This means it starts out as a liquid that can be poured into a mold and will set with time and temperature to form a solid feature surrounding the etched substrate. The polymer is preferably sterilizable. The polymer may be hydrophobic to help prevent liquids from leaking out of the molds. Sylgard 184 Polydimethylsiloxane (PDMS; Dow Corning, Elizabethtown, Ky.) is one possible polymer that may be used for these molds. PDMS can be sterilized, is hydrophobic, can be easily poured in a mold and cured to a solid product. In addition, PDMS can be used in temperatures ranging from −45 to 200° C. over a long period of time, allowing for both freezing and steam-sterilization. PDMS has a working time of about 2 hours and can then be cured at room temperature (~48 hrs) or heat-cured (up to roughly 200° C.). PDMS mixed to manufacture specifications has the ability to stick to the glass substrate, further protecting from leakage of liquids in the mold (Mata et al., 2005). Micro-molds designed with glass and PDMS were specifically designed for in vitro experimentation and are not suited for in vivo use. Implantable molds that would be used for in vivo purposes are described below that do not use photolithography, but rather are produced by first making a negative stamp.

The micro-mold prototypes generated include glass substrates in which divots were etched. The divot substrate can be cut to meet the needs of the user. For example, the substrate might be cut to the size of a standard microscope slide. In one prototype created, the soda-lime glass substrate was cut circularly to 33 mm diameter and 3 mm thick.

Preparation of Substrate Surface.

The surface of the substrate to be divoted was cleaned with nitrogen gas to remove large particles. Acid and base piranha solutions were used to deep clean the substrate to remove organic compounds and matter that could interfere with metal deposition and photolithography. Subsequently, the substrate was baked for 30-60 minutes. Other methods to remove large particles and organic compounds from surface substrates can be employed by a skilled artisan. Once the substrate surface was clean, a layer of metal (300 nm chromium) was sputtered on to the substrate using a Lesker Thin Film Deposition System (available from K. J. Lesker, Co., Clairton, Pa.). Alternative techniques for applying thin metal layers to substrates are known in the art and can be utilized.

Photolithography.

Figure 11:
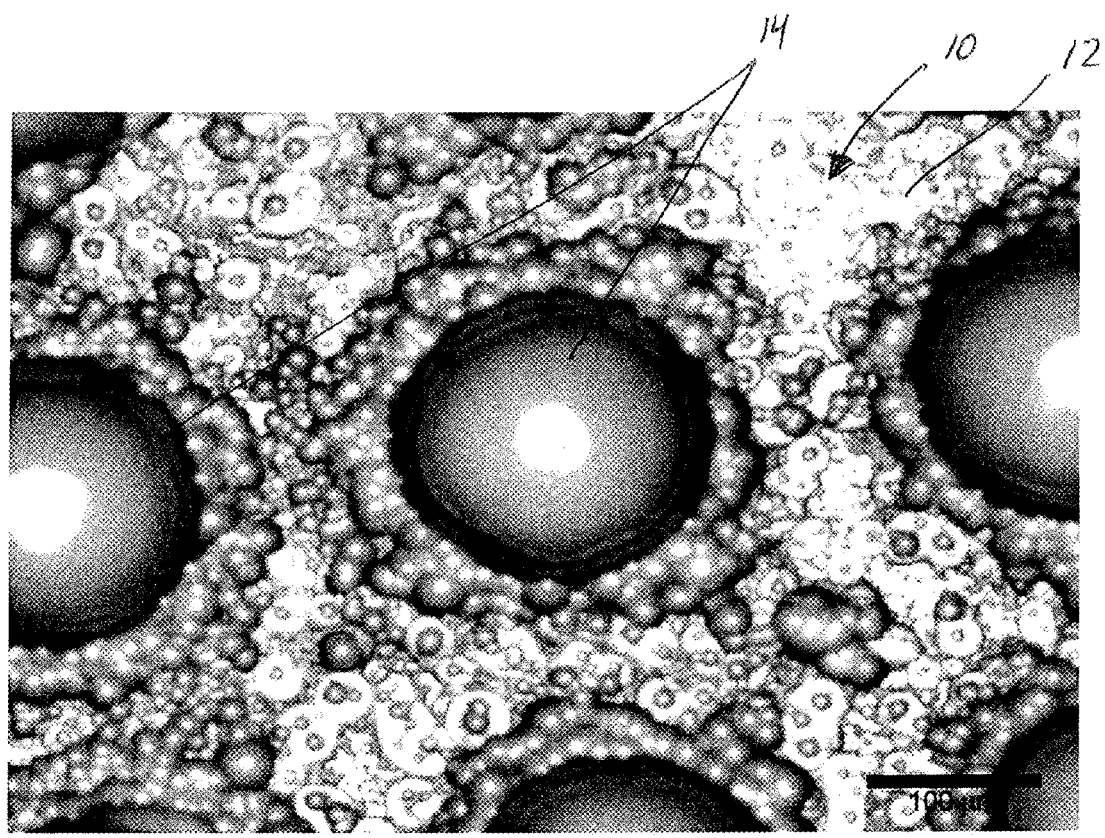
FIG. 11 is a micrograph showing a top-down view of empty divots in a micro-mold; the pattern of divots depicted here is representative of micro-mold design B.

A coat of AZ1518 Positive Photoresist (1 ml) was applied to the top of the deposited metal using a Brewer CEE100 Programmable Spin Coater (Brewer Science, Rolla, Mo.). The spin coater was set to yield a 1.8 micron layer of photoresist, followed by a soft bake at 100° C. for 2 minutes. After cooling, the glass with the photomask was exposed to UV light from a UV Flood & Mask Alignment System (ABM, Scotts Valley, Calif.) for 4 seconds followed by immersion in an AZ 300 MIF Developer (AZ Electronic Materials, Branchburg, N.J.) for 30 seconds. The substrate was agitated slightly and then baked at 100° C. for 8-10 minutes. The developed pattern in the photoresist was subsequently etched into the chromium layer by immersing it in an CR7S Chromium Etchant (Cyantek Corp., Fremont, Calif.) with agitation to aid in the etching process. About 30-45 seconds of immersion is required for the image to appear. The substrate was washed lightly with water and dried with nitrogen to prepare for the wet etching process. This produced a piece of glass layered with chromium and photoresist that contained open spots on the surface where chromium or photoresist were not present. These unmasked spots expose the glass surface to the wet etching process, while areas covered with chromium and photoresist protect the glass surface from the etching solution. This leads to etching of divots in the unmasked areas. Wet etching was completed in a solution of HF:HNO3:H20 at a ratio of 20:14:66, respectively. The substrate was immersed in solution for 18 minutes while on an orbital shaker at low speed. During immersion, the acid attacked the glass by reacting with $SiO_2$, thus dissolving visible portions of the glass that were not covered with the chromium and photoresist masks, creating uniform divots 14 on the surface 12 (FIG. 11). This solution yields an approximate etching rate of 4 to 5 μm of depth per minute (dependent on freshness of solution). Agitation on an orbital shaker ensures uniform etching of surface.

Figure 12:
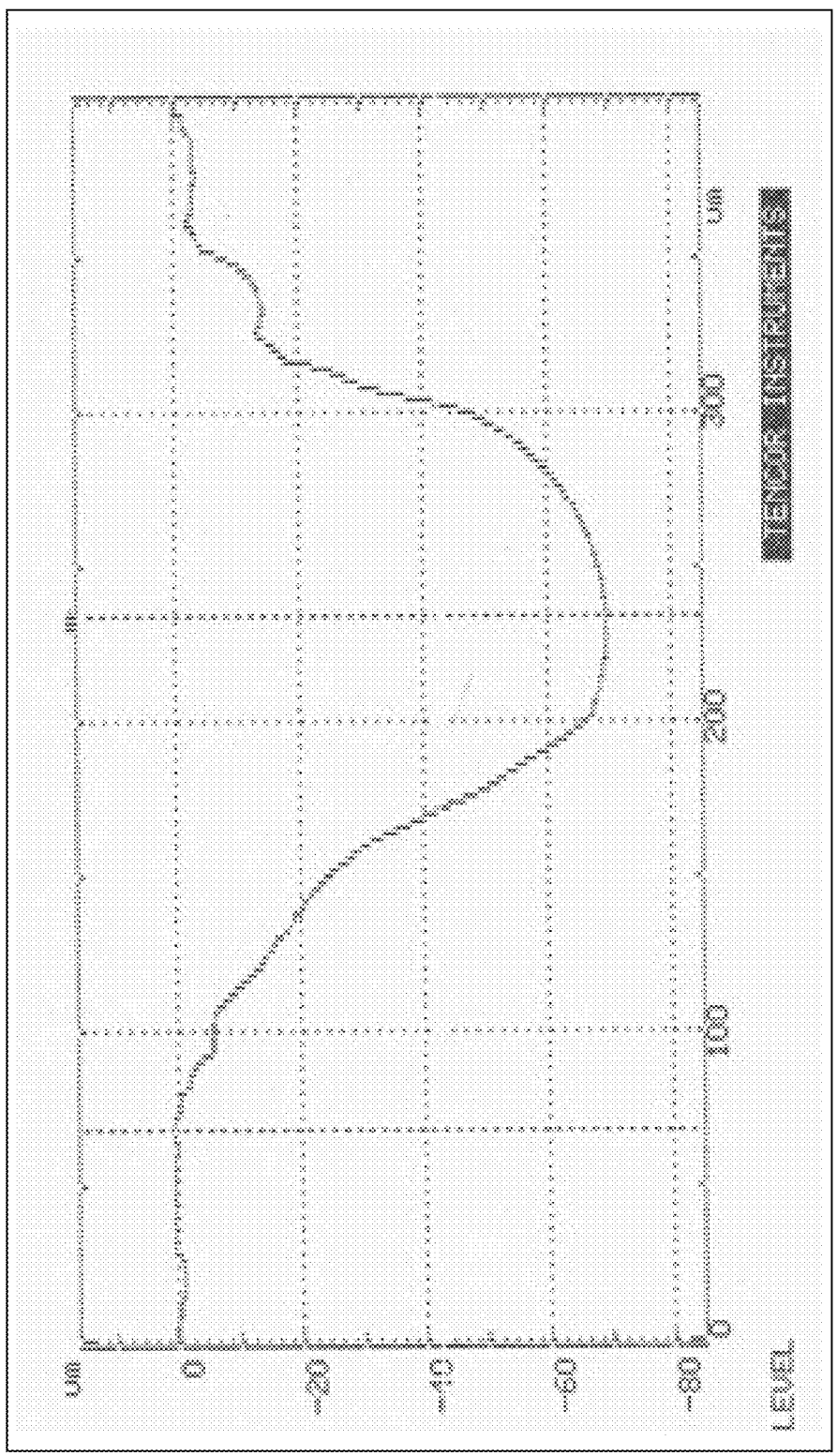
FIG. 12 is a graph generated by a profilometer illustrating the depth of a single divot and the round bottom shape of the divot.

The substrate was subsequently washed in calcium carbonate and then water to neutralize and remove the excess acid, and finally dried with nitrogen. If excess chromium remained on the substrate, additional immersion in Chromium Etchant and washing with acetone and water to remove any remains is required. Finally, the substrate was dried with nitrogen. Divot depth and diameter was measured using a profilometer (FIG. 12). In the prototypes created, variability in the divot size has not been problematic; prototype divots measured +/−10% of specified dimensions.

Figure 27:
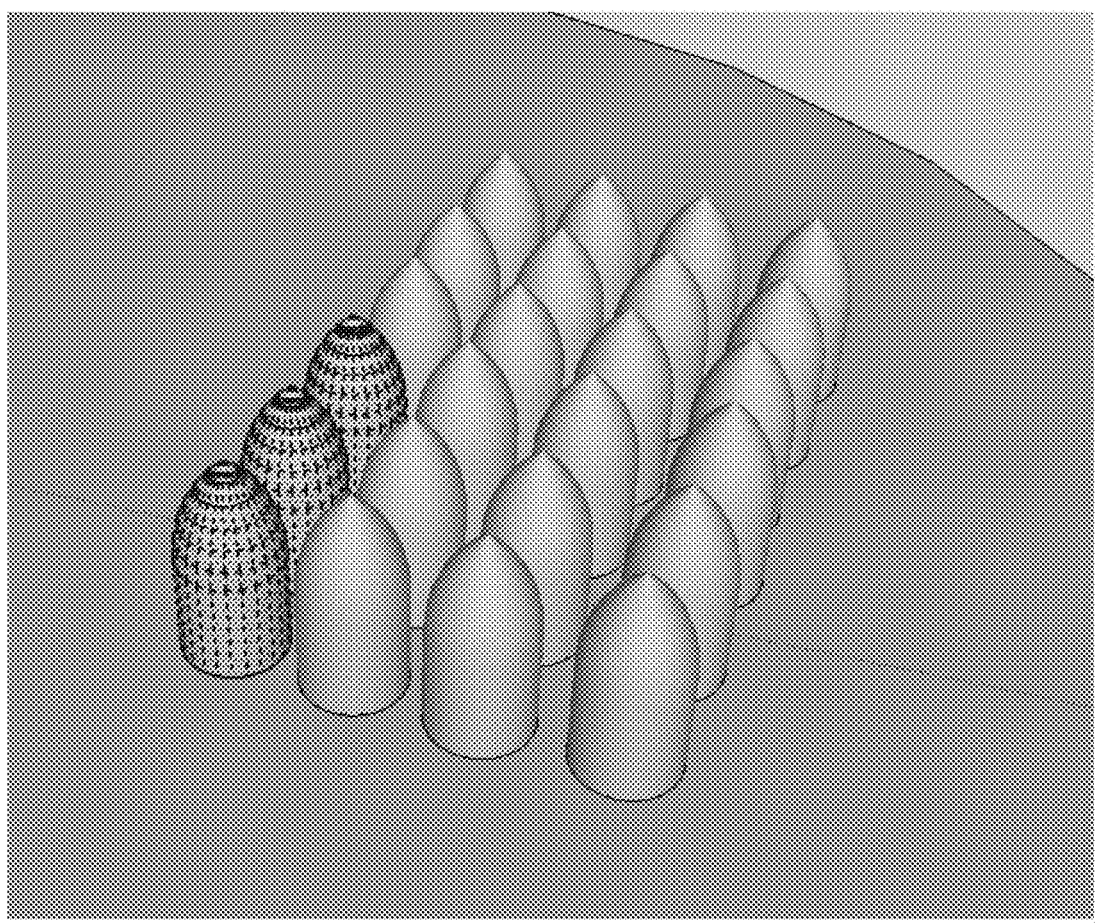
FIG. 27 shows a design for the negative stamp (made of metal or SU-8) that could be used to create the biopolymer molds. The final product would have divots similar to those created in glass molds.
Figure 28:
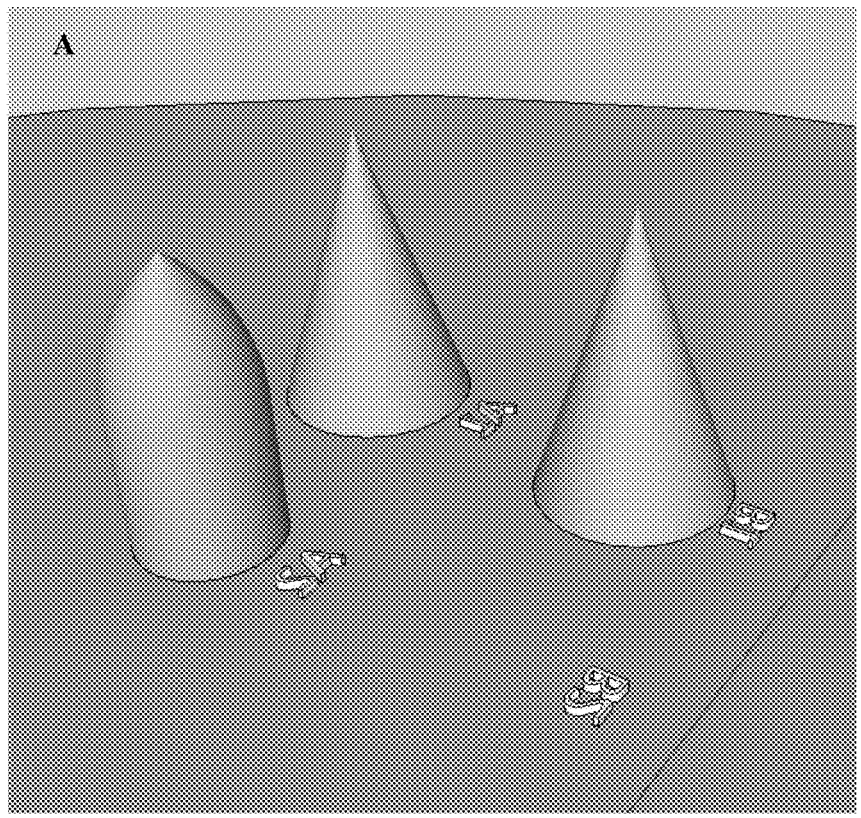
FIGS. 28 A and B illustrates the negative stamp design including labels to identify the location of each divot within a field of divots in each micro-mold.
Figure 28:
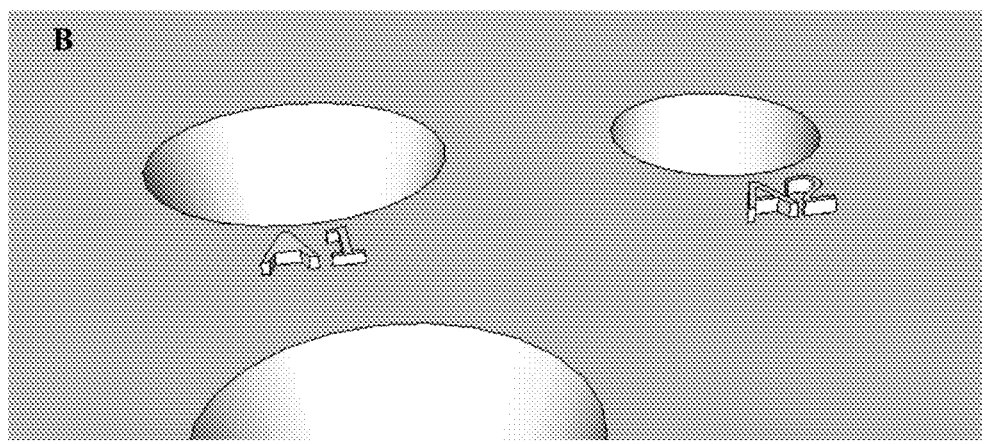

We envision two other prophetic methods that may be used to create molds:

SU-8 Negative Molds: In this embodiment, glass will be used again as the substrate. The glass undergoes a similar photolithography process as before, but the original design is altered to create a negative template mold (FIGS. 27-28), that can then be converted to a micro-mold, but pouring one of the listed biopolymers onto the stamp and allowing it to cure. Briefly, SU-8 photoresist is spin coated in a thick layer (thickness of layer should be equal to desired depth of divots). It is then soft baked, covered with a photomask (as described above) and exposed to UV light, baked again post-exposure, developed in an SU-8 developer, and finally exposed to a post-development bake. This yields a piece of glass that has negative projections of divots based on design specifications. This negative template will then be used to cast molds in a given biopolymer or PDMS by creating a mold imprint upon curing. The stamp will then be removed from the cured polymer. The finished polymer will resemble the PDMS/glass micro-molds and will have divots of defined dimensions. One advantage of this procedure is that for drug testing or other applications, each divot can be labeled during the design step with a unique identifier (e.g., text, numbers), and will be present in the finished molds as visible imprints by each divot (see FIG. 28). A more detailed process is described in the manufacturer's processing guidelines (SU-8 2000—Permanent Epoxy Negative Photoresist, MicroChem, Newton, Mass.).

Etched Metal Mold Negatives.

In this embodiment, polymer molds would be created using a metal casting mold. The metal casting may be manufactured by designing a 3D model in CAD software. One possible design is provided in FIG. 27. The metal is laser-etched to create a casting mold similar to the SU-8 molds described above. Polymer is poured over the metal casting and cured to create a new micro-mold. Again, if necessary, text or numbers can be incorporated into the 3D model to label each divot as above, leaving a visible imprint.

The SU-8 and Etched Metal templates were conceptualized to allow a method for producing molds from a given material for both in vitro and in vivo use. More specifically, these methods can utilize biopolymers to create molds that can be implanted. These methods should also allow for more detailed designs (such as divot labels) and more control in divot creation, shape and size (variability of divot measurements should be less than +/−1% of specified dimensions).

Construction of Housing for Divoted Substrates.

The next step in constructing the micro-mold is developing a system in which the divoted surface will be placed and secured, and which will serve as a larger vessel for culturing (see PDMS "housing" in FIG. 10).

Figure 13:
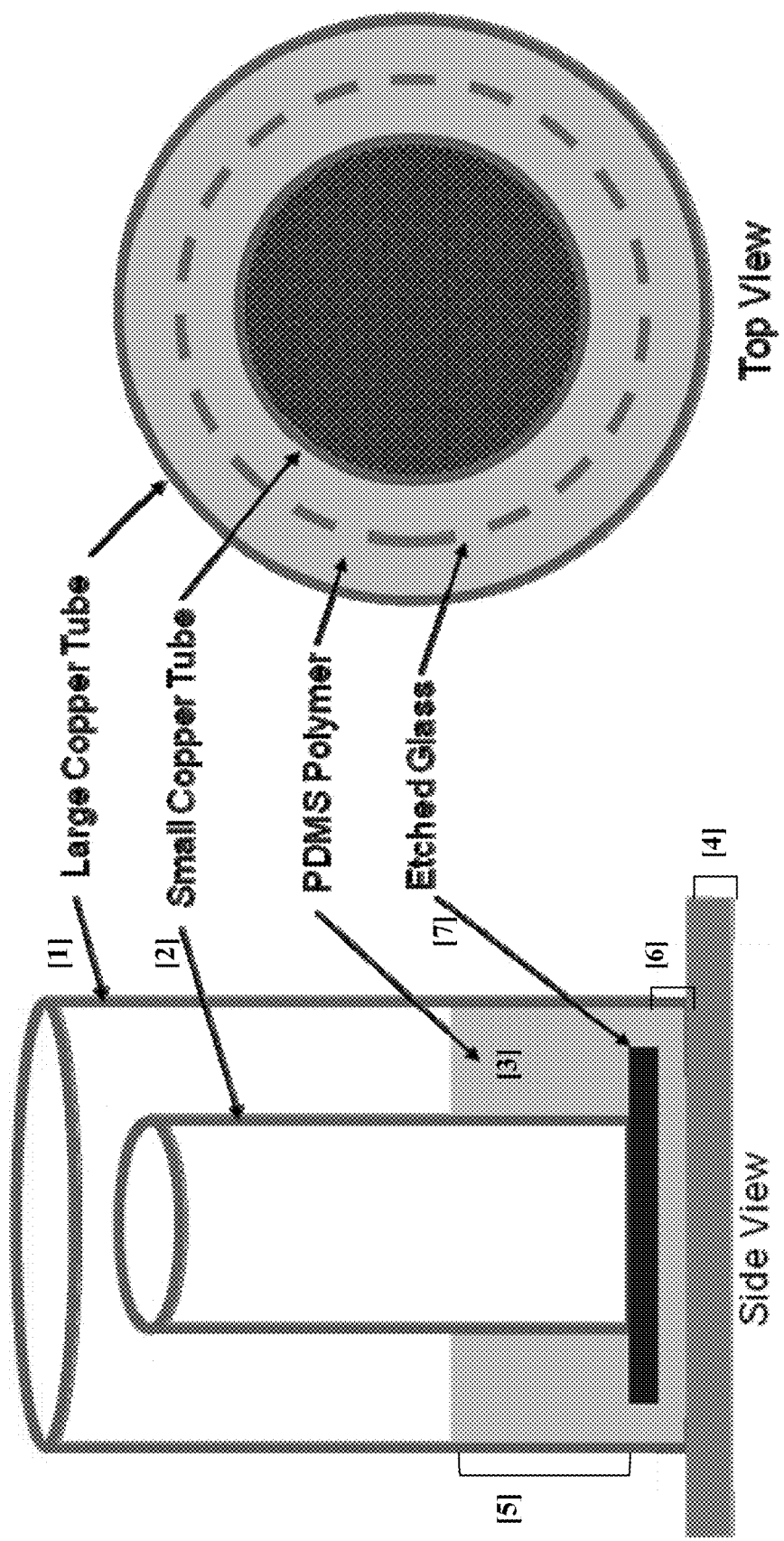
FIG. 13 is a schematic illustrating the scaffolding utilized for micro-mold production. Components of the micro-mold and scaffolding to build the micro-mold are: [1] a large copper tube; [2] a small copper tube; [3] PDMS polymer, which comprises the system that houses the divoted surface; [4] a flat surface, such as a large square of glass wrapped in aluminum foil, used as a base upon which to build the micro-mold; [5] the vertical walls of the micro-mold housing; [6] the base of the micro-mold, shown here poured to a depth of 2 mm; and [7] the etched glass, which is the divoted substrate.

The base [6] and vertical walls [5] of the mold housing were built using Sylgard 184 Polydimethylsiloxane (PDMS) (FIG. 13). PDMS was mixed at a ratio of 10 parts base to 1 part curing agent in a 50 ml centrifuge tube (~2 hr working time). The tube was mixed well to thoroughly disperse the base and curing agent. A vortex can be used to aid in mixing during this process. The PDMS was centrifuged at 1000-1500 rpm for 1 minute to remove air bubbles. Materials other than PDMS can be used to construct suitable housing for the micro-mold. For example, materials appropriate for a micro-mold meant for multi-use in vitro applications include, but are not limited to, those that may be implanted (in vivo use). Micro-molds meant for in vivo use may be formed with both the divoted surface and the sides of the mold from biopolymers. However, the height of the sides will be minimal, and may be removed prior to transplantation to decrease the total volume of transplanted material.

Materials appropriate for a micro-mold purposed for in vivo applications include, but are not limited to poly(orthoesters), poly(anhydrides), poly(phosphoesters), poly(phosphazenes), and others. Other non-limiting materials include, for example, polysaccharides, polyesters (such as poly(lactic acid), poly(L-lysine), poly(glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), copolymers of these monomers and the like), poly(anhydride-co-imides), poly(amides), poly(ortho esters), poly(iminocarbonates), poly(urethanes), poly(organophasphazenes), poly(phosphates), poly(ethylene vinyl acetate), and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, copolymers, polystyrene, and blends or co-polymers thereof). In certain preferred aspects, the biomaterials include polysaccharides, alginate, hydroxypropyl cellulose (HPC), Nisopropylacrylamide (NIPA), polyethylene glycol, polyvinyl alcohol (PVA), polyethylenimine, chitosan (CS), chitin, dextran sulfate, heparin, chondroitin sulfate, gelatin, etc., and their derivatives, co-polymers, and mixtures thereof. Other suitable biomaterials include those nylon, hyaluronan, polytetrafluoroethylene, polyvinyl formamide, and others described in Vats et al., 2003; Wang et al., 1997; and Orive et al., 2003.

The shape of the mold housing was formed using a copper scaffold (FIG. 13). One large copper tube (1.75 inch diameter) [1], was placed, open side down, on a flat surface [4] (e.g., large square of glass wrapped in aluminum foil). PDMS was added to the center of the tube opening to a depth of 2 mm to form the base of the mold housing [6]. The entire structure was then baked for 45 minutes at 100° C. in an oven. Following baking, the divoted substrate was placed, divot side up, in the center of the copper tube (hashed line depicts location of etched glass [4] relative to large copper tube) on top of the cured PDMS base [6].

A small amount of PDMS was added to the edges of the divoted substrate to fix it in the center of the cured PDMS base [6]. The structure was then baked for 30 minutes at 100° C. A small copper tube [2] (1 inch diameter was centered on top of the etched substrate and PDMS was poured into the space between the large [1] and small [2] copper tubes. This step was done carefully to avoid spilling the PDMS into the center of the mold. The amount of PDMS poured into the space between the large [1] and small [2] copper tubes determines the height of the mold housing [5]. The height and width of the mold housing can be specified by the user. The micro-mold, including the copper housing scaffold, was then baked overnight (at least 12 hrs) at 100° C. to fully cure the PDMS.

Following overnight baking, the copper scaffold setup was removed as follows. The entire structure [1-7] was cooled to shrink the PDMS, allowing removal of the mold from the copper tube scaffold. The exact time needed for cooling is dependent on temperature; 30-60 minutes at −20° C. is sufficient. The bottom foil/glass layer [4] and small copper tube [2] were removed carefully. Next, the large copper tube [1] was separated from the micro-mold.

Sterilization of the Micro-Mold.

Preferably, a divot-containing surface of the present invention is capable being sterilized. In one embodiment, when the finished micro-mold is free of scaffolding, it can be washed and sterilized as necessary for use. Ethanol and steam sterilization are the preferred methods of sterilization, but other methods of sterilization known to the skilled artisan are suitable. When using PDMS in the micro-mold, acetone should not be used. Likewise, sterilization procedures that will compromise the integrity of the materials used in the divoted substrate or the mold housing should not be used. Sterilization allows the micro-mold to be used repeatedly for in vitro use.

Cell Reaggregation within Micro-Molds.

Single dispersed islet cells used to reaggregate the islets can be obtained from any source of islet cells. In this example, an animal pancreas was cannulated in situ via the common bile duct, and distended by pumping a cold solution of collagenase (Worthington, Lakewood, N.J.) into the duct. Subsequently, the distended pancreas was excised, transferred to centrifuge tubes, and incubated for 30 min with gentle rotation at 37° C. The washed digest was then passed through a screen and sedimented in a refrigerated centrifuge. The resulting pellet was mixed with Histopaque (density 1.1085 g/ml, Sigma Diagnostics, St. Louis, Mo.) and centrifuged. Islets were then cleaned of exocrine tissue by filtering through a 40μ screen with Hanks Balanced Salt Solution (HBSS) with 5% bovine calf serum, and placed into Petri dishes containing DMEM/F12 culture medium, 10% fetal bovine serum (FBS), EGF (20 ng/mL) and 1% antibiotics. The islets were maintained overnight at 37° C. with 5% CO2.

To disperse islets into single cells, isolated islets were digested to viable cell suspensions by placing them in a 50 ml centrifuge tube, centrifuging and transferring the pellet to a 1.5 ml microcentrifuge tube. After two washes with calcium-magnesium free HBSS, a mixture of nine parts calcium-magnesium free HBSS and 1 part papain (5 U ml final concentration) was added. After incubation on a rotator at 37° C. for 20 min, the islets were pipetted, dispersing them into single cells.

Incubation of Cells in Micro-Molds.

Single-dispersed cells were transferred to the micro-molds in specialized Aggregate Media (DMEM/F12 culture medium, with 10% fetal bovine serum (FBS), EGF (20 ng/mL), ITS (1 g/L), BSA (2 g/L), Nicotinamide (10 nmol/L), Exendin-4 (5 nmol/L) and 1% antibiotics) (Kikugawa et al., 2009) for final culture. To this Aggregate Media, we have added high calcium conditions (2-4 mM), which enhances islet reaggregation. At the time of dispersion, an aliquot of cells are microscopically examined using a hemocytometer. The percentage of single cells versus doublets or triplets is determined. A successful cell dispersion is defined as having a minimum of 90% viable single cells with the other 10% comprising doublets and triplets. By knowing the density of cells in the dispersion via the cell count using the hemocytometer, we are able to estimate the number of cells per divot. However, we have also counted the cells/divot once the micro-molds have been loaded, which varied from experiment to experiment, based on the media cell density, but ranged from 20-150. The number of cells/divot can be manipulated based on the density of cells in the media that is loaded into the mold providing advantages to the user for controlling the ultimate size of the target 3D cellular structure.

The micro-molds were gently shaken then allowed to sit for 15 minutes so that the cells settled into individual divots. The islets were maintained at 37° C. with 5% $CO_2$ for up to 9 days with media changes daily. Changing media in the micro-molds, with 60 μm deep divots was accomplished easily be gently removing (with suction) the old media from near the divot sidewall, and gently pipetting in to the mold the fresh media.

Reaggregation of Cell Clusters within Micro-Molds.

Figure 14:
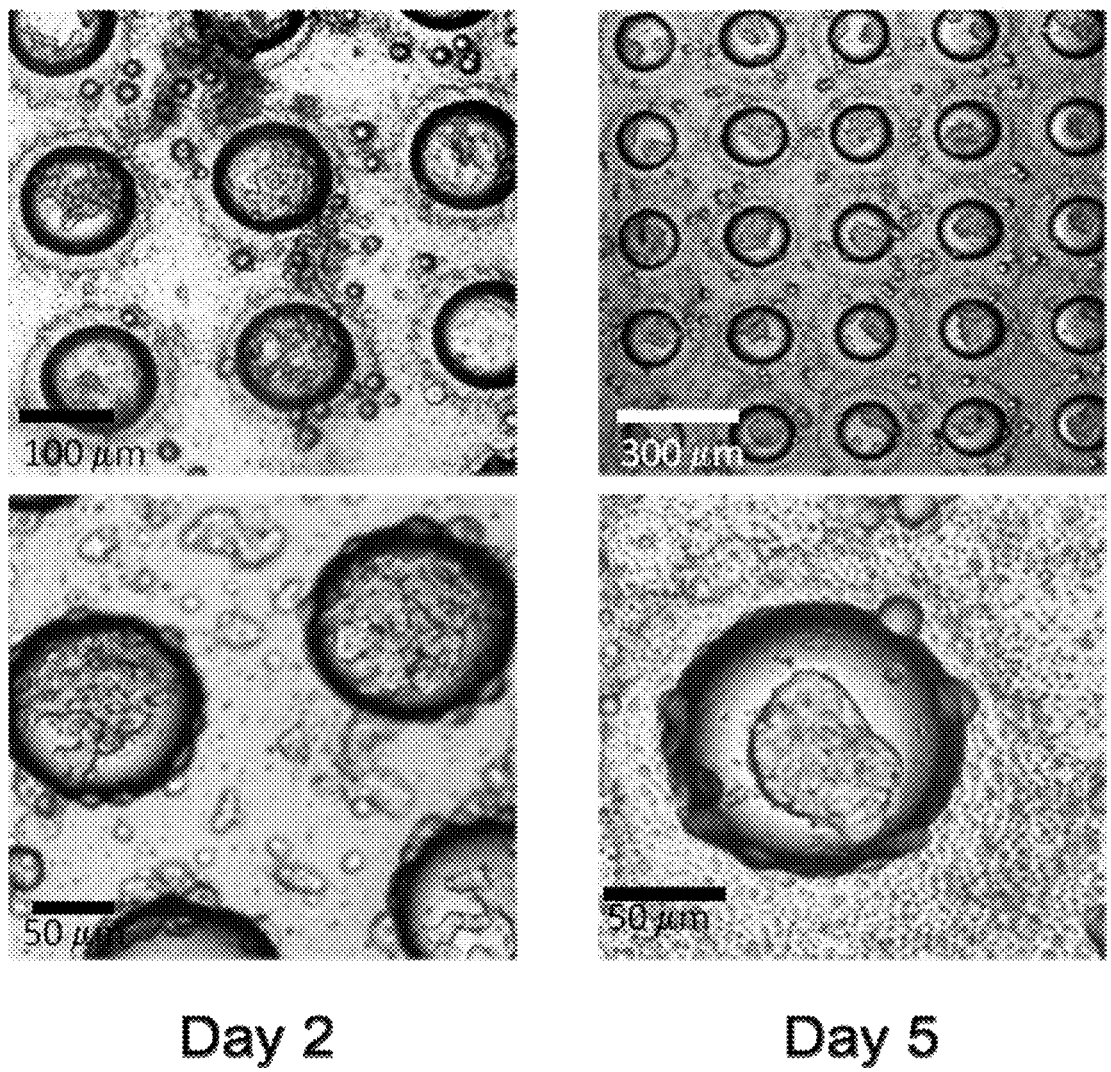
FIG. 14 is a micrograph showing islet cell reaggregation within the divots of a micro-mold on days 2 and 5.

Initially the cells fell randomly into each well. The number of cells that settle into each divot is set by the density of cells in suspension. In order to determine cell density prior to loading the micro-mold, an aliquot of the islet cell suspension is removed and the cells/volume are counted under a microscope using a hemocytometer. Knowing the number of divots in the mold, and the target size of each reaggregated islet, the number of cells in the suspension can be concentrated or dilute depending on the starting cell density. If a mold contains 10,000 divots and the desired outcome is 100 cells/divot, then there must be 1,000,000 cells in the media loaded into the micro-mold. FIG. 14 shows cells developing in a micro-mold starting on day 2 and advancing to day 5. Between days 3 and 4, the cells began to take on the 3D shape of a native islet. Islets that developed within divots were all limited to less than 90 μm in diameter (mean diameter less than 50 μm). This dimension is important as we have published data showing that 50 μm is a critical size for ensuring nourishment to the core cells of the islet (Williams et al., 2010). Islets greater than 50 μm demonstrated core cell death, while those less than 50 μm rarely demonstrated core cell death in culture. The curved bottom of each divot helped to draw the cells towards one another for optimal formation of the spherical reaggregated islets. FIG. 14 shows the measurements taken of a single divot depth using a profilometer. The depth of this single divot is slightly greater than 60 μm and the bottom is curved, which pushes the cells towards the center of the divot for aggregation.

Figure 15:
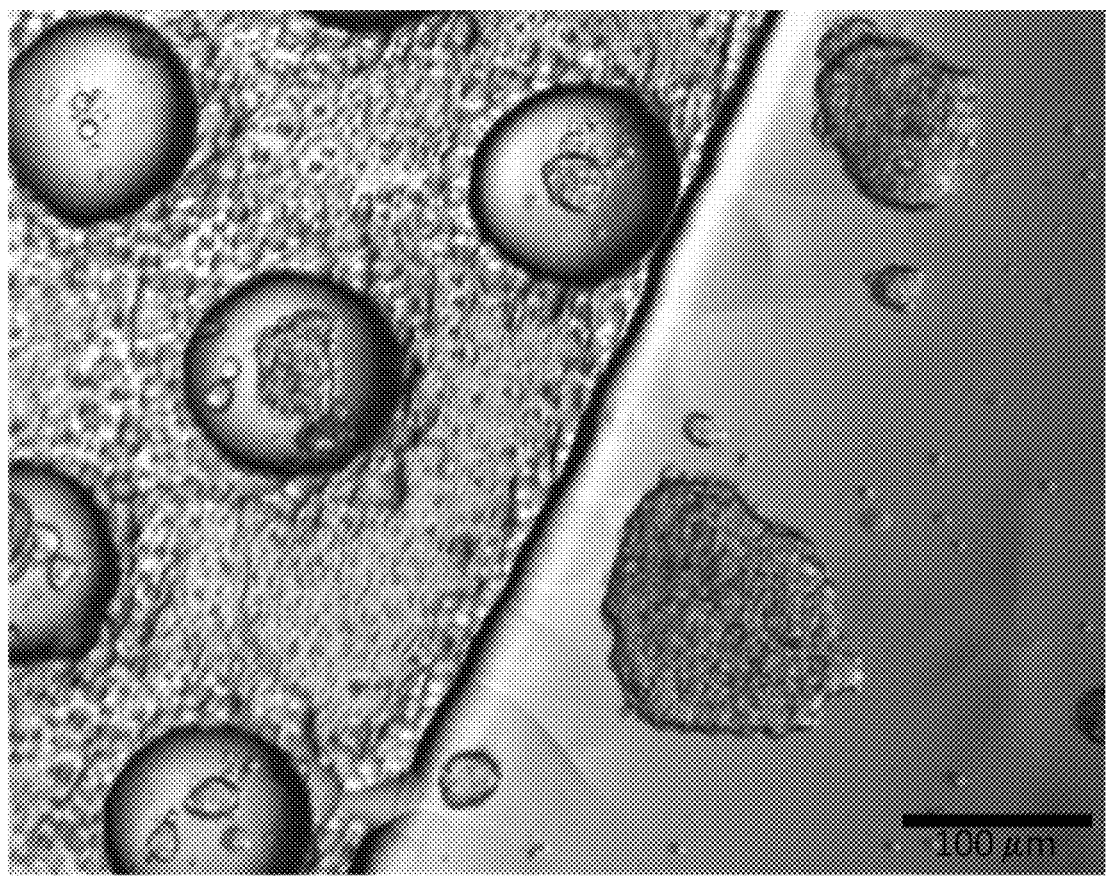
FIG. 15 is a micrograph showing the undivoted edge of the divoted substrate adjacent to the field of divots; divots contain small reaggregating islet cells, but those cells that fell onto the undivoted surface have reaggregated into large mega-islets.

Success in generating reaggregated islets of optimal size and shape is exemplified by results obtained from an early prototype. This early prototype comprised undivoted substrate surface area surrounding the field of divots (FIG. 15). When seeded, some cells fell onto the undivoted surface of the prototype micro-mold. While some of the cells that fell onto undivoted surfaces stayed in the form of single cells or grew into small cell clusters, others formed mega-islets; huge complexes that were not limited by the divot specifications (FIG. 15). Within this early prototype mold, cells isolated from the same animal, that were cultured in the same media, and reaggregated on the same substrate material produced two different cell reaggregates: i) those formed within divots formed small well-shaped islets, and ii) those formed on the flat surface unrestricted to the physical constraints of a divot formed large conglomerations of cells that are subject to poor diffusion properties. Some of the unrestricted islets grew to a size of 400 μm in diameter. These results provide excellent proof-of-concept that physically restricting the reaggregation of cells results in optimally-sized islets.

Figure 26:
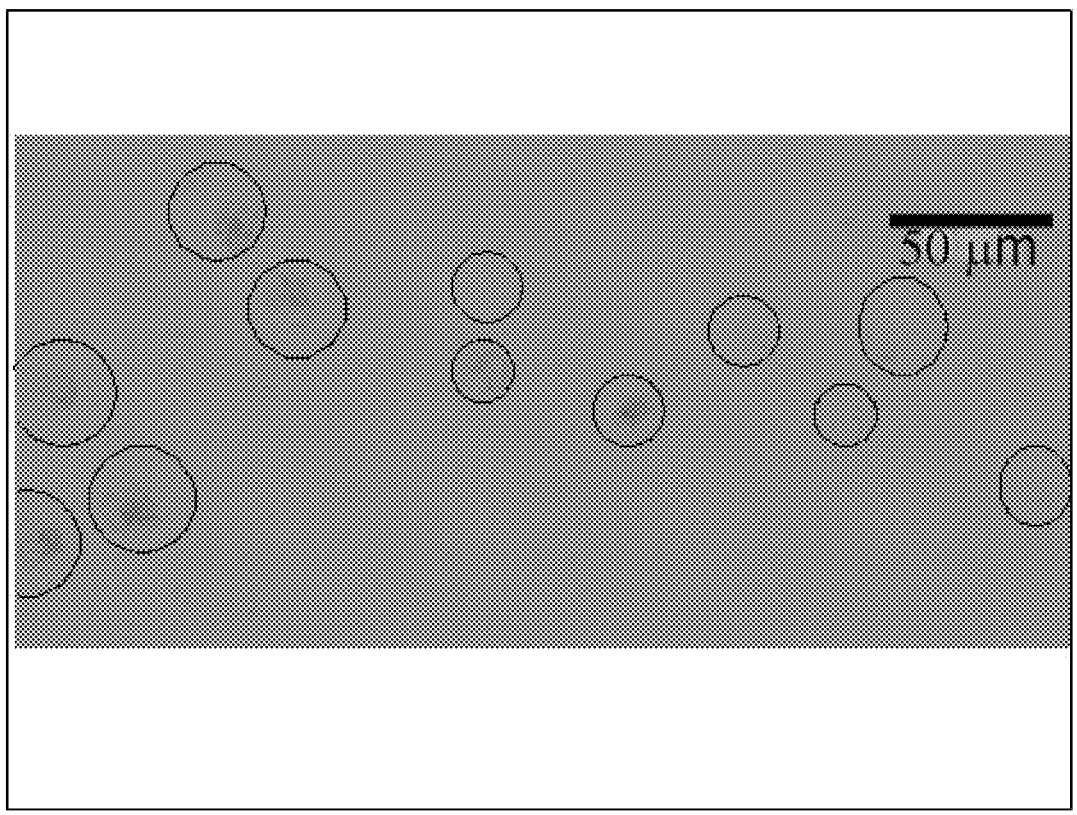
FIG. 26 shows reaggregated islets in media containing 2-[N-(7-nitrobenz-2-oxa-1,3-diazol-4-yl)amino]-2-deoxy-D glucose (2-NBDG; 20 mM). Circles indicate location of islets. 2-NBDG, a fluorescent glucose analogue, is fully integrated into each reaggregated islet.

Experimental data suggest that islets reaggregated in micro-molds demonstrate diffusion properties similar to those exhibited by native small islets. To determine the diffusion properties of islets reaggregated in micro-molds, reaggregated islets were exposed to media containing a fluorescent analogue of glucose, 2-NBDG (available from Cayman Chemical, Ann Arbor, Mich.), for 10 minutes. The fluorescent glucose analogue completely infiltrated to the core of the reaggregated islets indicating that the barrier to diffusion of glucose is relatively low (FIG. 26). In contrast, previous work showed that native large islets have significant barriers to diffusion that inhibit the infiltration and cellular uptake of glucose into the core of the islet, even after hours of exposure to 2-NBDG (Williams et al., 2010). Collectively, these data indicate that islets reaggregated in micro-molds have low diffusion barriers relative to native large islets.

Comparison of cells formed in micro-molds to those formed in commercially available multi-well plates.

Figure 16:
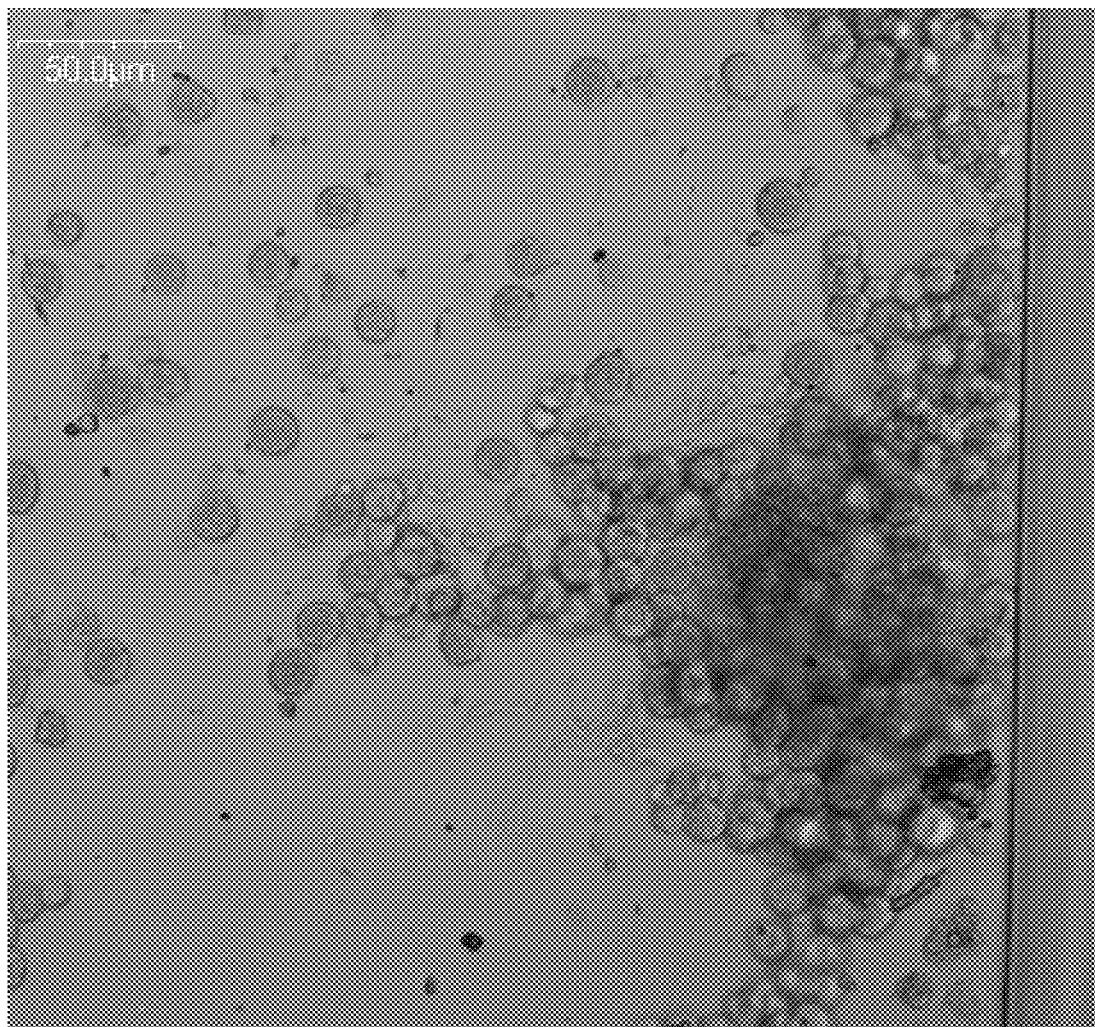
FIG. 16 is a micrograph showing live islet cells congregated at the edge of a well in a commercially available plate; reaggregation of islet cells is not spherical as in the micro-mold, and the reaggregated group of islet cells is much larger than the 90 µm islets formed in micro-molds.

The results of reaggregating islets in the micro-molds were compared to reaggregating islets in commercially available micro plates. The commercial plates contained square-shaped wells that measured 1700 μm in diameter. Dispersed islet cells were cultured in the commercial plates and islet-like clusters formed, as predicted. Several observations were made. First, the islet cells formed in commercial plates congregated and bound to each other in the corners of the wells where they could contact the walls. FIG. 16 shows a typical example of the cells forming a reaggregated islet touching the side of the commercial well. These cells use contact guidance to reform.

Second, without limitations to the size, more and more cells bound together creating giant islets (some over 400 μm in diameter) with poor viability. Without the small micro-molds to limit the number of cells within each well and the physical dimensions designed to optimally guide the shape of reaggregated islets, the resulting islets were very large and contained a high percentage of dead cells. In viability assays from islets reaggregated in the commercially-available plates, over 50% cell death was noted with 6 days of culture. In these large openings, cells often remained as singlets, showing poor cell viability. Those cells that were able to cluster along the wall or corner of the well never formed the spherical shapes indicative of native islets, and had poor viability.

Third, the clusters of cells that formed in commercial molds did not reaggregate into the spherical islet-like tissue that we were able to obtain using the micro-mold. The sphere-forming ability of the reaggregated islets is likely an important feature predictive of successful in vitro function. Most multi-well plates are manufactured with flat bottom wells and square sides as shown in FIG. 16. Cells reaggregated in commercial plates such as these do not attach to one another in a native-reminiscent sphere, and therefore are less likely to function as efficiently as a native islet. These results support the notion that current commercially available molds are inappropriate substrates for optimal islet formation.

Removal of Reaggregated Cell Clusters from Molds.

In some instances it is desirable to remove the reaggregated islet cells from the micro-mold in a manner that does not compromise the integrity or viability of the cells. This can be easily accomplished by gently placing a large pipette directly over the divots and applying suction. The reaggregated islets are removed from the divots with the media. Subsequent washing of the micro-mold with fresh media and pipetting directly over the divots will remove almost all reaggregated islets in the mold.

Characterization of Cell Reaggregates Formed in Micro-Molds.

Figure 17:
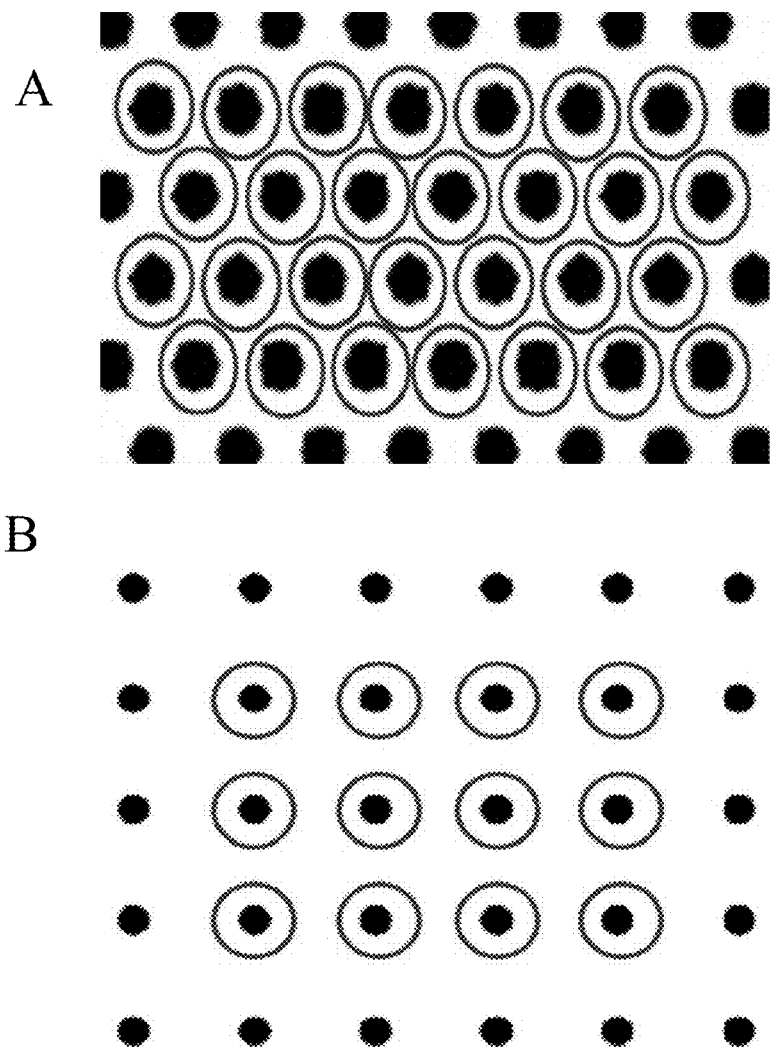
FIGS. 17 A and B is a set of schematics showing two possible divot patterns for the micro-mold.
Figure 18:
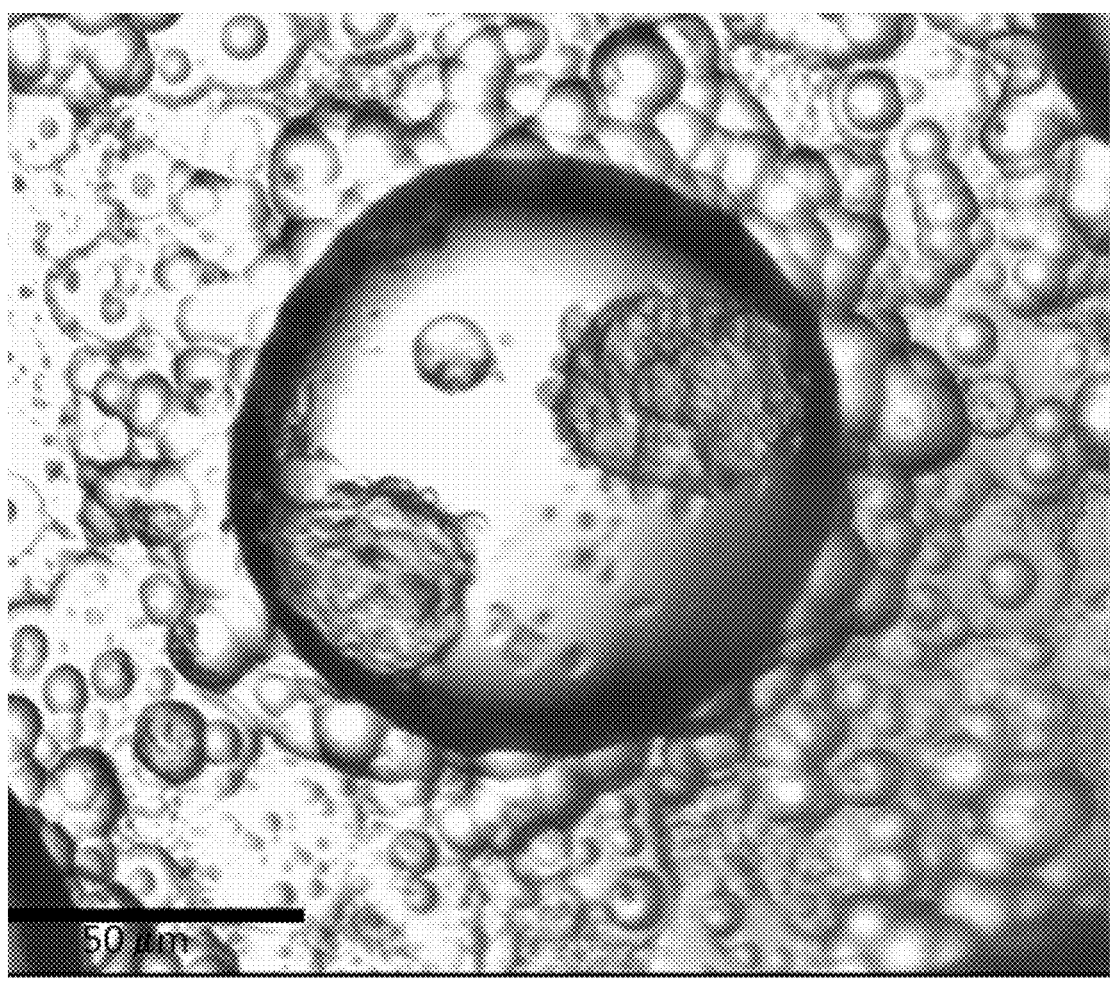
FIG. 18 is a micrograph showing two reaggregated islets contained within a single divot.

Islets removed from the microplates were measured for size and viability. Native rat islets range from 20-350 μm in diameter. When reaggregated within divots of the micro-mold (100 μm diameter, 60 μm deep), 100% of islets had diameter less than 90 μm; the mean diameter per reaggregated islet was 36.6±1.2 μm (confocal microscopy measurements of over 500 individual reaggregated islets). Originally, we found a few larger structures that we believed represented islets that were never fully digested to single cells and therefore never fell into the divots. Since then, greater care during the dispersion procedure has led to islet suspensions with 90% of the cells in singlets and the remaining cells predominantly in doublets or triplets. We estimate, using micro-mold patterns A and B (FIG. 17), that 85-90% of all aggregates obtained are below 90 μm in diameter. For reasons not yet understood, some of the cells in the divots divided into multiple islets rather than forming one reaggregated islet per divot. FIG. 18 shows an example of two reaggregated islets within one divot.

Figure 29:
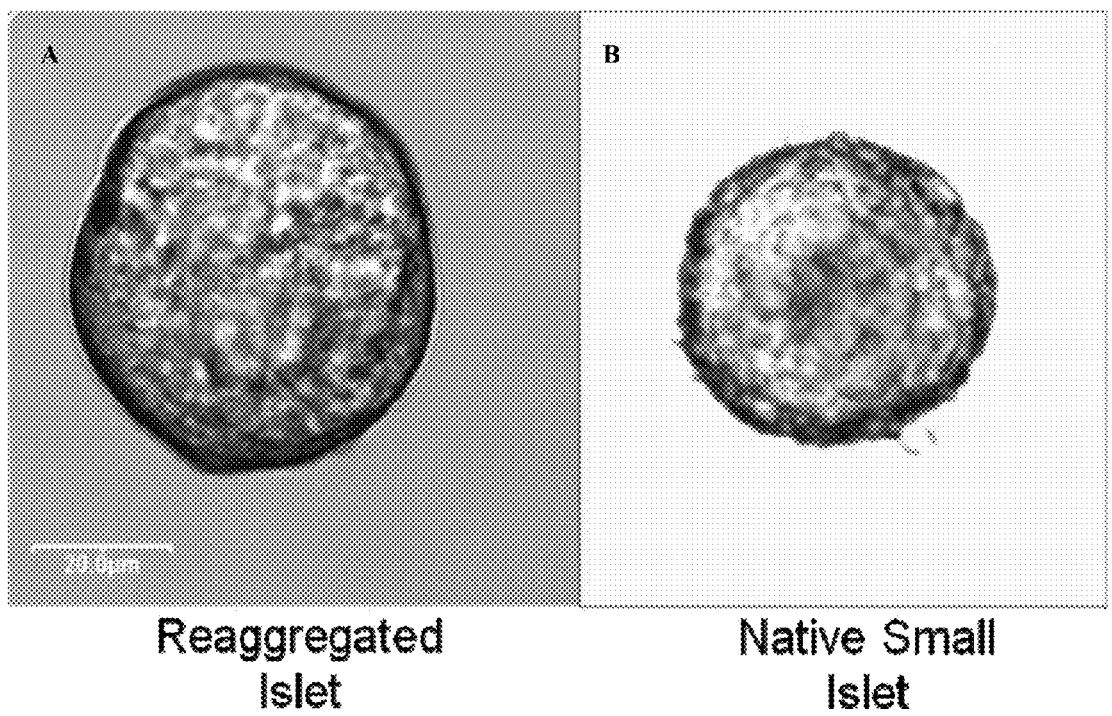
FIGS. 29 A and B compares two islets of approximately the same size.

Morphologically, the reaggregated islets look identical to native islets of the same size. They are spherical in shape with a capsule-like external surface surrounding the islet, as can be seen in the FIG. 29. In contrast, FIG. 15 shows that cells aggregating without the micro-mold do not form spheres or an apparent capsule.

Viability experiments were completed on the reaggregated islets using apoptosis/necrosis cellular stains (Invitrogen, Vybrant Apoptosis Assay containing Yo-Pro-1 and propidium iodide). This double-labeling assay measures both membrane integrity and fragmentation of DNA. Reaggregated islets were incubated in the two labels for 1 hr using known methods (MacGregor et al., 2006; Williams et al., 2010). Subsequently, islets were rinsed with PBS and placed in the Attofluor Chamber on the Fluoview 300 confocal microscope. Reaggregated islets were optically sectioned and images from the center of the islet were stored for later analysis. The area within the islet containing stain was calculated as a percentage of the total islet area to determine viability. Viability measurements of 5 day old reaggregated islets demonstrated extremely high viability within the cells and revealed very few dead cells/islet. The overall viability of the reaggregated islets was 99.76%. This value is higher than previously reported in the literature for native large and small islets, and for single islet cell dispersions (Williams et al., 2010; Song et al., 2009).

Figure 19:
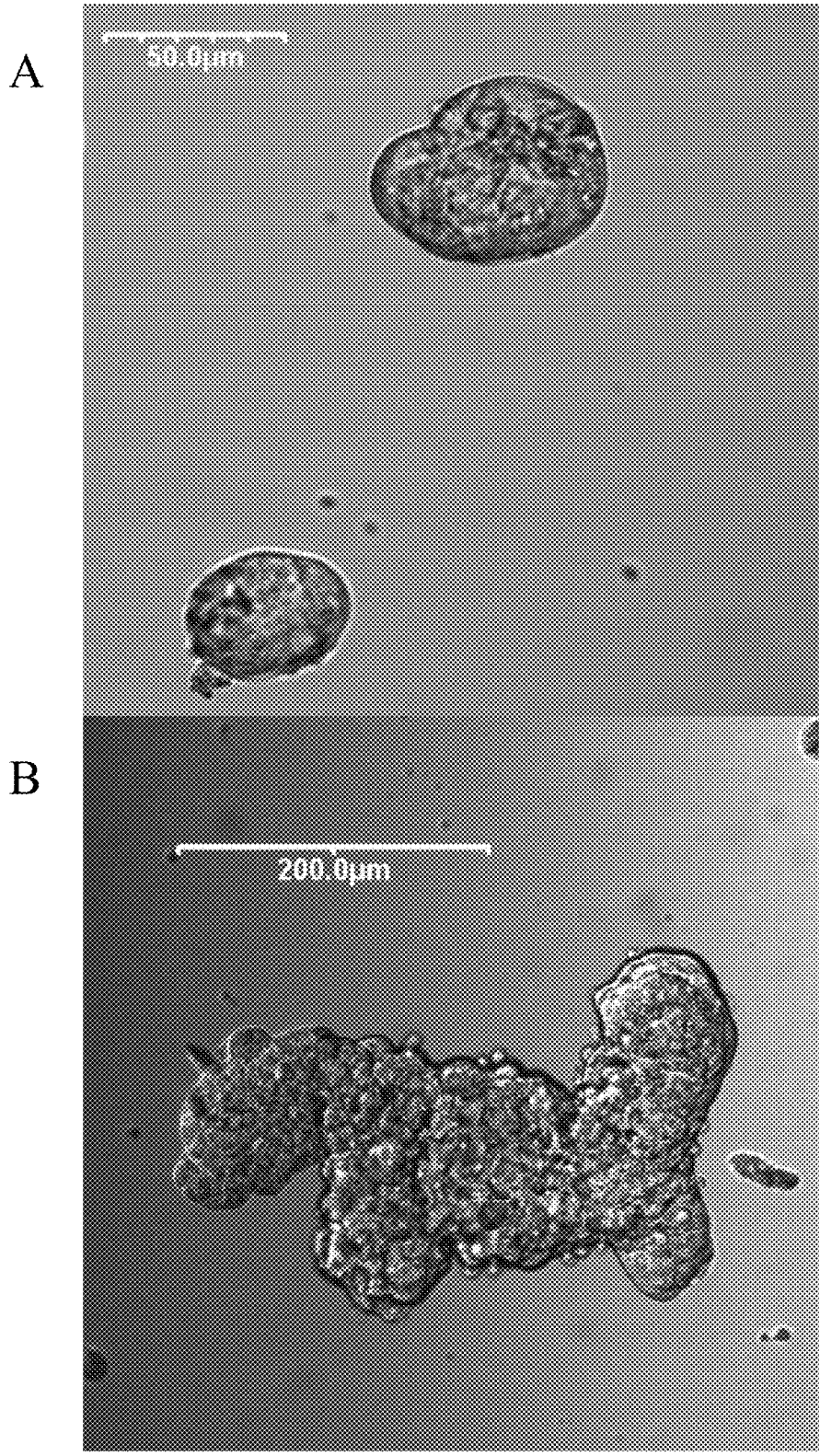
FIGS. 19 A and B is a set of micrographs showing viability staining in reaggregated islets; red indicates dead cells.

FIG. 19 shows examples of typical islets stained for viability. In these tests, red staining indicates cell death from necrosis and green cell staining indicates cell death from apoptosis. FIG. 19A shows one of only a very few dead cells that were identified in the islets reaggregated in the micro-molds. The cell stained red is undergoing cell death due to necrosis. In isolated tissue, cell necrosis often occurs first. Only two apoptotic (green) cells were noted in 500 islets tested. In contrast, when cells from the same animal formed large mega-islets on the surface of the micro-mold, there were significant numbers of dead cells present throughout the mass. FIG. 19B captures one plane of view with 23 dead cells. Adjustment of the focal plane of the microscope showed that more dead cells were present within all planes of the mass. Thus, cells reaggregated in the divots to islets of the correct proportions had very high viability, while cells allowed to reaggregate into large masses outside of the divots showed significant cell death. These results demonstrate the success of the micro-mold, because the cells that landed on areas of the mold without divots had much poorer viability than those formed in divots.

Figure 20:
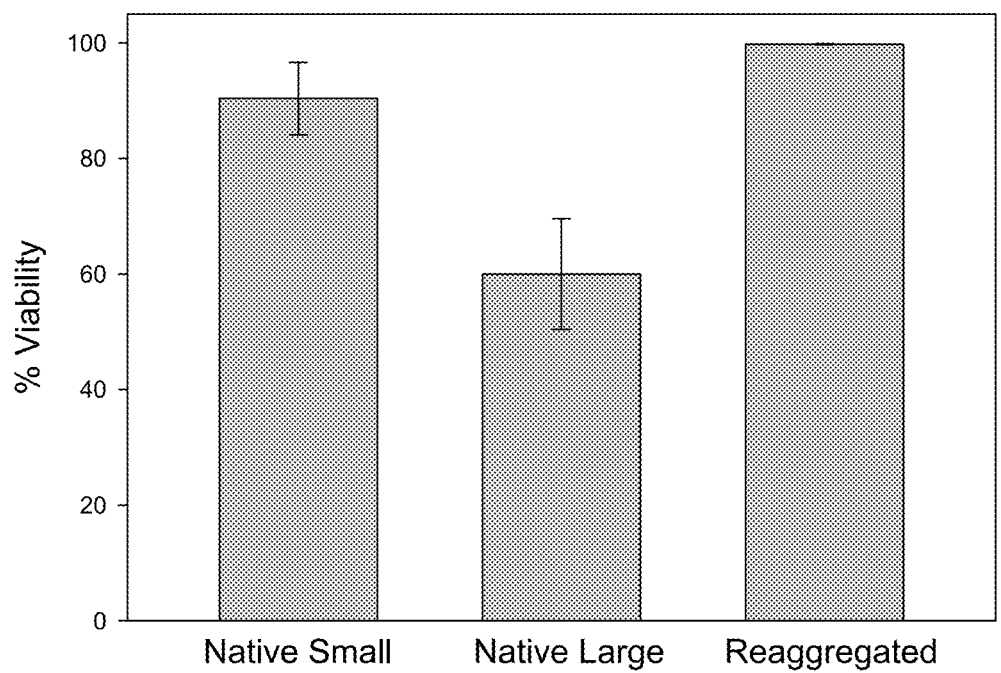
FIG. 20 is a graph comparing the viability of native small and native large islets with reaggregated islet. All islets were removed from the same rats and a portion of the isolated islets were dispersed into islet cells for reaggregation. On day five, the reaggregated islets were removed from the micro-mold and all islets were exposed to live/dead viability stains. The percentage of live cells in the reaggregated islets was higher than that for native large or small islets.

The viability of all cells formed in micro-molds exceeded that of native large and small islets from the same animals (FIG. 20). Viability was compared between rat large, small and reaggregated islets using the Vybrant Apoptosis Assay (Invitrogen), as described previously. Six days after isolation, there was some variability in the percentage of live cells in the two groups of native islets, however there were few dead cells in the reaggregated islets, leading to error bars that were too small to be visually represented. Islets reaggregated in micro-molds exhibited approximately 10% higher viability than native small islets and approximately 40% higher viability than native large islets (FIG. 20).

Cell Populations Generated from Micro-Molds.

Figure 21:
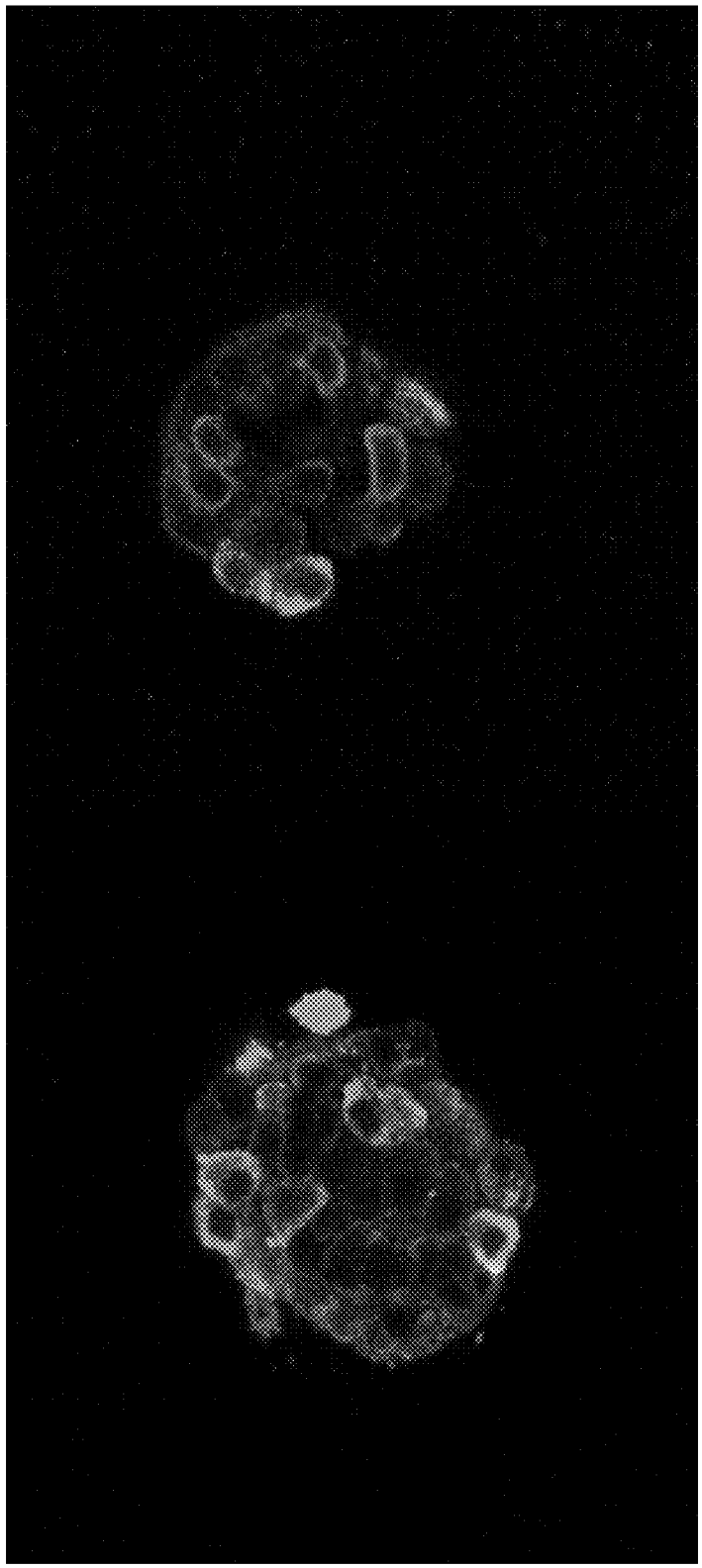
FIG. 21 shows two representative islets 6 days after reaggregation in micro-mold divots that have been triple-stained to identify beta cells (green), alpha cells (red), and delta cells (blue). The upper islet measures 43×55 µm in diameter (measured in X and Y directions), and the bottom islet measures 48×65 µm in diameter.

There are three major types of cells present in native islets (both large and small) that comprise about 90% of the total cells in the islets. Alpha cells that secrete glucagon make up about 20% of all of the cells in the islet. Beta cells that produce insulin make up 60-65% of the total cell numbers, and delta cells that somatostatin comprise 5-10% of the islet cell composition. Islets engineered in the present micro-molds have been shown to contain alpha, beta and delta cells. For example, FIG. 21 depicts two representative islets formed in the present micro-molds 6 days after reaggregation; beta cells are stained green, alpha cells are stained red, and delta cells are stained blue. These engineered islets appear to have a lower percentage of beta cells than the average native islet. However, when compared to native small islets, the cellular relative composition of alpha:beta:delta cells and their organization may resemble native small islets. Native rat large and small islets are organized with glucagon-positive and somatostatin-positive cells located on the outer layers of the islet. The insulin-positive cells are found in the center. As such, the percentage of insulin-positive cells (the beta cells) is less in the small islet, but each islet contains high quantities of insulin. Although we have not calculated the percentage of beta/alpha/and delta cells (insulin/glucagon/somatostatin-positive cells) in enough reaggregated islets to conclude definitively, it is likely that the percentage of beta cells compared to all other cells will resemble the native small islet. One important difference is that in the reaggregated islets, the alpha, beta and delta cells are organized in a random pattern with the cells dispersed throughout the reaggregated islet. This is the same organization noted in human islets (Hahn van Dorshe et al., 1988; Bosco et al., 2010. Thus, the reaggregated islets demonstrate a more random pattern of cell organization, reminiscent of native human islets.)

Insulin Production.

Figure 22:
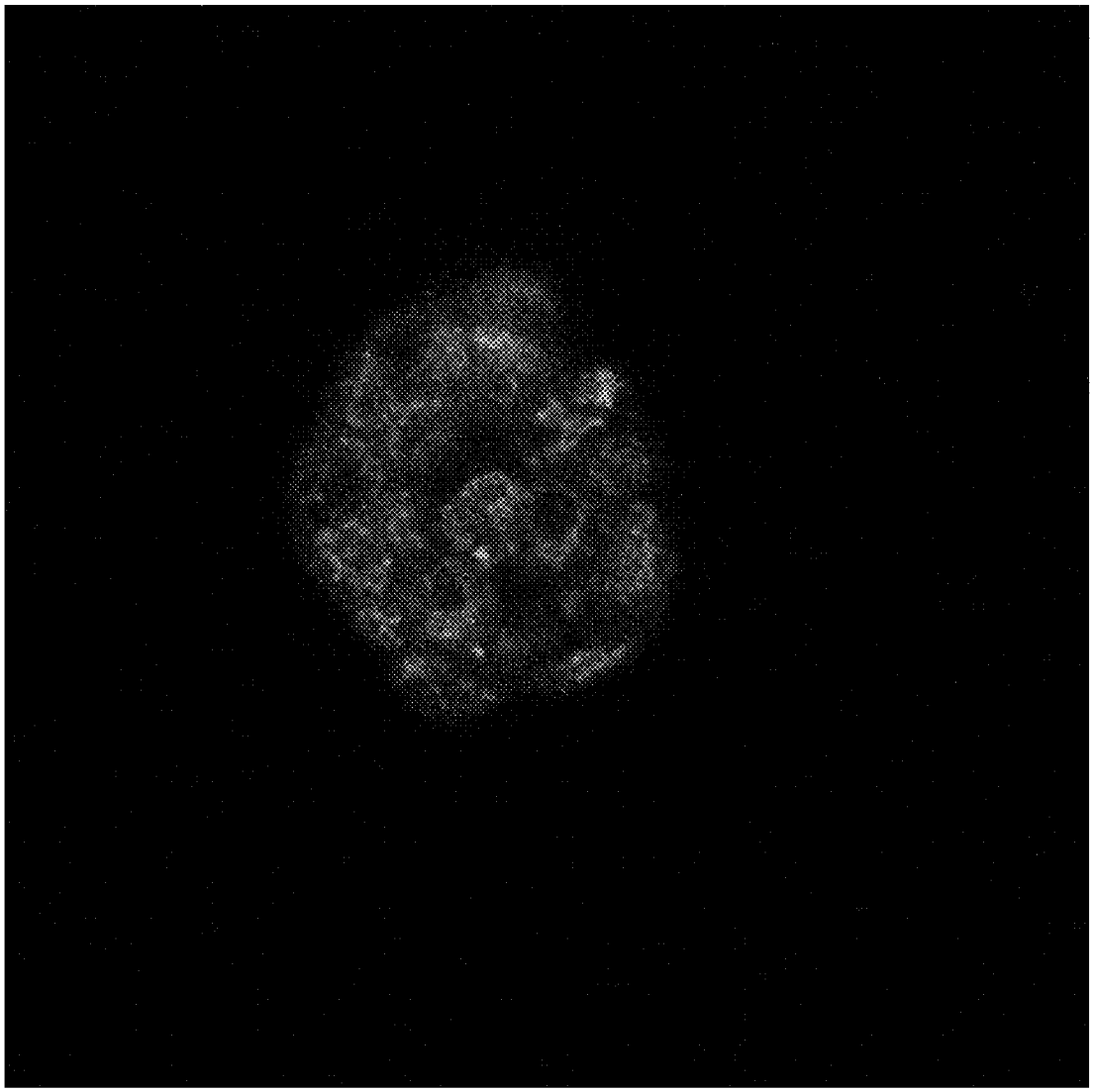
FIG. 22 shows a 6-day reaggregated islet formed in a micro-mold divot that has been stained for insulin (green) and proinsulin (red). This islet is 45×54 µm in diameter (measured in X and Y directions).

It was important to verify that islets engineered in micro-molds were able to produce new insulin molecules. Insulin is first synthesized as a precursor molecule, called proinsulin. Six day old reaggregated islets were stained for proinsulin levels to determine whether they were making new insulin. FIG. 22 shows an example of a reaggregated islet stained for mature insulin (green) and proinsulin molecules (red). As expected, the beta cells are double-labeled. The image shows that new insulin is being synthesized in the reaggregated islets, even six days in culture.

Figure 23:
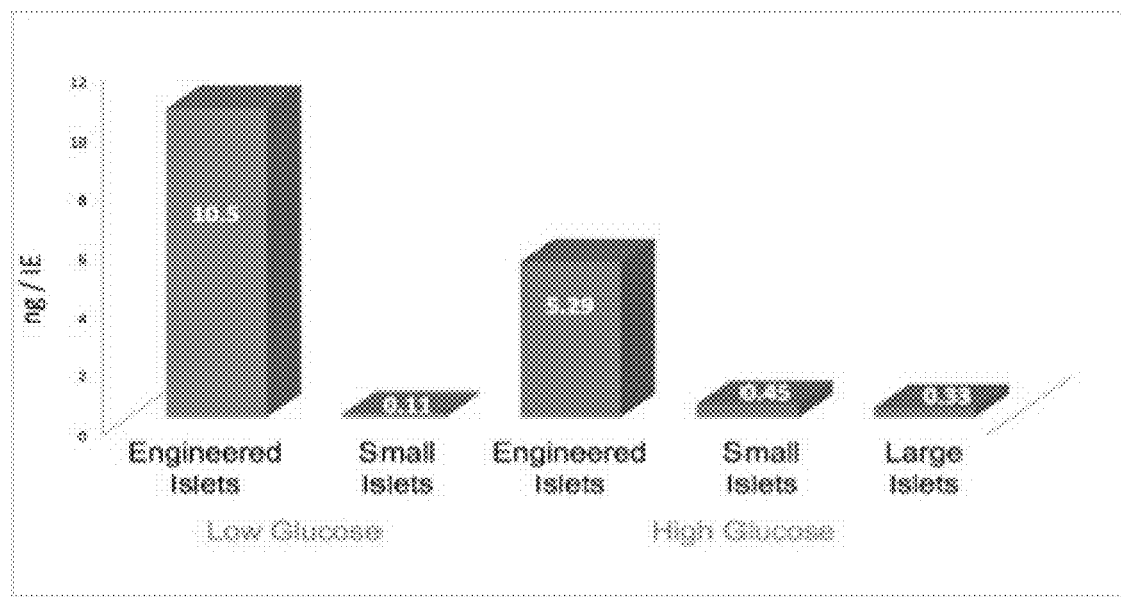
FIG. 23 is a graph depicting insulin secretion in three islet types exposed to different glucose conditions. Native small islets and islets reaggregated in micro-mold divots were exposed to low glucose conditions (3 mM); insulin secreted into the media was collected and quantified as indicated by the Y axis. Native small islets, native large islets and islets reaggregated in micro-mold divots were exposed to high glucose conditions (20 mM); insulin secreted into the media was collected and quantified as indicated by the Y axis.

Islets are responsible for releasing insulin into the blood in response to high glucose exposure after eating a meal. The lack of insulin secretion is the cause for the inability of people with type 1 diabetes to maintain normal blood glucose levels. To determine cell response to glucose, islets reaggregated in the present micro-mold and native small islets were exposed to low glucose conditions (3 mM). Insulin secreted into the media by both islet types was collected and quantified (FIG. 23). In low glucose conditions (30 minutes), reaggregated islets released 100 times more insulin than the native small islet (native small islets produce more insulin than native large islets). When exposed to high glucose (20 mM), the reaggregated islets continued to secrete significantly more insulin than the native large or small islets. To confirm that the reaggregated islets were secreting insulin rather than leaking insulin we completed additional experiments using a small membrane impermeant dextran (10 kDa). A molecule this size is small enough to pass through the nuclear pore complex on the nuclear envelope within the cell. However, the plasma membrane does not contain protein complexes able to pass molecules of this size. The dextran (20 mM) was added to media containing reaggregated islets and confocal images captured the inability of the dextran to enter the cells even after 4 hours of exposure, suggesting that the cells were not leaky or membrane-damaged. Additionally, if cells were in fact leaking insulin rather than secreting it, we should have observed higher levels of red or green staining during necrosis/apoptosis assays in the reaggregated islets shown in FIG. 22. Collectively, these data suggest that islets reaggregated in micro-molds do indeed produce higher quantities of insulin than their native small or large islet counterparts.

To our knowledge, insulin secretion at these levels from native or altered islet cells has not been reported, making our results unique. The Weir group reported encapsulating small reaggregated islets into an alginate with high guluronic acid content (O'Sullivan et al, 2010). Weir created these islet aggregates by simply dispersing islets to single cells and then allowing them to reshape without restrictions. Weir's work showed that in normal oxygen levels their small islets released as much insulin as native islets, but in low oxygen the Weir islets released more insulin than native islets. However, Weir's best performing islets secreted 20 times less insulin than our islets reaggregated in micro-molds. The reason for the relative decline in insulin secretion by our reaggregated islets in high glucose is unknown at this time, and something that must be determined before the engineered islets can be transplanted into diabetic animals. In spite of the relative decline, the dramatic increase in insulin secretion in both low and high glucose conditions, compared to the native islets, is an important and unique attribute of the micro-mold reaggregation method.

Additives to Islets.

Alternative methods and materials that could be utilized with the process of reaggregating islets in micro-molds are nearly limitless. First, there are many molecules that could be incorporated into the engineered islets at the time of reaggregation. These include but are not limited to growth factors, immunomodulators, immunosuppressants, cytokines, chemokines, DMARDs (disease-modifying antirheumatic drugs), anti-inflammatories, and antibiotics. Molecules or miniature devices to increase oxygen tension at the transplant site could be incorporated into the reaggregated islets, especially if an implantable micro-mold substrate were used. Other non-limiting classes of molecules that could be added at the time of reaggregation includes drugs to induce insulin release, small molecules, peptides, proteins, antibodies (e.g. against CD11a, CD11b, CD11c, CD18), and nucleic acids (e.g. DNA or RNA).

Discussion.

Our divoted micro-mold is unlike other scaffolds used in the art to reaggregate cells. Previously, others have attempted to use the hanging drop method to form islets (e.g., Lehmann et al., 2007). In the hanging drop method, cells are placed in solution, into a drop on a Petri dish lid, which is then turned upside down so that the cells fall to the bottom of the hanging drop of solution, where they might form an islet. However, the hanging-drop method is time-consuming and prone to contamination because the media in the "drop" cannot be changed.

Utility of Micro-Molds In Vitro.

The present micro-mold can be designed to form cell aggregates in vitro for subsequent transplantation or for drug or device testing among other applications.

Generating cells for transplant. (Prophetic Example) A preferable micro-mold designed to generate cells for transplantation is a single device that is sterilizable, re-usable, and does not leak media or cells when filled (FIG. 24). First, islets need to be isolated from the pancreas. The small healthy islets would be separated from the large islets. Large islets would be dispersed into single cells or doublets, which are loaded into the micro-mold. After 3-6 days in culture, the cells would be removed, mixed with the native small islets, and transplanted into the diabetic recipient.

Micro-mold A (FIG. 17A) is designed for islet reaggregation with divots that are 100 µm in diameter with a 60 µm depth. We have found that 60 µm depth is optimal, as it allows for easy removal of the reaggregated islets from the divots. The divots are arranged in an alternating pattern so that there is minimal space between divots (FIG. 17A). The average distance between divots is less than 30 µm.

The undivoted surface seen in FIG. 15 would be entirely covered in divots in the envisioned micro-mold for generating cells for transplant. This arrangement allows for maximal space on the micro-mold to be used for divots—resulting in maximum numbers of reaggregates made per mold, and maximum efficiency such that any cell floating to the surface of the mold will likely fall into a divot, thus limiting the loss of viable cells for reaggregation.

The number of divots that can be obtained on one mold will vary with the size of the mold. A mold of approximately 1.5 inches in diameter, using the micro-mold A design (FIG. 17A), contains between 10,000-12,000 divots per mold. The spacing of the divots is also dependent on the needs of the mold. For reaggregation of tissue for transplantation, efficiency of the original tissue to the number of reaggregated islets is important. The greater the percentage of cells that falls into the divots, the better the efficiency in making the new islets. So our molds designed for islet transplantation have a divot spacing of 20-30 µm.

Drug screening. (Prophetic Example Using the Micro-Mold) Drug screening using the micro-mold is based on the concept that cells arranged in a 3D structure, like a mini-tumor or small islet, will respond to their environment differently than cells grown or reaggregated flat in a dish. For example, mini-tumors or islets could be formed in the divots of the micro-molds, and then potential therapeutics, such as anti-cancer drugs, could be applied either individually to each divot, or added to the entire plate. One would then examine the formation of the 3D structures and note changes, such as decreased cell viability or cluster size, that would indicate an undesirable effect of the test chemical. In the first example, many different drugs could be tested on one piece of glass that is approximately 35 mm in length. With the second approach a single drug would be tested, but in one mold there would be many individual responses that could be quantified.

One possible quantification for cancer drug testing would be viability (live/dead stains), which could be done for each tumor. While testing potential cancer drugs using the micro-mold design is appealing, the mold would be useful for all drug testing that is best done on cells in a 3D arrangement.

Micro-mold B (FIG. 17B) is designed for delivery of individual interventions to each well. Thus, it would be applicable for drug testing. For this design the divots were approximately 180 µm in diameter with 120 µm of space between each divot. The spacing can be increased or decreased as needed. FIG. 11 shows an image of the floor of micro-mold B with individual empty divots. Micro-mold B contains 2,700-3,000 divots per mold, many fewer than in design A. The spacing between the divots in design B is greater to ensure accurate drug delivery to only one divot. Specification of the divot pattern and spacing is set by the user and will depend on the drug delivery system used. Using the molds to test thousands of compounds on cells in each divot would allow the user to complete drug screening on 2000-3000 different drugs in a mold that is less than 2 inches in diameter (FIG. 24). High throughput drug screening utilizing each mold for a separate drug, would allow thousands of individual cell clusters to respond and be measured as individual responses rather than an average response. High throughput drug screening partnered with nano-delivery systems could be utilized such that each divot could contain a different drug for testing. Alternatively, one could collect data points from thousands of samples exposed to the same treatment and culture conditions (FIG. 24).

Generation of non-islet cells. (Prophetic Example) Molds can be designed for a variety of cell aggregation shapes including but not limited to, long neuronal pathways, glomerular-like filters, vessels, replacement alveoli, etc. Aggregation of stem cells or reprogrammed cells in a small, well-defined shape such as the micro-mold would also be an appropriate use of this invention.

One typical application would be the expansion and aggregation of cultured cell lines into the molds. In this case, cells in suspension would be loaded into the molds at an extremely low density ranging from 1-50 cells/divot (depending on the needs of the user). Cultured cell lines contain dividing cells, which would be allowed to grow in the divots for a length of time depending on the needs of the user. Other cells sources would include freshly dispersed cells from animals or humans. The process to load freshly-dispersed cells is similar to the general methods described for islets. The tissue of choice, for example a vessel, would be exposed to digestive enzymes until single cells or doublets were in suspension. The cells would be loaded into the mold at the density and in the media of choice by the user. Finally, stem cells could be programmed to produce various adult cell types. These cells could also be loaded into the micro-molds to enhance 3D structure formation.

Utility of micro-molds in vivo. (Prophetic Example Using the Micro-Mold) The micro-molds described here are useful for in vitro applications.

Reaggregate islets in molds for transplantation. (Prophetic Example) Micro-molds constructed from biopolymers can be used to generate an implantable product (FIG. 23). In such case, the micro-environment of the mold would be altered so that reaggregated islets would attach to the biopolymer, and the entire "patch" would be transplanted into the recipient. The biopolymers described supra would be appropriate for generating such an implantable micro-mold. The divots in the mold could be used to create wells that would allow the cells to first settle into the divots where their reaggregation would be guided by the dimensions of the divot, and second to adhere to the biopolymer divot.

In order to create divots in the biopolymer, wax negatives would be designed using protocols known in the art (e.g., Dean et al., 2007). For molds that are implantable, the islets would be left in the mold and surgically placed into the recipient. Implantable molds would have a mold design with openings between the divots that would allow the infiltration of nerves and blood vessels to the islets. Furthermore, implantable materials could be impregnated with, for example, neuronal and vascular growth factors and the molds could also contain immunosuppressants to protect the islets from immune rejection.

Implantation of the mold with islets could be done using several published methods. The micro-molds could be placed into the peritoneal cavity as published by Qi et al., 2010. The abdominal cavity is opened under anesthesia, and the mold would be gently placed into the subfascial space. Alternative sites for implantation of the micro-mold include subcutaneous insertion, especially following preconditioning to increase the vascular supply to the region as described by Veriter et al., 2010. In human transplantation, the islets are placed into the liver via the portal vein (Koh et al., 2010). With micro-molds, infusion through the portal vein would not be possible, but the molds could be placed in the liver or under the kidney capsule with more invasive surgery (MacGregor et al., 2006).

Example 6

Method and Device for Screening a Compound for Biological Activity

In this Example, development, design and methods for using wall-modified micro-molds are described. The wall-modified micro-molds described in this Example are particularly well suited for high throughput screening of drugs and toxicology testing. As discussed below, islet cells reaggregated and screened in a "walled-micro-mold" are optimally sized, viable, characterized by high percentage viability and high levels of insulin secretion, and suitable for high throughput drug testing and long-term maintenance. Further, the walled-micro-mold is compatible with equipment and computer systems known to be useful for high throughput screening, including drug and toxicology testing.

Development of Walled-Micro-Mold.

Figure 34:
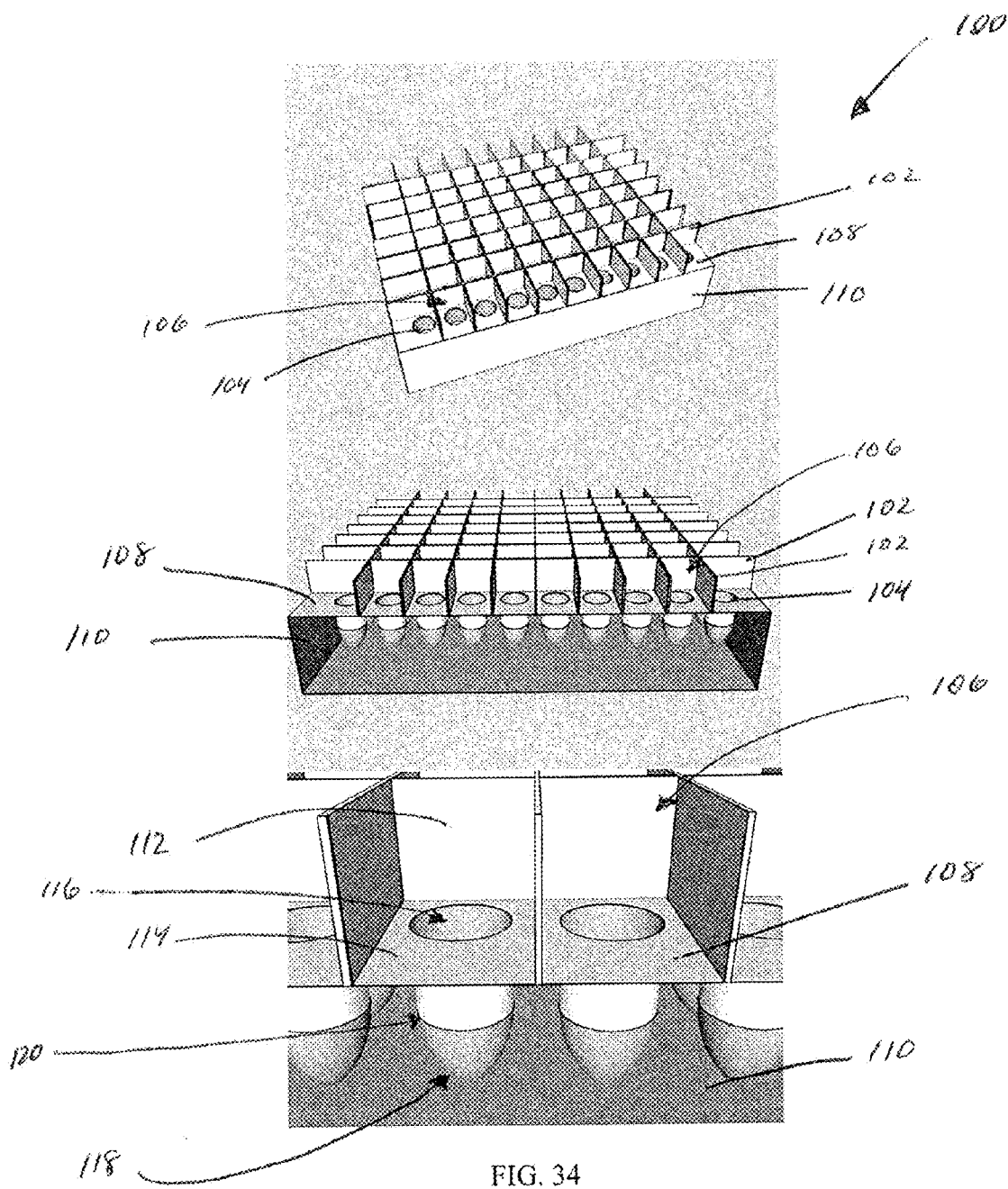
FIG. 34 is a schematic illustrating the design of a walled-micro-mold, wherein walls surround each single divot.

FIG. 34 illustrates a walled-micro-mold 100 that uses walls 102 to circumscribe single divots 104 to effectively create a well 106 defined by the top surface 108 of the micro-mold substrate 110 and the interior surface 112 of the walls 102. The divot 104 is disposed in the bottom surface 114 of the well 106, which corresponds to the top surface 108 of the substrate 110. The addition of walls 102 to the top surfaces 108 of the micro-molds enables liquid separation of the circumscribed divots 104 from adjacent divot openings or multiple sets of divots openings. Similar to those described herein elsewhere, each divot 104 of the micro-mold 100 is defined by an opening 116 in the top surface 108 of the substrate 110 (corresponding to the bottom surface of the well 114), a concave or rounded bottom surface 118 and interior side-wall surface 120 (although the figures illustrate a bullet-shaped bottom, this is an artifact of the drawing software and the actual molds are preferably more concave and/or rounded than bullet-shaped).

Figure 35:
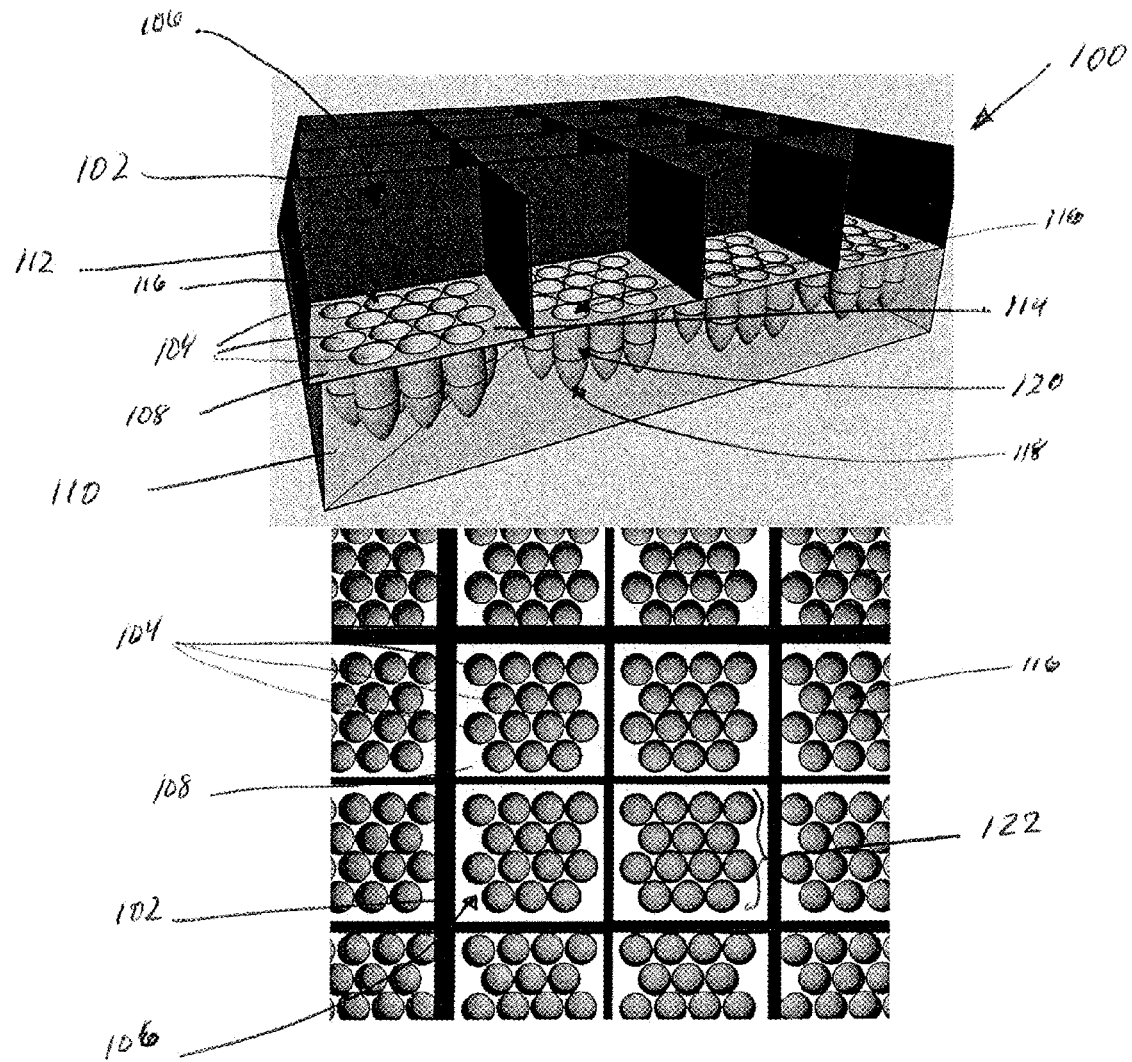
FIG. 35 is a schematic illustrating the design of a walled-micro-mold, wherein walls surround multiple divots.

One preferred aspect of these plates is that the user can generate 3D reaggregated cell clusters in the same plate that would be used for high-throughput drug screening. Using a standard 384-well plate design (85.5×127.8 mm dimensions), 1-14 divots can be created within each single well of the plate (FIGS. 34 and 35). A 1536 well plate with 14 divots/well would have positions for creating 21,504 cell clusters on a single place. In high-throughput drug testing, hundreds of thousands of chemical compounds are screened at once. Skilled artisans appreciate that this high scale of production is a great asset to the pharmaceutical industry.

FIG. 35 illustrates another embodiment of the wall-micro-mold 100. Here, the micro-mold 100 includes walls 102 to circumscribe or surround multiple divots 104. Therefore, each resultant well 106 segregates a set 122 of divots 104 from adjacent sets of divots.

Using walled micro-molds 100, each drug within a single well 106 can be in contact with up to 14 or more different cell clusters, providing an average response/well. The number of cell clusters created per well can be altered depending on the end-user's goals. The walled micro-mold design improves reliability of assayed cellular response to test compounds because the user is not relying on a single intact islet or a single cell cluster to measure a response. Rather, the response assayed in each well may be an average response of 3-14 cell clusters.

Utility of Walled-Micro-Mold for High Throughput Screening.

Cells, grown as a monolayer in a Petri dish are most frequently used to screen drugs. However, a monolayer growth environment can cause cultured cells to respond differently to chemical stimuli than they would in their in vivo environment. For example, insulin-secreting beta cells do not secrete insulin in the same manner when they are spread out flat in a Petri dish as when they are found in the 3D spheroids that resemble their in vivo structure. It follows that using 3D spheroids might be more indicative of in vivo cellular responses to chemicals. However, using 3D spheroids in compound screening has proven to be challenging. For example, variability that occurs within islets from the same donor can be problematic for screening. Small islets release more insulin in response to high glucose concentrations that large islets (MacGregor et al., Am. J. Physiol. Endocrinol. Metab. 2006; 290(5):E771-779). In this Example, islets taken from the same donor rats were separated into large and small sizes and exposed to high glucose at time 0 (FIG. 30). The small islet had a significantly higher release of insulin at normal and high glucose concentrations. Thus, islets from the same donor demonstrate variations in their response to standard stimulants.

Multi-Divot Micro-Molds for Average Responses in Drug Screening.

Figure 32:
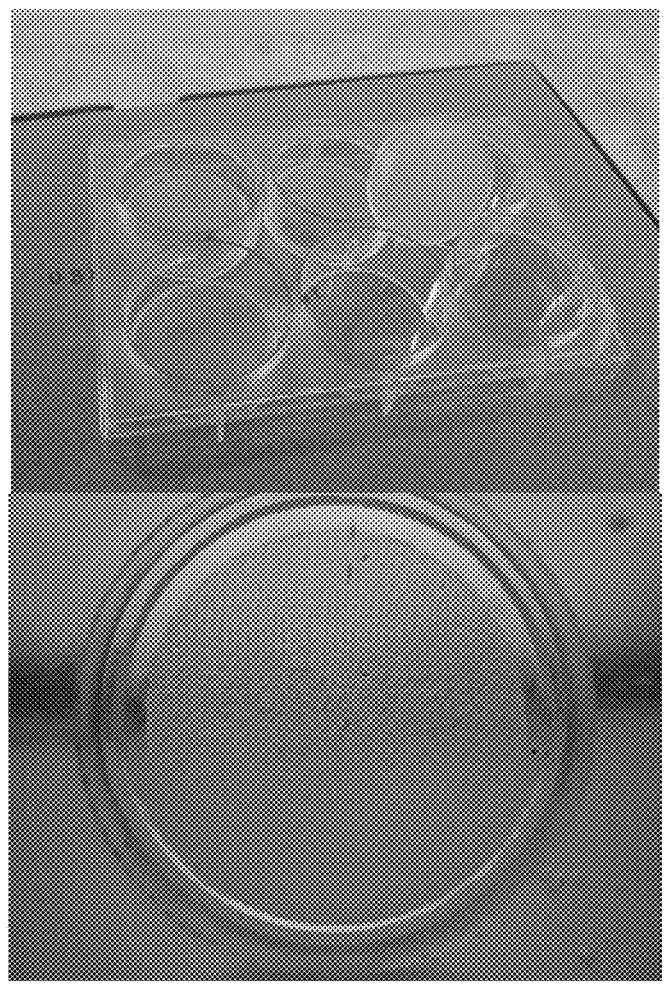
FIG. 32 illustrates that the micro-mold can be produced to fit within the well of a standard plate (upper panel) or can be a free-standing mold (lower panel).
Figure 33:
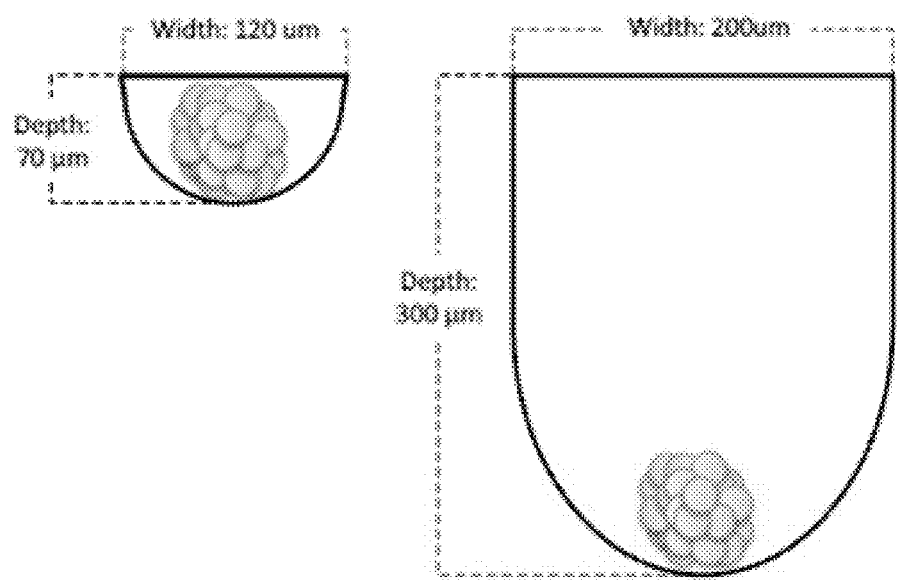
FIG. 33 illustrates variations in divot depth that can create more specificity for the user.

The micro-mold set forth in Example 5 is particularly useful when the resulting cell clusters are to be removed from the mold for research or transplant purposes. The mold described in Example 5 can be free standing or designed to fit within the borders of other standard plates (FIG. 32). The depth of each divot within the well can be individually altered. The mold in Example 5 uses a divot depth of 60-70 µm, which is sufficient for most 3D cell cluster formation. However, it can be advantageous for some cells, especially cancer cells, to provide a deeper divot. With our technology, the well depth can be extended to 300 µm (FIG. 33).

A preferred embodiment of the claimed invention is the walled-micro-mold. These plates contain wells each including a single divot or multiple divots as shown in FIG. 34. The walled-micro-mold addresses the current challenges facing high throughput drug screening and toxicology testing of 3D tissue as follows.

First Challenge: Uniformity of Organotypic Cell Clusters.

Figure 36:
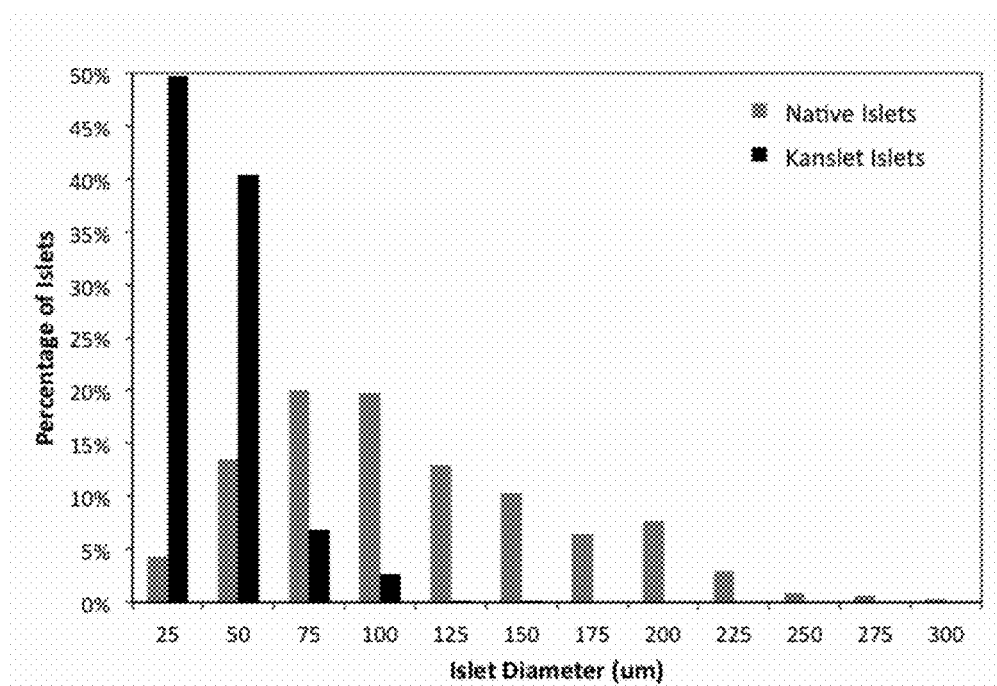
FIG. 36 illustrates production of uniformly-sized micro-mold-derived islet cell clusters.

As discussed in Example 5, cell clusters formed in micro-molds can be removed or remain in the mold for drug testing. Cells clusters generated in micro-mold created be seeding the mold with islet cells from the pancreas are typically called KANSLETS™. However, for the purposes of this Example, KANSLETS™ will be referred to as micro-mold-derived islet cell clusters. Micro-mold derived islet cell clusters have a more uniform size and cell composition relative to native islets, making them advantageous for drug screening and diagnostic testing. FIG. 36 illustrates the variability in the size of native islets (gray bars) compared to the micro-mold-derived islet cell cluster (black bars). Note that after engineering in the micro-mold, the size of the islets is reduced so that the diameter of all of the micro-mold-derived islet cell clusters is 100 µm or less.

In addition, micro-mold-derived islet cell clusters are advantageous cell clusters for drug testing and diagnostics because they have the same general cellular composition as native islets. In both native islets and in micro-mold-derived islet cell clusters, the percentage of cells that are beta cells are approximately 70-75%. Further, this composition does not vary dramatically from micro-mold-derived islet cell cluster to micro-mold-derived islet cell cluster.

Second Challenge: Low Diffusion Barrier.

Figure 37:
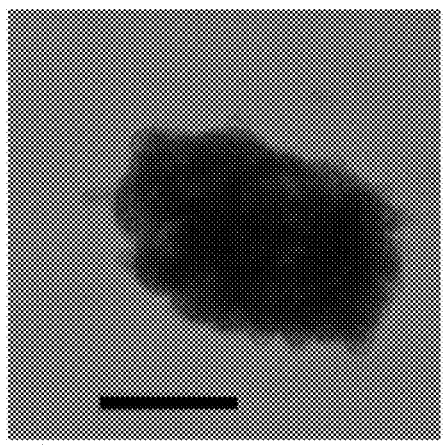
FIG. 37 illustrates a large islet wherein there is little glucose diffusion into the core of the islet. Scale bar=100 µm.

Native islets have a dramatic diffusion barrier. Native large rat islets perfused with a fluorescently-tagged glucose molecule for three hours remain impermeable to glucose, due to an inherent diffusion barrier (FIG. 37). Micro-mold-derived islet cell clusters exposed to the same fluorescent glucose are permeable to glucose (FIG. 26). Micro-mold-derived islet cell clusters exhibit diffusion rates that were beyond our ability to resolve with an imaging scan speed of 2 scans/sec. Immediately when the glucose-containing media contacted the engineered micro-mold-derived islet cell cluster glucose entered the core of the cluster. Table 2 provides the average diffusion rates for the fluorescent glucose to enter intact human or rat islets compared to human or rat micro-mold-derived islet cell clusters.

TABLE 2

Rates of glucose diffusion into native rat and human islets relative to micro-mold-derived islet cell clusters.

| Diffusion (μm/min) | Human | Rat |
| --- | --- | --- |
| Small islets | 2.8 | 4.2 |
| Large islets | 1.7 | 2.8 |
| Micro-mold-derived islet cell clusters | Instantaneous | Instantaneous |

Third Challenge: Consistent Response to Test Compounds.

Figure 38:
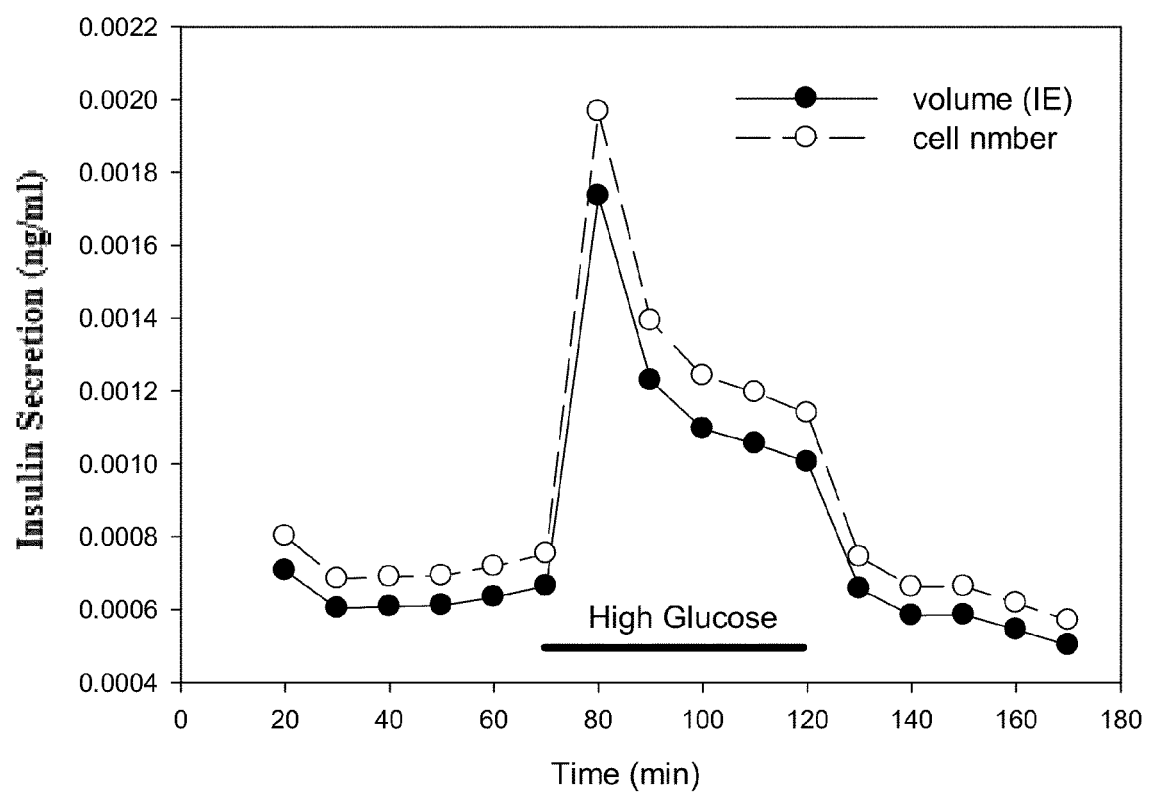
FIG. 38 illustrates response of micro-mold-derived rat islet cell cluster to high glucose (20 mM). An expected sharp rise in insulin secretion occurs at 80 minutes, followed by a return to basal levels following glucose stimulation.

There is high variability when working with intact, native islets for drug screening to find new diabetes drugs (FIG. 30). Micro-mold-derived islet cell clusters overcome this problem by providing a uniform response between trials and donors. FIG. 38 shows the micro-mold-derived islet cell clusters' response to a high glucose stimulation (using the same protocol as shown in FIG. 30). It is evident that the micro-mold-derived islet cell clusters responded to high glucose in the predicted manner with little variability. The response was the same whether calculated by volume or cell number. The same is not true when working with native islets of different sizes. Much of the uniformity in response comes from the fact that the micro-mold-derived islet cell clusters are all approximately the same size and cell conformation.

Negative compounds, i.e., drugs that should not stimulate a release of insulin, have also been successfully tested with micro-mold-derived islet cell clusters. In every case, the micro-mold-derived islet cell clusters have adequately predicted the response known in humans from these compounds (data not shown).

Fourth Challenge: Compatibility with High-Throughput Drug Screening Instruments

Figure 39:
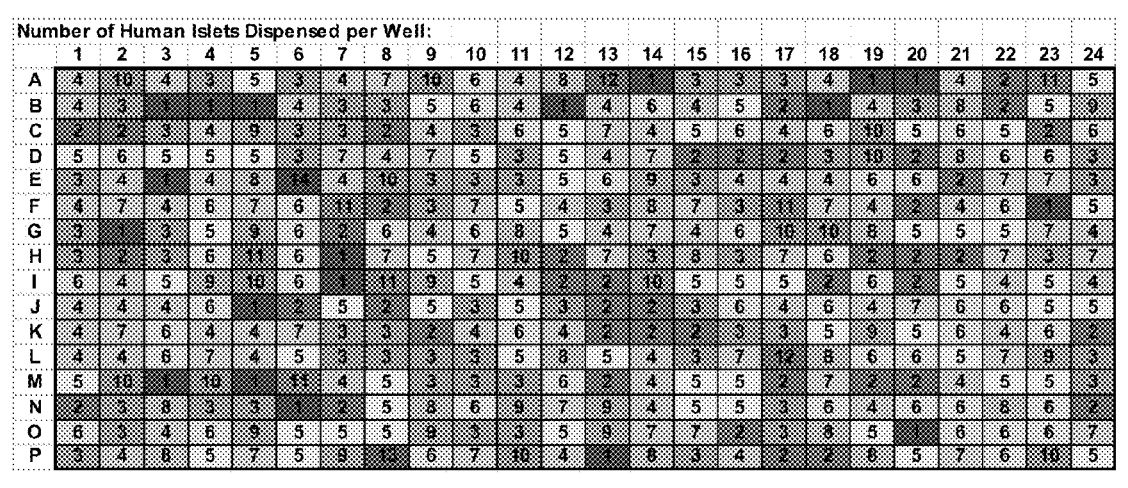

We have attempted to use native islets as a primary drug screen using current pharmaceutical industry instruments. Native islets cannot be distributed evenly using the PlateMate® or WellMate® (Thermo fisher Scientific, Hudson, N.H.) dispersion instruments (even when only using small islets) (FIG. 39); islet number/well varied from 1-14 islets/well, which is unacceptable for drug screening. This level of variation in the number of islets is compounded when native islets are considered. For example, native islets vary from 10s of cells/islet to 1000s of cells/islet, a difference between 1 and 14 islets per well can amount to a difference of more than a 1000 times more cells in one well relative to another. However, standard practice in the pharmaceutical industry is to test each drug dose only in one well. With such variation in the number of responding cells from well to well, the industry cannot use native islets for primary screening, because they would not be able to interpret the results.

Micro-mold-derived islet cell clusters are small, allowing them to be dispersed using standard industry instruments such that approximately the same number of micro-mold-derived islet cell clusters are seeded in each well. Thus, a narrower range of values can be achieved when calculating islet cells/well. Further, micro-mold-derived islet cell clusters are all the same size, so the variation present when calculating the number of cells/well is significantly less relative to native islets.

Further, the walled-micro-mold can be used as both a reaggregation plate and a testing plate. In this format, islet cells (or other cell types) would be seeded into the walled-micro mold for a time sufficient to reaggregate the cells into clusters. The walled-micro-mold would then be loaded onto an industry instrument for addition and testing of compounds. FIGS. 34 and 35 show micro-mold designs optimized for cell cluster formation and drug testing in the same mold. If there were 14 divots/well, then the scientist would be testing 14 uniform micro-mold-derived islet cell clusters per drug dose, resulting in a highly reproducible assay platform.

Fifth Challenge: Scalability to High-Throughput Needs.

Figure 40:
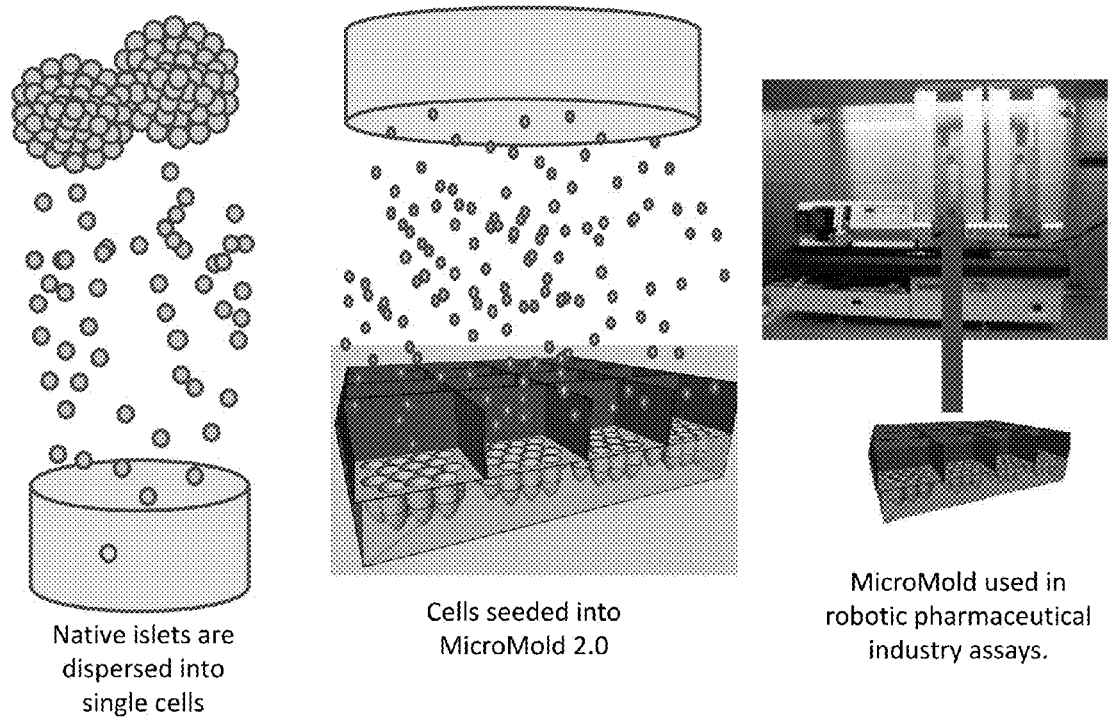
FIG. 40 is a schematic representation of the method for generating cell clusters in the same micro-mold that is used for high-throughput screening.

Due to the fact that micro-mold-derived islet cell clusters (or other engineered cell clusters generate din the micro-mold) can be dispersed using standard instruments, and the molds can be designed to fit a standard 1536 well format, the walled-micro-mold is easily scalable to current high-throughput needs (FIG. 40). Native islets are dispersed into single cells, which are then loaded into a walled-micro-mold with multiple divots/well. After 3-5 days, the cells reaggregate into cell clusters of consistent size, shape, and cell composition. The same walled-micro-mold is then loaded into the standard industry instruments for drug dispensing and subsequent testing within the same plate. Because the base of the micro-mold is glass, high content screening can be easily accomplished.

Sixth Challenge: Ability to Maintain Long-Term Experiments.

Figure 41:
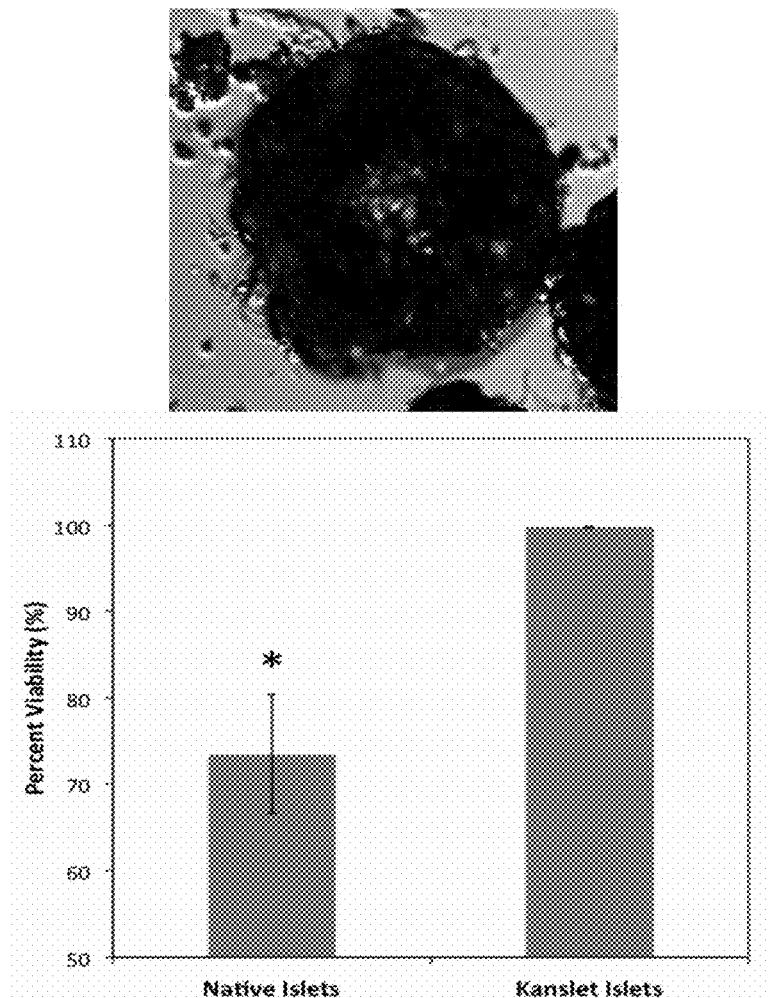
FIG. 41 illustrates cell viability of native islets relative to micro-mold-derived islet cell clusters. Staining of native islets for dead cells (red or green) indicates core death following only a few hours in culture (upper panel). Viability is significantly improved for micro-mold-derived islet cell clusters relative to native islets (lower panel).

Native islets and other human tissues typically do not survive for lengthy periods of time once removed from the body unless they are transformed into culture lines, which frequently causes the cells to lose phenotypic features associated with their host tissue. Over multiple experiments, the viability of micro-mold-derived islet cell clusters is always higher than the native islets (FIG. 41). This is especially true for long-term experiments in which the cells must be maintained for more than a week.

Micro-mold-derived islet cell clusters provide an important improvement in other 3D technologies because they can be produced and tested within the same mold. Each transfer step that is eliminated in the production and testing procedure improves the efficiency (less tissue is lost) and reduces the risk of contamination. When we have attempted to use intact native islets for drug screening they became contaminated within a few hours because three transfer steps were required for testing. Micro-mold-derived islet cell clusters overcome that issue by never requiring transfer out of the walled-micro-mold.

Other Cell Clusters that can be Generated in Micro-Molds.

Figure 42:
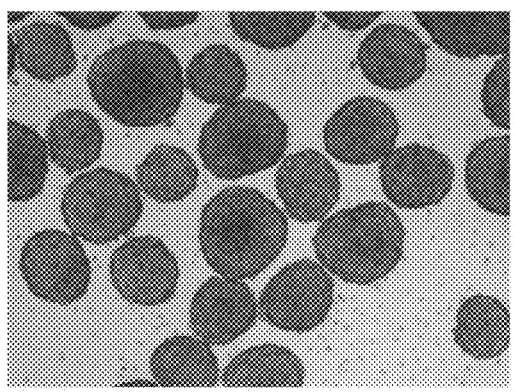
FIG. 42 illustrates human lung cancer spheroids produced in the disclosed micro-molds.

Cell types other than islets can be reaggregated in walled-micro-molds for drug and toxicology screening. Cancerous tumors in situ exist in a three-dimensional environment. Considering that most drug tests are conducted on cell monolayers, the correlation between the in vitro experimentation and the eventual in vivo usage poses challenges. FIG. 42 shows uniform 3D lung cancer spheroids produced in the micro-molds described herein. We have also formed spheroids from other cancer cell lines using the disclosed micro-molds (data not shown).

Summary.

The micro-mold described in this Example significantly advances the ability to use multi-cell type 3D cell clusters in drug discovery and regenerative medicine focused on cell cluster transplantation. The cell clusters retrieved from the micro-molds described herein provide uniform cellular 3D spheroids that can be stored long-term with cryopreservation. In testing, they provide a more uniform response that is more predictive of the in vivo response to compounds. It also opens new doors when considering cellular transplants from preserved tissue mixed with the recipients own cells.

From the foregoing it will be seen that this invention is one well adapted to attain all ends and objectives set forth herein, together with the other advantages which are obvious and inherent to the invention. Since many variations are possible without departing from the scope of the invention, it is to be understood that all matters herein set forth are to be interpreted as illustrative, and not in a limiting sense. While specific embodiments have been shown and discussed, various modifications may be made, and the invention is not limited to the specific forms or arrangement of parts and steps described herein. All patent applications, patents, and publications cited in this specification are hereby incorporated by reference in their entirety.

REFERENCES

The following references, to the extent that they provide exemplary procedural or other details supplementary to those set forth herein, are specifically incorporated herein by reference.

SU-8 2000—Permanent Epoxy Negative Photoresist, MicroChem, Newton, Mass.

Balmurgan A N, Chang Y, Fung J J, Trucco M, and Bottino R., Flexible management of enzymatic digestion improves human islet isolation outcome from sub-optimal donor pancreata, Am J Transplantation 3: 1135-1142, (2003).

Bosco D, Armanet M, Morel P, Niclauss N, Sgroi A, Muller Y D, Giovannoni L, Parnaud G, Berney T, Unique arrangement of alpha- and beta-cells in human islets of Langerhans, Diabetes. February 25. [Epub ahead of print] (2010).

Chan C B, Saleh M C, Purje A, and MacPhail R M, Glucose-inducible hypertrophy and suppression of anion efflux in rat beta cells, J Endocrinol 173: 45-52, (2002).

Chan C B and Surette J J, Glucose refractoriness of beta-cells from fed fa/fa rats is ameliorated by nonesterified fatty acids, Can J Physiol Pharmacol 77: 934-942, (1999).

Crim W S, Wu R, Carter J D, Cole B K, Trace A P, Mirmira R G, Kunsch C, Nadler J L, Nunemaker C S. AGI-1067, a novel antioxidant and anti-inflammatory agent, enhances insulin release and protects mouse islets. Mol Cell Endocrinol. March 6. [Epub ahead of print] (2010).

Cui Y-F, Ma M, Wang G-Y, D-E. H, Vollmar B, and Menger M D, Prevention of core cell damage in isolated islets of Langerhans by low temperature preconditioning, World J Gastroenter 11: 545-550, (2005).

Dean et al., Comparison of insulin autoantibodies in diabetes-related and healthy populations by precise displacement ELM, Diabetes (1989).

Dean, D. M., Napolitano, A. P., Youssef, J., Morgan, J. R. (2007) Rods, tori, and honeycombs the directed self-assembly of microtissues with prescribed microscale geometries. FASEB J. 21, 4005-4012.

Dufrane D, Goebbels R M, Fdilat l, Guiot Y, and Gianello P, Impact of porcine islet size on cellular structure and engraftment after transplantation: adult versus young pigs, Pancreas 30: 138-147, (2005).

Hahn von Dorsche, H., Reiher, H., Hahn, H J., Phases in the early development of the human islet organ, Anat Anz., 166 (1-5):69-76 (1988).

Healy L, Young L, Stacey G N. Stem cell banks: preserving cell lines, maintaining genetic integrity, and advancing research. Methods Mol. Biol. 2011; 767:15-27.

Huang H-H, Novikova L, Williams S J, Smirnova I V, Stehno-Bittel L. Low insulin content of large islet population is present in situ and in isolated islets. Islets. 2011; 3(1):6-13.

Hutton J C and Malaisse W J, Dynamics of O2 consumption in rat pancreatic islets, Diabetologia 18: 395-405, (1980).

Kaihow T, Masuda T, Sasano N, and Takahashi T, The size and number of Langerhans islets correlated with their endocrine function: a morphometry on immunostained serial sectioned adult human pancreases, Tohoku J Exp Med 149: 1-10, (1986).

Kawashima Y, Yamamoto H, Takeuchi H and Kuno Y, Mucoadhesive DL-lactide/glycolide copolymer nanospheres coated with chitosan to improve oral delivery of elcatonin, Pharm Dev Technol 5:77-85 (2000).

Keegan M, Falcone J, Leung T and Saltzman W M, Biodegradable microspheres with enhanced capacity for covalently bound surface lipids, Macromol 37:9779-9784 (2004).

Kikugawa, R., H. Katsuta, et al. (2009). Differentiation of COPAS-sorted non-endocrine pancreatic cells into insulin-positive cells in the mouse. Diabetologia 52(4): 645-52.

Koh A, Senior P, Salam A, Kin T, Imes S, Dinyari P, Malcolm A, Toso C, Nilsson B, Korsgren O, Shapiro A M. Insulin-heparin infusions peritransplant substantially improve single-donor clinical islet transplant success., Transplantation. 89(4):465-71, (2010).

Krickhahn M, Buhler C, Meyer T, Thiede A, and Ulrichs K, The morphology of islets within the porcine donor pancreas determines the isolation result: successful isolation of pancreatic islets can now be achieved from young market pigs, Cell Transplant 11: 827-838, (2002).

Lakey J R, Burridge P W, Shapiro A M. Technical aspects of islet preparation and transplantation. Transpl Int. 2003 September; 16(9):613-32.

Lehmann R, Zuellig R A, Kugelmeier P, Bainninger P B, Moritz W, Perren A, Claviens P-A, Weber M, Spinas G A, Superiority of Small Islets in Human Islet Transplantation. Diabetes 56, 504-603 (2007).

Mata A, Fleischman A J, Roy S, Characterization of Polydimethylsiloxane (PDMS) Properties for Biomedical Micro/Nanosystems, Biomedical Microdevices 7(4): 281-293 (2005).

Mattson G, Jansson L, and Carlsson P-O, Decreased vascular density in mouse pancreatic islets after tranplantation, Diabetes 51: 1362-1366, (2002).

Menger M D, Jaeger S, Walter P, Feifel G, Hammersen F, and Messmer K, Angiogenesis and hemodynamics of microvasculature of transplanted islets of Langerhans, Diabetes 38 Suppl: 199-201, (1989).

Nirmalanandhan V, Duren A, Hendricks P, Vielhauer G, Sittampalam G. Activity of anticancer agents in a three-dimensional cell culture model. Assay Drug Dev Technol. 2010; 8(5):581-590.

O'Sullivan E S, Johnson A S, Omer A, Hollister-Lock J, Bonner-Weir S, Colton C K, Weir G C. (2010) Rat islet cell aggregates are superior to islets for transplantation in microcapsules. Diabetologia 2010 January 26. [Epub ahead of print].

Petropavlovskaia M and Rosenberg L, Identification and characterization of small cells in the adult pancreas: potential progenitor cells?, Cell Tissue Res 310: 51-58, (2002).

Qi Z, Shen Y, Yanai G, Yang K, Shirouzu Y, Hiura A, Sumi S. The in vivo performance of polyvinyl alcohol macro-encapsulated islets. Biomaterials. 31(14):4026-31, (2010).

Ramachandran K, Williams S J, Huang H-H, Novikova L, Stehno-Bittel L. Engineering islets for improved performance by optimized reaggregation in a micro-mold. Tissue Engineering, accepted pending revision.

Ritz-Laser B, Oberholzer J, Toso C, Brulhart M C, Zakrzewska K, Ris F, Bucher P, Morel P, and Philippe J, Molecular detection of circulating beta-cells after islet transplantation, Diabetes 51: 557-561, (2002).

Scharp D W, Lacy P E, Santiago J, McCullough C, Weide L G, Falqui L, Marchetti P, Gingerich R, Jaffe A, Cryer P, Anderson C, and Flye W, Insulin independence following islet transplantation into patient with Type 1, insulin dependent diabetes mellitus, Diabetes 39: 515-518, (1990).

Shapiro A M, Lakey J R, Ryan E A, Korbutt G S, Toth E, Warnock G L, Knetman N M, and Rajotte R V, Islet transplantation in seven patients with type I diabetes mellitus using a glucocorticoid-free immunosuppressive regime, New England J Med 343: 230-238, (2000).

Song H J, Xue W J, Li Y, Tian X H, Song Y, Ding X M, Feng X S, Tian P X, Li Z L., Improved islet survival and function with rat endothelial cells in vitro co-culture. Transplant Proc. December; 41(10):4302-6, (2009).

Sutherland D E, Gores P F, Farney A C, Wahoff D C, Matas A J, Dunn D L, Gruessner R W, and Najarian J S, Evolution of kidney, pancreas, and islet transplantation for patients with diabetes at the University of Minnesota, Am J Surg 166: 456-491, (1993).

Sweet I R, Khalil G, Wallen A R, Steedman M, Schenkman K A, Reems J A, Kahn S E, and Callis J B, Continuous measurement of oxygen consumption by pancreatic islets, Diabetes Technol Ther 4: 661-672, (2002).

Tatarkiewicz K, Garcia M, Lopez-Avalos M, Bonner-Weir S, and Weir G C. Porcine neonatal pancreatic cell clusters in tissue culture: benefits of serum and immobilization in alginate hydrogel, Transplanation 71: 15181526, (2001).

Taylor M J, Baicu S. Review of vitreous islet cryopreservation. Organogenesis. 2009; 5(3):155-166.

Vériter S, Mergen J, Goebbels R M, Aouassar N, Grégoire C, Jordan B, Levêque P, Gallez B, Gianello P, Dufrane D. In Vivo Selection of Biocompatible Alginates for Islet Encapsulation and Subcutaneous Transplantation, Tissue Eng Part A. February 11, [Epub ahead of print], (2010).

von Mach M A, Schlosser 3, Weiland M, Feilen F J, Ringel M, Hengstler J G, Weilemann L S, Beyer J, Kann P, and Schneider S, Size of pancreatic islets of Langerhans: a key parameter for viability after cryopreservation, Acta Diabetol 40: 123-129, (2003).

Warnock G L, Ellis D K, Cattral M, Untch D, Kneteman N M, and Rajotte R V, Viable purified islets of Langerhans from collagenase-perfused human pancreas, Diabetes 38:136-139 (1989).

Williams, S J., Wang, MacGregor, R., Q., Siahaan, T., Stehno-Bitel, L., Berkland, C. (2009) Adhesion of pancreatic beta cells to biopolymer films, Biopolymers, 91(8):676-685.

Williams S, Huang H-H, Kover K, Moore W, Berkland C, Singh M, Smirnova I V, Macgregor R, Stehno-Bittel L. Reduction of diffusion barriers in isolated rat islets improves survival, but not insulin secretion or transplantation outcome. Organogenesis. 2010; 6(2):115-124.

Xu W, McDough R C, Langsdorf B, Demas 1N, and DeGraff B A, Oxygen sensors based on luminescence quenching: interaction metal complexes with the polymer supports, Anal Chem 66: 4133-4141 (1994).

---

---

We claim:

1. A method of evaluating a xenobiotic for biological activity, said method comprising:
    providing a device comprising:
        a substrate having a substantially planar top surface;
        a side-wall extending upwardly from the surface in a direction generally perpendicular to a plane defined by the top surface and circumscribing a portion of the surface, said side-wall and top surface cooperatively forming a liquid impermeable well, wherein the well has a bottom surface corresponding to the portion of the top surface circumscribed by the sidewall; and
        a plurality of divots disposed in the bottom surface of the well,
    wherein each divot is defined by an opening in the bottom surface of the well, a rounded bottom surface spaced from the opening, and an interior side-wall surface extending between the rounded bottom surface and the opening, said divots being free of coatings that increase cell adhesion, wherein each divot has a depth of between 50-300 µm and a diameter of between 100-300 µm;

said device comprising a plurality of said wells, each well comprising a plurality of said divots;

culturing cells in said divots to form a 3-dimensional cell cluster in each divot;

adding a first xenobiotic to at least a first well, wherein said first xenobiotic comes into contact with a first plurality of cell clusters in said first well, each cell cluster being in respective divots in said first well; and evaluating the effects of said first xenobiotic on said first plurality of cell clusters.

2. The method of claim 1, said method further comprising determining the average effect of said first xenobiotic on said first plurality of cell clusters.

3. The method of claim 1, further comprising:

adding a second xenobiotic to at least a second well, wherein said second xenobiotic comes into contact with at least a second plurality of cell clusters in said second well, each cell cluster being in respective divots in said second well; and evaluating the effects of said second xenobiotic on said second plurality of cell clusters.

4. The method of claim 3, said method further comprising determining the average effect of said second xenobiotic on said second plurality of cell clusters.

5. The method of claim 3, wherein said first and second xenobiotics are added to said device substantially simultaneously.

6. The method of claim 1, wherein each divot comprises a single 3-dimensional cell cluster.

7. The method of claim 1, wherein said 3-dimensional cell clusters are islets.

8. The method of claim 1, wherein said substrate is selected from the group consisting of glass and plastic.

9. The method of claim 1, said substrate being etched glass, wherein said divots are etched into said substrate.

10. The method of claim 1, wherein said 3-dimensional cell cluster comprises reaggregated cells selected from the group consisting of islet cells, cancer cells, stem cells, and combinations thereof.

11. The method of claim 1, wherein said 3-dimensional cell cluster has a diameter of less than about 100 µm.

12. The method of claim 1, wherein said device is non-implantable.

13. The method of claim 1, wherein said evaluating the effects of said first xenobiotic on said first plurality of cell clusters is carried out without transferring said first plurality of cell clusters out of said device.

14. The method of claim 1, wherein after culturing, said first plurality of cell clusters is not transferred out of said device during said adding or said evaluating.

15. The method of claim 1, wherein said evaluating comprises examining said first plurality of cell clusters and noting changes in said cluster.

16. The method of claim 15, wherein said examining comprises assaying said first plurality of cell clusters for cell viability.

17. The method of claim 1, wherein said evaluating comprises testing said first plurality of cell clusters for biological activity after contact with said xenobiotic.

* * * * *